US008652778B2

(12) United States Patent
Bowman et al.

(10) Patent No.: US 8,652,778 B2
(45) Date of Patent: *Feb. 18, 2014

(54) USE OF PHOTOPOLYMERIZATION FOR AMPLIFICATION AND DETECTION OF A MOLECULAR RECOGNITION EVENT

(75) Inventors: Christopher N. Bowman, Boulder, CO (US); Kathy Rowlen, Boulder, CO (US); Hadley Sikes, Pasadena, CA (US); Ryan Hansen, Golden, CO (US); Heather Jean Avens, Lafayette, CO (US)

(73) Assignee: The Regents of the University of Colorado, A Body Corporate, Denver, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/082,814

(22) Filed: Apr. 8, 2011

(65) Prior Publication Data
US 2011/0251092 A1    Oct. 13, 2011

Related U.S. Application Data

(63) Continuation of application No. 12/099,560, filed on Apr. 8, 2008, now abandoned, which is a continuation-in-part of application No. 11/372,485, filed on Mar. 9, 2006, now Pat. No. 7,354,706, which is a continuation-in-part of application No. PCT/US2004/029733, filed on Sep. 9, 2004.

(60) Provisional application No. 60/988,563, filed on Nov. 16, 2007, provisional application No. 60/982,992, filed on Oct. 26, 2007, provisional application No. 60/662,313, filed on Mar. 16, 2005, provisional application No. 60/501,755, filed on Sep. 9, 2003.

(51) Int. Cl.
| C12Q 1/68 | (2006.01) |
|---|---|
| C40B 30/04 | (2006.01) |
| B82Y 30/00 | (2011.01) |

(52) U.S. Cl.
USPC ............................... 435/6.1; 506/9; 977/773

(58) Field of Classification Search
None
See application file for complete search history.

(56) References Cited

U.S. PATENT DOCUMENTS

| 4,749,647 | A | * | 6/1988 | Thomas et al. ................ 435/5 |
|---|---|---|---|---|
| 4,876,187 | A | | 10/1989 | Duck et al. |
| 5,011,769 | A | | 4/1991 | Duck et al. |
| 5,019,496 | A | | 5/1991 | Oster et al. |
| 5,124,246 | A | | 6/1992 | Urdea et al. |
| 5,175,270 | A | | 12/1992 | Nilsen et al. |
| 5,185,243 | A | | 2/1993 | Ullman et al. |
| 5,196,306 | A | | 3/1993 | Bobrow et al. |
| 5,359,100 | A | | 10/1994 | Urdea et al. |
| 5,403,711 | A | | 4/1995 | Walder et al. |
| 5,449,602 | A | | 9/1995 | Royer et al. |
| 5,484,904 | A | | 1/1996 | Nilsen et al. |
| 5,487,973 | A | | 1/1996 | Nilsen et al. |
| 5,545,730 | A | | 8/1996 | Urdea et al. |
| 5,571,670 | A | | 11/1996 | Urdea et al. |
| 5,573,907 | A | | 11/1996 | Carrino et al. |
| 5,580,731 | A | | 12/1996 | Chang et al. |
| 5,591,584 | A | | 1/1997 | Chang et al. |
| 5,594,117 | A | | 1/1997 | Urdea et al. |
| 5,594,118 | A | | 1/1997 | Urdea et al. |
| 5,597,909 | A | | 1/1997 | Urdea et al. |
| 5,624,802 | A | | 4/1997 | Urdea et al. |
| 5,635,352 | A | | 6/1997 | Urdea et al. |
| 5,637,460 | A | | 6/1997 | Swan et al. |
| 5,660,988 | A | | 8/1997 | Duck et al. |
| 5,681,697 | A | | 10/1997 | Urdea et al. |
| 5,681,702 | A | | 10/1997 | Collins et al. |
| 5,710,264 | A | | 1/1998 | Urdea et al. |
| 5,770,722 | A | | 6/1998 | Lockhart et al. |
| 6,096,369 | A | | 8/2000 | Anders et al. |
| 6,361,944 | B1 | | 3/2002 | Mirkin et al. |

(Continued)

FOREIGN PATENT DOCUMENTS

| EP | 0 383 126 | 8/1990 |
|---|---|---|
| WO | WO 00/43539 | 7/2000 |

(Continued)

OTHER PUBLICATIONS

Tan et al. Bionanotechnology Based on Silica Nanoparticles. 2004. Medicinal Research Reviews, vol. 24, No. 5, pp. 621-638.*
Taton et al. Scanometric DNA Array Detection with Nanoparticle Probes. Sep. 8, 2000. Science. vol. 289, p. 1757-1760.*
Andras et al. (2001) "Strategies for Signal Amplification in Nucleic Acid Detection," *Mol. Biotechnol.* 19:29-44.
Anthony et al. (2000) "Rapid Diagnosis of Bacteria by Universal Amplification of 23S Ribosomal DNA Followed by Hybridization to an Oligonucleotide Array," *J. Clin. Microbiol.* 38:781-788.
Avens et al. (Sep. 2008) "Polymerization Behavior and Polymer Properties of Eosin-Mediated Surface Modification Reactions," *Polymer* 49:4762-4768.
Avens et al. (2009) "Mechanism of Cyclic Dye Regeneration During Eosin-Sensitivity Photoinitiation in the Presence of Polymerization Inhibitors," *J. Polym. Sci. Polym. Chem.* 47:6083-6094.

(Continued)

*Primary Examiner* — Anne Gussow
*Assistant Examiner* — Channing S Mahatan
(74) *Attorney, Agent, or Firm* — Lathrop & Gage LLP; Tamala R. Jonas; Sally Sullivan

(57) ABSTRACT

The invention provides methods to detect molecular recognition events. The invention also provides methods to detect the presence of or identify a target species based on its interaction with one or more probe species. The methods of the invention are based on amplification of the signal due to each molecular recognition event. The amplification is achieved through photopolymerization, with the polymer formed being associated with the molecular recognition event. In one aspect, a fluorescent polymer, a magnetic polymer, a radioactive polymer or an electrically conducting polymer can form the basis of detection and amplification. In another aspect, a polymer gel swollen with a fluorescent solution, a magnetic solution, a radioactive solution or an electrically conducting solution can form the basis of detection and amplification. In another aspect, detectable particles can be included in the polymer formed. In another aspect, sufficient polymer forms to be detectable by visual inspection.

34 Claims, 16 Drawing Sheets

(56) References Cited

U.S. PATENT DOCUMENTS

| | | | |
|---|---|---|---|
| 6,372,937 | B1 | 4/2002 | Bobrow et al. |
| 6,406,845 | B1 * | 6/2002 | Walt et al. ............... 435/6.11 |
| 6,417,340 | B1 | 7/2002 | Mirkin et al. |
| 6,485,703 | B1 | 11/2002 | Cote et al. |
| 6,495,324 | B1 | 12/2002 | Mirkin et al. |
| 6,506,564 | B1 | 1/2003 | Mirkin et al. |
| 6,582,921 | B2 | 6/2003 | Mirkin et al. |
| 6,593,100 | B2 | 7/2003 | Bobrow et al. |
| 6,602,669 | B2 | 8/2003 | Letsinger et al. |
| 6,610,491 | B2 | 8/2003 | Mirkin et al. |
| 6,645,721 | B2 | 11/2003 | Mirkin et al. |
| 6,667,122 | B2 | 12/2003 | Kaufmann |
| 6,673,548 | B2 | 1/2004 | Mirkin et al. |
| 6,682,895 | B2 | 1/2004 | Mirkin et al. |
| 6,709,825 | B2 | 3/2004 | Mirkin et al. |
| 6,720,147 | B2 | 4/2004 | Mirkin et al. |
| 6,720,411 | B2 | 4/2004 | Mirkin et al. |
| 6,730,269 | B2 | 5/2004 | Mirkin et al. |
| 6,740,491 | B2 | 5/2004 | Mirkin et al. |
| 6,750,016 | B2 | 6/2004 | Mirkin et al. |
| 6,759,199 | B2 | 7/2004 | Mirkin et al. |
| 6,767,702 | B2 | 7/2004 | Mirkin et al. |
| 6,773,884 | B2 | 8/2004 | Mirkin et al. |
| 6,777,186 | B2 | 8/2004 | Mirkin et al. |
| 6,806,047 | B2 | 10/2004 | Goldberg et al. |
| 7,354,706 | B2 * | 4/2008 | Rowlen et al. ............... 435/5 |
| 2002/0001853 | A1 | 1/2002 | Obremski et al. |
| 2002/0071943 | A1 | 6/2002 | Hawker et al. |
| 2003/0236425 | A1 | 12/2003 | Herr et al. |
| 2004/0063146 | A1 | 4/2004 | Sayre et al. |
| 2006/0286570 | A1 | 12/2006 | Rowlen et al. |
| 2009/0005263 | A1 | 1/2009 | Kuck |
| 2009/0137405 | A1 | 5/2009 | Bowman et al. |
| 2009/0163375 | A1 | 6/2009 | Bowman et al. |
| 2012/0071338 | A1 | 3/2012 | Bowman et al. |

FOREIGN PATENT DOCUMENTS

| | | |
|---|---|---|
| WO | WO 2004/093845 | 11/2004 |
| WO | WO 2005/024386 | 3/2005 |
| WO | WO 2006/031248 | 3/2006 |
| WO | WO 2007/095464 | 8/2007 |

OTHER PUBLICATIONS

Avens et al. (2010) "Development of Fluorescent Polymerization-Based Signal Amplification for Sensitive and Non-Enzymatic Biodetection in Antibody Microarrays," *Acta Biomaterialia* 6:83-89.

Avens et al. (Web Release Aug. 1, 2010) "Fluorescent Polymeric Nanocomposite Films Generated by Surface-Mediated Photoinitiation of Polymerization," *J. Nanoparticle Res.* Online Preprint.

Bally et al. (Web Release Oct. 2006) "Optical Microarray Biosensing Techniques," *Surf. Interface Anal.* 38:1442-1458.

Baner et al. (1998) "Signal Amplification of Padlock Probes by Rolling Circle Replication," *Nuc. Acids Res* 26:5073-5078.

Barany, F. (1991) "Genetic Disease Detection and DNA Amplification Using Cloned Thermostable Ligase," *Proc. Natl. Acad. Sci. USA* 88:189-193.

Biesalski et al. (1999) "Segment Density Profiles of Polyelectrolyte Brushes Determined by Fourier Transform Ellipsometry," *J. Chem. Phys.* 111(15):7029-7037.

Bobrow et al. (1991) "Catalyzed Reporter Deposition, A Novel Method of Signal Amplification, II Application to Membrane Immunoassays," *J. Immunol. Methos.* 137:103-112.

Bontempo et al. (Apr. 2005) "Streptavidin as a Macroinitiator for Polymerization: In Situ Protein-Polymer Conjugate Formation", J. Am. Chem. Soc. 127(18), 6508-6509.

Bowman et al. (Nov. 2008) "Toward an Enhanced Understanding and Implementation of Photopolymerization Reactions," *AIChE J.* 54(11):2775-2795.

Cao et al. (Aug. 30, 2002) "Nanoparticles with Raman Spectroscopic Fingerprints for DNA and RAN Detection," *Science* 297:1536-1540.

Collins et al. (1997) "A Branched DNA Signal Amplification Assay for Quantification of Nucleic Acid Targets Below 100 Molecules/ ml," *Nuc. Acids Res.* 25(15):2979-2984.

Cruise et al. (Mar. 20, 1998) "A Sensitivity Study of the Key Parameters in the Interfacial Photopolymerization of Poly(ethylene glycol) Diacrylate Upon Porcine Islets," *Biotechnol. Bioeng.* 57(6):655-665.

Csako et al. (Web Release Aug. 2005) "Present and Future of Rapid and/or High-Throughput Methods for Nucleic Acid Testing," *Clinica Chimica Acta* 363:6-31.

Daubendiek et al. (1997) "Generation of Catalytic RNA's by Rolling Transcription of Synthetic DNA Nanocircles," *Nat. Biotech.* 15:273-277.

Ding et al. (Jan. 2004) "Quantitative Analysis of Nucleic Acids—The Last Few Years of Progress," *J. Biochem. Mol. Biol.* 37(1):1-10.

Do et al. (Feb. 2007) "cDNA Labeling Strategies for Microarrays Using Fluorescent Dyes," *Eng. Life Sci.* 7(1):26-34.

Elghanian et al. (Aug. 22, 1997) "Selective Colorimetric Detection of Polynucleotides Based on the Distance—Dependent Optical Properties of Gold Nanoparticles," *Science* 277:1078-1081.

Englisch et al. (Jun. 1991) "Chemically Modified Oligonucleotides as Probes and Inhibitors," *Angew. Chem. Int. Ed. Eng.* 30(6):613-629.

Epstein et al. (2002) "Fluorescence-Based Nucleic Acid Detection and Microarrays," *Anaytica. Chimica Acta* 469:3-36.

Gaylord et al. (Aug. 20, 2002) "DNA Detection Using Water-Soluble Conjugated Polymers and Peptide Nucleic Acid Probes," *Proc. Nat. Acad. Sci. USA* 99(17):10954-10957.

Hansen et al. (Jul. 2008) "Quantitative Evaluation of Oligonucleotide Surface Concentrations Using Polymerization-Based Amplification," *Anal. Bioanal. Chem.* 392:167-175.

Hansen et al. (2009) "Visual, Base-Specific Detection of Nucleic Acid Hybridization Using Polymerization-Based Amplification," *Anal. Biochem.* 386:285-287.

Hansen et al. (Dec. 1, 2007) "Visual Detection of Labeled Oligonucleotides Using Visible Light-Polymerization-Based Amplification," *Biomacromolecules*, DOI 10.1021/bm700672z.

Hardiman, G. (2004) "Microarray Platforms-Comparisons and Contrasts," *Pharmacogenomics* 5:487-502.

Hoheisel et al. (Mar. 2006) "Microarray Technology: Beyond Transcription Profiling and Genotype Analysis," *Nat. Rev. Genet.* 7:200-210.

Husemann et al. (1999) "Surface Initiated Polymerization for Amplification of Self-Assembled Monolayers Patterned by Microcontact Printing," *Angew. Chem. Int. Ed.* 38(5):647-649.

International Search Report Corresponding to International Application No. PCT/US04/029733, Mailed Mar. 24, 2005, 3 pages.

International Search Report Corresponding to International Application No. PCT/US05/08807, Mailed May 2, 2006, 6 pages.

Jarvius et al. (Web Release Aug. 23, 2006) "Digital Quantification Using Amplified Single-Molecule Detection," *Nature Methods* 3(9):725-727.

Jenison et al. (Jan. 2001) "Interference-Based Detection of Nucleic Acid Targets on Optically Coated Silicon," *Nat. Biotechnol.* 19:62-65.

Jenison et al. (2001) "Silicon-Based Biosensors for Rapid Detection of Protein or Nucleic Acid Targets," *Clin. Chem.* 47(10):1894-1900.

Johnson et al. (2009) "Characterization of the Assaying Methods in Polymerization-Based Amplification of Surface Biomarkers," *Aust. J. Chem.* 62:877-884.

Johnson et al. (Apr. 12, 2010) "Photoinitiator Nucleotide for Quantifying Nucleic Acid Hybridization," *Biomacromolecules* 11(4):1133-1138.

Kern et al. (1996) "An Enhanced-Sensitivity Branched-DNA Assay for Quantification of Human Immunodeficiency Virus Type 1 RNA in Plasma," *J. Clin. Microbiol.* 34:3196-3203.

Kizilel et al. (Web Release Nov. 13, 2006) "Mathematical Model for Surface-Initiated Photopolymerization of Poly(ethylene glycol) Diacrylate," *Macromol. Theory Simul.* 15:686-700.

Kizilel et al. (Web Release Sep. 12, 2005) "Sequential Formation of Covalently Bonded Hydrogel Multilayers Through Surface Initiated Photopolymerization," *Biomaterials* 27:1209-1215.

Kizilel et al. (Web Release Aug. 27, 2004) "Photopolymerization of Poly(ethylene Glycol) Diacrylate on Eosin-Functionalized Surfaces," *Langmuir* 20:8652-8658.

(56) References Cited

OTHER PUBLICATIONS

Li et al. (2001) "Typing and Subtyping Influenza Virus Using DNA Microarrays and Multiplex Reverse Transcriptionase PCR," *J. Clin. Microbiol.* 39(2):696-704.

Li et al. (Web Release Han 23, 2006) "BEAMing up for Detection and Quantification of Rare Sequence Variants," *Nature Methods* 3(2):95-97.

Lizardi et al. (1998) "Mutation Detection and Single-Molecule Counting Using Isothermal Rolling-Circle Amplification," *Nat. Genet.* 19:225-232.

Lou et al. (2006) "Radical Polymerization in Biosensing," *Anal. Bioanal. Chem.* 386:525-531.

Lou et al. (Jan. 2006) "DNA-Accelerated Atom Transfer Radical Polymerization on a Gold Surface," Langmuir, 22, 2640-2646.

Lou et al. (Jul. 2005) "Detection of DNA Point Mutation by Atom Transfer Radical Polymerization," *Anal. Chem.* 77, 4698-4705.

Michel et al. (Feb. 2007) "Optical Study of DNA Surface Hybridization Reveals DNA Surface Density as a Key Parameter for Microarray Hybridization Kinetics," *Biophys. J.* 92:999-1004.

Nallur et al. (2001) "Signal Amplification by Rolling Circle Amplification on DNA Microarrays," *Nuc. Acids Res.* 29:E118.

Park et al. (Feb 2002) "Array-Based Electrical Detection of DNA with Nanoparticle Probes," *Science* 295:1503-1506.

Park et al. (Web Release Nov. 2005) "Fluorescence-Based Assay Formats and Signal Amplification Strategies for DNA Microarray Analysis," *Chem. Eng. Sci.* 61:954-965.

Peterson et al. (2001) "The Effect of Surface Probe Density on DNA Hybridization," *Nuc. Acids Res.* 29(24):5163-5168.

Peterson et al. (2002) "Hybridization of Mismatched or Partially Matched DNA at Surfaces," *J. Am. Chem. Soc.* 124:14601-14607.

Revzin et al. (2001) "Fabrication of Poly(ethylene glycol) Hydrogel Microstructures Using Photolithography," *Langmuir* 17:5440-5447.

Risberg, E. (Apr. 2003) "Gene Chip Helps Identify Cause of Mystery Illness," *USA Today* Jun. 15, 2003.

Satoh et al. (Web Release Dec. 2004) "Photografting of Polymers onto Nanosized Silica Surface Initiated by Eosin Moieties Immobilized onto the Surface," *J.Polym. Sci., Part A: Polym. Chem.* 43:600-606.

Schena, M. (2003) *Microarray Analysis*, John Wiley and Sons, New Jersey, pp. 8,117,151,153,154.

Sengupta et al. (Oct. 2003) "Molecular Detection and Identification of Influenza Viruses by Oligonucleotide Microarray Hybridization," *J. Clin. Microbiol.* 41(10):4542-4550.

Shah et al. (2000) "Using Atom Transfer Radical Polymerization to Amplify Monolayers of Initiators Patterned by Microcontact Printing into Polymer Brushed for Pattern Transfer," *Macromol.* 33:597-605.

Sigma, FITC Product Description Sheets (2008).

Sikes et al. "Antigen Detection Using Polymerization-Based Amplification," *Lab on a Chip* 9(5):653-656, Dec. 2008.

Sikes et al. (Oct. 2007) "Using polymeric materials to generate an amplified response to molecular recognition events", *Nature Materials* doi:10.1038/n mat2042.

Stears et al. (2000) "A Novel, Sensitive Detection System for High-Density Microarrays Using Dendrimer Technology," *Physiol. Genomics* 3:93-99.

Supplementary European Search Report, Corresponding to European Application No. EP 04 81 6118, Completed Apr. 14, 2008, 1 page.

Supplementary European Search Report, Corresponding to European Application No. EP 05 72 5765, Completed Apr. 14, 2008, 1 page.

Tan et al. (2004) "Bionanotechnology Based on Silica Nanoparticles," *Med. Res. Rev.* 24:621-638.

Taton et al. (2000) "Scanometric DNA Array Detection with Nanoparticle Probes," *Science* 289:1757-1760.

Thaxton et al. (Web Release Oct. 2005) "Gold Nanoparticle Probes for the Detection of Nucleic Acid Targets," *Clinica Chimica Acta* 363:120-126.

Townsend et al. (Aug. 2006) "Experimental Evaluation of the FluChip Diagnostic Microarray for Influenza Virus Surveillance," *J. Clin. Microbiol.* 44(8):2863-2871.

Tsongalis et al. (Sep. 2006) "Branched DNA Technology in Molecular Diagnostics," *Am. J. Clinical Pathology.* 126:448-453.

Vernet, G. (2001) "DNA-Chip Technology and Infectious Diseases," *Virus Res.* 82:65-71.

Wang et al (Sep. 2002) "Microarray Based Detection and Genotyping of Viral Pathogens," *Proc. Nat. Acad. Sci. USA* 99(24):15687-15692.

Weber et al. (Jan. 1, 1959) "Determination of the Absolute Quantum Yield of Fluorescent Solutions," *Trans. Faraday Soc.* :646-655.

Written Opinion Corresponding to International Application No. PCT/US04/029733, Mailed Mar. 24, 2005, 3 pages.

Written Opinion Corresponding to International Application No. PCT/US05/08807, Mailed May 2, 2006, 6 pages.

Xu et al. (2001) "Microfabricated Disposable DNA Sensors Based on Enzymatic Amplification Electrochemical Detection," *Electroanalysis* 13(10):882-887.

Zhang et al. (1998) "Amplification of Target-Specific, Ligation-Dependent Circular Probe," *Gene* 211:277-285.

Zhong et al. (Sep. 30, 2003) "Single-Nucleotide Polymorphism Genotyping on Optical Thin-Film Biosensor Chips," *Proc. Nat. Acad. Sci.* 100(20):11559-11564.

Eaton, D.F. "Dye Sensitized Photopolymerization," in Volman et al., Advances in photochemistry (John Wiley and Sons, 1986) vol. 13, Chapter 6 (pp. 427-487).

Moad, G. and Solomon, D.H., The Chemistry of Radical Polymerization, ,Elsevier, 2006, Title page and pp. 102-103.

* cited by examiner

Figure 7a
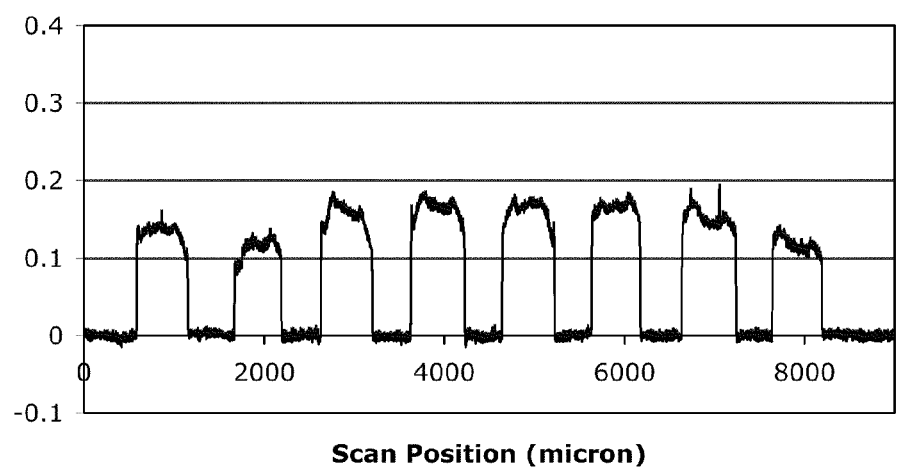
Scan Position (micron)
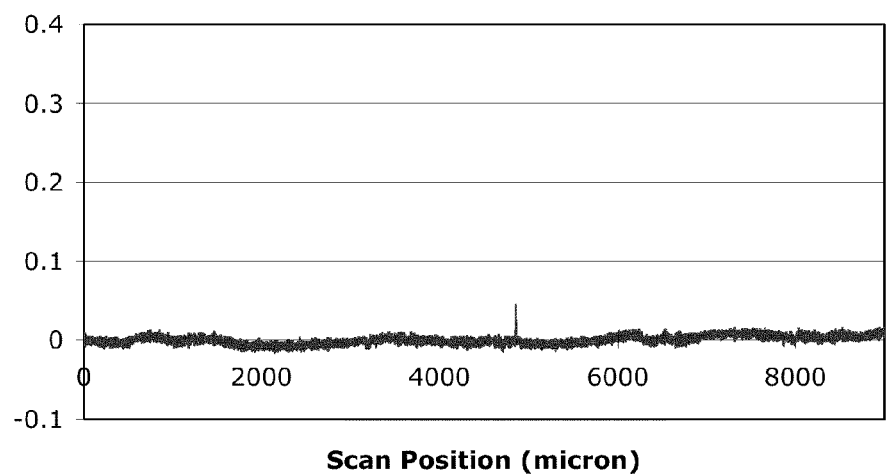
Scan Position (micron)
Figure 7b

USE OF PHOTOPOLYMERIZATION FOR AMPLIFICATION AND DETECTION OF A MOLECULAR RECOGNITION EVENT

CROSS-REFERENCE TO RELATED APPLICATIONS

This application is a continuation of U.S. application Ser. No. 12/099,560, filed Apr. 8, 2008, which is a continuation-in-part of U.S. application Ser. No. 11/372,485, filed Mar. 9, 2006. U.S. Ser. No. 12/099,560 also claims the benefit of U.S. provisional applications 60/988,563, filed Nov. 16, 2007 and 60/982,992, filed Oct. 26, 2007. U.S. application Ser. No. 11/372,485 is a continuation-in-part of International Application serial number PCT/US2004/029733, filed Sep. 9, 2004, and claims the benefit of U.S. provisional application Ser. No. 60/662,313, filed Mar. 16, 2005; International Application PCT/US2004/029733 claims the benefit of U.S. provisional application Ser. No. 60/501,755, filed on Sep. 9, 2003,. All of these applications are hereby incorporated by reference to the extent not inconsistent with the disclosure herein.

ACKNOWLEDGEMENT OF GOVERNMENT SUPPORT

This invention was made at least in part with support from the National Institutes of Health under grant numbers NIH HG003100, R41 A1060057 and SGER 0442047, the US Air Force under grant number AFOSR F49620-02-1-0042 and the US Air Force under grant number AFOSR F49620-02-1-0042. The United States Government has certain rights in this invention.

BACKGROUND OF THE INVENTION

This invention is in the field of detection of molecular recognition events, in particular use of photopolymerization for amplification and detection of these events.

A variety of methods exist for detection of molecular recognition events. Detection of molecular recognition events such as DNA hybridization, antibody-antigen interactions, and protein-protein interactions becomes increasingly difficult as the number of recognition events to be detected decreases. Of particular interest are molecular recognition events between a target and a probe.

One approach to the problem is to increase the number of recognition events taking place. For example, polymerase chain reaction (PCR) increases the number of copies of DNA or RNA to be detected. Other molecular biology techniques which increase the number of copies of DNA or RNA to be detected include reverse transcription polymerase chain reaction (RT-PCR), strand displacement amplification, and Eberwine linear amplification.

Another approach is to amplify the signal due to each molecular recognition event. For example, DNA detection methods based on oligonucleotide-modified particles have been reported (U.S. Pat. Nos. 6,740,491, 6,777,186, 6,773,884, 6,767,702, 6,759,199, 6,750,016, 6,730,269, 6,720,411, 6,720,147, 6,709,825, 6,682,895, 6,673,548, 6,667,122, 6,645,721, 6,610,491, 6,582,921, 6,506,564, 6,495,324, 6,417,340 and 6,361,944 and Park, S.-J. et al, 2002, Science, 295,5559, 1503-1506). U.S. Pat. No. 6,602,669 relates to silver staining nanoparticles.

DNA detection methods based on branched DNA have also been reported (U.S. Pat. Nos. 5,681,702, 5,597,909, 5,580,731, 5,359,100, 5,124,246, 5,545,730, 5,594,117, 5,571,670, 5,594,118, 5,681,697, 5,591,584, 5,571,670, 5,624,802, 5,635,352, and 5,591,584. The branched DNA assay is a solution phase assay that involves a number of probe oligonucleotides that bind to multiple sites on the target viral RNA. Detection is possible because each hybridization event is accompanied by the binding of a fluorophore (Kern, D., Collins, M., Fultz, T., Detmer, J., Hamren, S., Peterkin, J., Sheridan, P., Urdea, M., White, R., Yeghiazarian, T., Todd, J. (1996) "An Enhanced-sensitivity Branched-DNA Assay for Quantification of Human Immunodeficiency Virus Type 1 RNA in Plasma" Journal of Clinical Microbiology 34:3196-3203). The synthetic effort required for this assay is relatively large:

multiple probes are designed for each RNA of interest, and the assay depends on the binding of these probes to multiple preamplifier and amplifier molecules that also must be designed and synthesized.

Dendrimer-based DNA detection methods have also been reported (U.S. Pat. Nos. 5,710,264, 5,175,270, 5,487,973, 5,484,904 and Stears, R. et al., 2000, Physiol. Genomics 3: 93-99). Dendrimers are complexes of partially double-stranded oligonucleotides, which form stable, spherical structures with a determined number of free ends. Specificity of the dendrimer detection is accomplished through specific binding of a capture oligonucleotide on a free arm of the dendrimer. Other arms of the dendrimer are labeled for detection. This method does not require enzymes and can produce amplification of 300-400.

Tyramide signal amplification is reported in U.S. Pat. Nos. 6,593,100 and 6,372,937.

Rolling circle amplification has been described in the scientific literature (Baner et al. (1998) Nuc. Acids Res. 26:5073-5078; Barany, F. (1991) Proc. Natl. Acad. Sci. USA 88:189-193; Lizardi et al. (1998), Nat. Genet. 19:225-232; Zhang et al., Gene 211:277 (1998); and Daubendiek et al., Nature Biotech. 15:273 (1997)). Rolling circle amplification is capable of detecting as few as 150 molecules bound to a microarray (Nallur, G., Luo, C., Fang, L., Cooley, S., Dave, V., Lambert, J., Kukanskis, K., Kingsmore, S., Lasken, R., Schweitzer, B. (2001) "Signal Amplification by Rolling Circle Amplification on DNA Microarrays" *Nucleic Acids Research* 29:E118). The main drawback to RCA is the necessity of DNA polymerase.

Ligase chain reaction is reported in U.S. Pat. Nos. 5,185,243 and 5,573,907.

Cycling probe technology is reported in U.S. Pat. Nos. 5,011,769, 5,403,711, 5,660,988, and 4,876,187.

Microfabricated disposable DNA sensors based on enzymatic amplification electrochemical detection was reported by Xu et al. (Xu et al., 2001, Electoanalysis, 13(10), 882-887).

Surface initiated polymerization from surface confined initiators has been reported. Biesalski et al. report poly(methyl methacrylate) brushes grown in situ by free radical polymerization from an azo-initiator monolayer covalently bound to the surface (Biesalski, M. et al., (1999), J. Chem. Phys., 111(15), 7029). Surface initiated polymerization for amplification of patterned self-assembled monolayers by surface-initiated ring opening polymerization (Husemann, M. et al., Agnewandte Chemie Int. Ed. (1999), 38(5) 647-649) and atom transfer radical polymerization (Shah, R. R. et al., (2000), Macromolecules, 33, 597-605) has been also reported.

WO/2007/095464 to Kuck reports signal amplification of biorecognition events using photopolymerization in the presence of air.

DNA microarrays, or biochips, represent promising technology for accurate and relatively rapid pathogen identification (Wang, D., Coscoy, L., Zylberberg, M., Avila, P. C., Boushey, H. A., Ganem, D., DeRisi, J. L. (2002) "Microarray Based Detection and Genotyping of Viral Pathogens," *PNAS*, 99(24), 15687-15692). Anthony et al. recently demonstrated rapid identification of 10 different bacteria in blood cultures using a BioChip (Anthony, R. M., Brown, T. J., French, G. L. (2000) "Rapid Diagnosis of Bacteremia by Universal Amplification of 23S Ribosomal DNA Followed by Hybridization to an Oligonucleotide Array" *Journal of Clinical Microbiology* 38:781-788). The microarray assay was conducted in ~4 hrs. The approach utilized universal primers for PCR amplification of the variable region of bacterial 23s ribosomal DNA, and a 3×10 array of 30 unique capture sequences. This work demonstrates an important aspect of BioChip platforms—the capability to screen for multiple pathogens simultaneously. DeRisi and co-workers demonstrated a "virus chip" that contained sequences for hundreds of viruses, including many that cause respiratory illness (Wang et al., 2002). This chip proved useful in identifying the corona virus associated with SARS (Risberg, E. (2003) "Gene Chip Helps Identify Cause of Mystery Illness," USA Today (Jun. 18, 2003)). Evans and co-workers have demonstrated that a DNA microarray could be used for typing and sub-typing human influenza A and B viruses (Li, J., Chen, S., & Evans, D. H. (2001) "Typing and Subtyping Influenza Virus Using DNA Microarrays and Multiplex Reverse Transcriptase PCR" *Journal of Clinical Microbiology* 39:696-704). In both the DeRisi and Evans work PCR technology was used to amplify the genetic material for capture and relatively expensive fluorescent labels (~$50 in labels per chip) were used to generate signals from positive spots. Townsend et al. report experimental evaluation of a FluChip diagnostic microarray for influenza virus surveillance (Townsend, M. et al., J. Clinical Microbiology, August 2006, 44(8), 2863-2871). Dawson et al. report DNA microarrays that target the matrix gene segment of influenza A (MChip) (Dawson, E. et al., October 2006, Anal. Chem, 78(22), 7610-7615; Dawson, E. et al, November 2006, Anal. Chem., 79 (1), 378-384, 2007).

There remains a need in the art for relatively inexpensive labeling and signal amplification methods for molecular recognition events which do not require the use of enzymes for amplification. These methods would be useful in combination with DNA microarrays.

SUMMARY OF THE INVENTION

In an embodiment, the invention provides methods to detect molecular recognition events, in particular a relatively small number of molecular recognition events. The methods of the invention are based on amplification of the signal due to each molecular recognition event, rather than amplification of the number of molecular recognition events taking place. The present invention can limit or eliminate the need for techniques which increase the number of recognition events taking place, including PCR and techniques involving culturing of bacteria. The present invention can replace PCR and RT-PCR techniques for microarray applications as a means to achieve acceptable signals.

In general, the methods of the invention can be used to generate and amplify a signal due to many types of molecular recognition events that can be described by the following equation:

$$A+B+\text{In} \rightarrow A-B-\text{In} \quad \text{(Eqn. 1)}$$

where A and B are the species of interest that undergo molecular recognition and In is a photoinitiator. A is the probe species and B is the target species. For a microarray, the probe A is attached to the substrate. The target species, B, and/or the photoinitiator may comprise a linking group which allows selective binding of the photoinitiator to the target or the A–B complex. As an example, the target species may comprise biotin and the initiator avidin. In an embodiment, the target species comprises one of biotin and a biotin-binding protein and the probe species comprises the other of biotin and a biotin-binding protein. Biotin-binding proteins include avidin, streptavidin, and Neutravidin (a deglycosylated form of avidin).

When the initiator comprises a linking group, Equation 1 may also be written as:

$$A+B+C-\text{In} \rightarrow A-B-C-\text{In} \quad \text{(Eqn. 2)}$$

where C comprises an entity which allows selective binding of the photoinitiator to the target or the A–B complex.

In an embodiment, the molecular recognition event occurs between a target and a probe to form a target-probe complex. The target-probe complex is labeled with a photoinitiator label which comprises a photoinitiator. In one embodiment, the photoinitiator is capable of being activated by ultraviolet (UV) light and photopolymerization is initiated by exposure to a source of UV light. In this embodiment, a co-initiator may not be required. In another embodiment, the photoinitiator is capable of being activated by visible light and photopolymerization is initiated by exposure to a source of visible light. In an embodiment, the photoinitiator is part of a two-part photoinitiator system comprising a photoinitiator and a co-initiator. In an embodiment, the photoinitiator interacts with the co-initiator to generate free-radicals upon exposure to a source of visible light.

The amplification scheme relies on the large number of propagation events that occur for each initiation event. Depending on the specific polymerization system used (light intensity, initiator concentration, monomer formulation, temperature, etc.), each initiator can lead to the polymerization of as many as $10^2$-$10^6$ monomer units. Thus, each single molecular recognition event has the opportunity to be amplified by the polymerization of up to $10^6$ or $10^7$ monomers, each of which may be fluorescent or enable detection of its presence through one of a variety of means. In other embodiments, the detectable response can be generated from as low as $10^4$, $10^5$, or $10^6$ molecular recognition events.

In an embodiment, a fluorescent polymer, a magnetic polymer, a radioactive polymer or an electrically conducting polymer can form the basis of detection and amplification. In another embodiment, a polymer gel swollen with a fluorescent solution, a magnetic solution, a radioactive solution or an electrically conducting solution can form the basis of detection and amplification. In another embodiment, a polymer containing a plurality of detectable particles can form the basis of detection and amplification. In an embodiment, the particles may be detected on the basis of fluorescence, magnetic properties, radioactivity, electrical conductivity, or light absorption/color.

In another embodiment, the quantity of polymer formed is sufficient to allow visual detection of polymer formation. In this embodiment, the polymer need not be fluorescent, magnetic, radioactive or electrically conducting. This embodiment can be achieved through a synergistic combination of reduction of oxygen content in the polymer precursor solution by purging, utilization of a photoinitiator label with an appropriate ratio of initiator to molecular recognition agent, and the identification of the appropriate exposure time. Without wishing to be bound by any particular belief, it is believed that a process having all these attributes can yield much higher degrees of amplification and enable better contrast than is possible with a process having only one of these attributes.

In an embodiment, the invention provides a method for amplifying a molecular recognition interaction between a target and a probe comprising the steps of:
- a. contacting the target with the probe under conditions effective to form a target-probe complex;
- b. removing target not complexed with the probe;
- c. contacting the target-probe complex with a photoinitiator label under conditions effective to attach the photoinitiator label to the target-probe complex;
- d. removing photoinitiator label not attached to the target-probe complex;
- e. contacting the photoinitiator-labeled target-probe complex with a polymer precursor solution;
- f. exposing the photoinitiator-labeled target-probe complex and the polymer precursor solution to light, thereby forming a polymer; and
- g. detecting the polymer formed, thereby detecting an amplified target-probe interaction.

In an embodiment, the invention provides a method for amplifying a molecular recognition interaction between a target and a probe comprising the steps of:
- a. contacting the target with the probe under conditions effective to form a target-probe complex;
- b. removing target not complexed with the probe;
- c. contacting the target-probe complex with a photoinitiator label under conditions effective to attach the photoinitiator label to the target-probe complex;
- d. removing photoinitiator label not attached to the target-probe complex;
- e. contacting the photoinitiator-labeled target-probe complex with a polymer precursor solution;
- f. exposing the photoinitiator-labeled target-probe complex and the polymer precursor solution to light, thereby forming a polymer; and
- g. detecting the polymer formed, thereby detecting an amplified target-probe interaction, wherein the photoinitiator label is a macroinitiator and the oxygen content of the polymer precursor solution during light exposure is sufficiently low and the time of light exposure is sufficiently long that the polymer forms in sufficient quantities to allow visual detection.

In another embodiment, the invention provides methods for identification of a target species based on its molecular interaction with an array of different probe species, each probe species being attached to a solid substrate at known locations.

In the methods of the invention, if the target species undergoes a molecular recognition reaction with a probe, the probe will be labeled with a polymer. Detection of the polymer-labeled probes allows identification of which probes have undergone the molecular recognition reaction and therefore identification of the target.

In an embodiment, the invention provides a method for identifying a target comprising the steps of:
- a. providing a probe array comprising a plurality of different probes, wherein the probes are attached to a solid substrate at known locations;
- b. contacting the probe array with the target under conditions effective to form a target-probe complex;
- c. removing target not complexed with the probe;
- d. contacting the target-probe complex with a photoinitiator label under conditions effective to attach the label to the target-probe complex;
- e. removing photoinitiator label not attached to the target-probe complex;
- f. contacting the photoinitiator-labeled target-probe complex with a polymer precursor solution;
- g. exposing the photoinitiator-labeled target-probe complex and the polymer precursor to light, thereby forming a polymer; and
- h. detecting the polymer formed, wherein the polymer location indicates the probe which forms a target-probe complex with the target, thereby identifying the target.

In an embodiment, the invention provides a method for identifying a target comprising the steps of:
- a. providing a probe array comprising a plurality of different probes, wherein the probes are attached to a solid substrate at known locations;
- b. contacting the probe array with the target under conditions effective to form a target-probe complex;
- c. removing target not complexed with the probe;
- d. contacting the target-probe complex with a photoinitiator label under conditions effective to attach the label to the target-probe complex;
- e. removing photoinitiator label not attached to the target-probe complex;
- f. contacting the photoinitiator-labeled target-probe complex with a polymer precursor solution;
- g. exposing the photoinitiator-labeled target-probe complex and the polymer precursor solution to light, thereby forming a polymer; and
- h. detecting the polymer formed, wherein the polymer location indicates the probe which forms a target-probe complex with the target, thereby identifying the target, wherein the photoinitiator label is a macroinitiator and the oxygen content of the polymer precursor solution during light exposure is sufficiently low and the time of light exposure is sufficiently long that the polymer forms in sufficient quantities to allow visual detection.

In another embodiment, the invention provides a method for identifying a target comprising the steps of providing a probe array comprising a plurality of different probes, wherein the probes are attached to a solid substrate at known locations; the method comprising the steps of:
- a. contacting the target with the probe array under conditions effective to form a target-probe complex;
- b. removing target not complexed with the probe;
- c. contacting the target-probe complex with a photoinitiator label under conditions effective to attach the photoinitiator label to the target-probe complex, the photoinitiator label comprising a photoinitiator capable of being activated by exposure to UV light;
- d. removing photoinitiator label not attached to the target-probe complex;
- e. contacting the photoinitiator-labeled target-probe complex with a polymer precursor solution;
- f. exposing the photoinitiator-labeled target-probe complex and the polymer precursor solution to UV light, thereby forming a polymer; and
- g. detecting the polymer formed, wherein the location of the polymer formed indicates the probe which forms a target-probe complex with the target, thereby identifying the target and the oxygen content of the polymer precursor solution during step f) is limited by contacting the polymer precursor solution with a purge gas prior to step e), during step e), during step f), or combinations thereof.

In another embodiment, the invention provides a method for identifying a target comprising the steps of providing a probe array comprising a plurality of different probes, wherein the probes are attached to a solid substrate at known locations; the method comprising the steps of:
a. contacting the target with the probe array under conditions effective to form a target-probe complex;
b. removing target not complexed with the probe;
c. contacting the target-probe complex with a photoinitiator label under conditions effective to attach the photoinitiator label to the target-probe complex, the photoinitiator label comprising a photoinitiator capable of being activated by exposure to visible light;
d. removing photoinitiator label not attached to the target-probe complex;
e. contacting the photoinitiator-labeled target-probe complex with a polymer precursor solution comprising a polymer precursor and a co-initiator;
f. exposing the photoinitiator-labeled target-probe complex and the polymer precursor solution to visible light, thereby forming a polymer; and
g. detecting the polymer formed,
wherein the location of the polymer formed indicates the probe which forms a target-probe complex with the target, thereby identifying the target and the oxygen content of the polymer precursor solution during step f) is limited by contacting the polymer precursor solution with a purge gas prior to step e), during step e), during step f), or combinations thereof.

The methods of the invention can be used to identify target species using DNA microarrays, also commonly referred to as DNA chips or BioChips, to provide the probe array. In an embodiment, the DNA microarray may be an array which allows identification and strain analysis for one or more genera of influenza virus.

In one aspect of the invention, observation of polymer formation can be used as a qualitative indicator of the presence or absence of the target. The threshold for such a yes/no response is tunable. For example, for probes attached to a substrate the threshold can be tuned by adjusting the probe concentration on the substrate surface.

In another aspect of the invention, the amount of target can be determined quantitatively. In an embodiment, the amount of target can be determined through measurement of a detectable characteristic of the polymer formed. Suitable detectable characteristics include, but are not limited to, the amount of polymer formed, the thickness of polymer formed fluorescence, magnetic properties, radioactivity, electrical conductivity and adsorption. In an embodiment, the amount of target can be determined through use of a reference correlation between the amount of target (or a target test species) and the value of the detectable characteristic. For example, the amount of target may be determined from the thickness of the polymer formed when the probe molecules are attached to a substrate in "spots" of known size. In this case, the correlation referred to can relate polymer film thickness to concentration of target or to a test species.

In another embodiment, the amount of target can be determined through measurement of a detectable characteristic of one or more additional detectable components contained within the polymer formed. Suitable detectable components include, but are not limited to fluorescent, magnetic, radioactive, electrically conducting, or absorptive/colored particles. In an embodiment, the amount of target can be determined through use of a reference correlation between the amount of target (or a target test species) and the value of the detectable characteristic of the detectable component. For example, the amount of target may be determined from analysis of the amount of fluorescence observed from fluorescent particles incorporated into the polymer.

In another embodiment, the amount of target can be determined through analysis of the polymerization parameters required to obtain a given value for a particular characteristic of the polymer or of detectable components contained within the polymer. In an embodiment, the polymerization conditions to obtain a selected value of a detectable characteristic of the polymer can be compared to a reference correlation or other reference information. For example, the minimum time or radiation dose to obtain sufficiently thick polymer for visual observation can be used to determine the concentration of target when a calibration of visualization time versus concentration of target or test species is available.

In an embodiment, the methods of the invention provide sufficient amplification that molecular recognition can be detected without instrumentation. In another embodiment, the methods of the invention provide sufficient amplification that molecular recognition can be detected using a relatively inexpensive microarray reader or scanner which may not have the highest instrument sensitivity or resolution.

BRIEF SUMMARY OF THE FIGURES

FIG. 3A is an image of the array after polymerization; FIG. 3B shows negative control spots on the same array.

FIG. 6a shows an image of the array after polymerization with a macrophotoinitiator. FIG. 6b shows the maximum number of biotinylated oligomers present in each spot. FIG. 6c shows the minimum radiation dose delivered to each spot prior to observation of polymer formation.

FIGS. 7a and 7b illustrate profilometry scans across spots containing 3'biotin labeled capture sequences (a) and unlabeled capture sequences (b). Both rows contained capture sequences at a surface density of $10^2$ capture sequences/$\mu^2$.

DETAILED DESCRIPTION OF THE INVENTION

Figure 1:
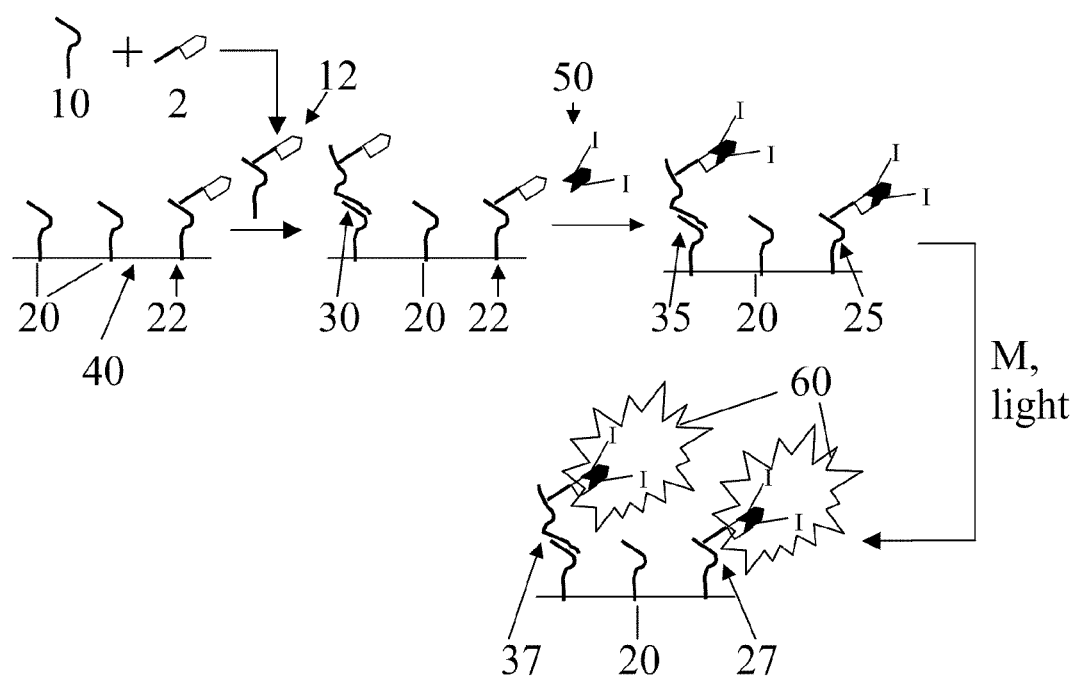
FIG. 1 schematically illustrates some of the steps in detection and amplification of hybridization using photopolymerization.

FIG. 1 is a conceptual diagram of how photopolymerization of a fluorescent monomer M is used to generate and amplify a signal from a single captured genetic target on a DNA microarray. FIG. 1 shows addition of biotin (2) to the target oligonucleotide (10) to form a biotinylated target nucleotide (12). The biotinylated target nucleotide (12) is hybridized to a complementary probe (20), forming a target-probe complex (30) on the surface of the microarray (40). The microarray shown in FIG. 1 contains a biotin-labeled probe (22) which acts as a positive control. After hybridization, the microarray is exposed to a photoinitiator label (50), initiator-functionalized avidin, which interacts with the biotinylated target oligonucleotide (12) and control probe (22) to form an initiator-labeled target-probe complex (35) and an initiator-labeled positive control probe (25). The microarray surface is then exposed to a fluorescent monomer (M) under the appropriate initiation conditions. In the presence of light and a fluorescent monomer (represented by M in FIG. 1), a polymerization reaction occurs from sites on the surface where targets have been captured by the probe DNA, forming a polymer-labeled target-probe complex (37) and a polymer-labeled positive control probe (27). In FIG. 1, the polymer label is denoted by (60). Ideally, since initiators are not bound to sites where hybridization has not occurred, polymerization does not occur from those sites. For brevity, FIG. 1 omits several steps which are typically used in the process, including removal of uncomplexed target material prior to exposure of the microarray to initiator functionalized avidin, removal of initiator functionalized avidin not attached to the target-probe complex, and removal of unpolymerized monomer prior to detection.

Although FIG. 1 illustrates hybridization of complementary DNA to a DNA microarray as a specific example, the detection and amplification scheme generalizes to many other types of molecular recognition events. Agents capable of participating in molecular recognition events include, but are not limited to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. In different embodiments, the detection and amplification scheme can be used to detect and amplify the molecular recognition interaction between nucleic acids, an antibody and an antigen, and a first and a second protein. Microarrays can be used to detect hybridization as well as protein-protein interactions, protein drug binding, and enzymatic catalysis (Schena, M., "Microarray Analysis, (2003) John Wiley & Sons, New Jersey, p. 153). As used herein, molecular recognition interactions are those in which the probe recognizes and selectively binds a target, resulting in a target-probe complex. Molecular recognition interactions also involve the formation of noncovalent bonds between the two species. The binding occurs between specific regions of atoms (molecular domains) on the probe species which have the characteristic of binding or attaching specifically to unique molecular domains on specific target species. Molecular recognition interactions can also involve responsiveness of one species to another based on the reciprocal fit of a portion of their molecular shapes.

The target and probe are two species of interest which undergo molecular recognition. The target may also be referred to as a ligand. The probe may also be referred to as a receptor. In an embodiment, at least some characteristics of the probe are known. In an embodiment, the probe is an oligonucleotide whose sequence is known or partially known. In other embodiment, the sequence of the probe may not be known, but it is known to be complementary to a possible target species. Typically, the probe will be selected so that it is capable of selected recognition with the known or suspected identity of the target. In some cases a single probe can be used to detect the presence of a target. In other cases more than one probe will be necessary to detect the presence of or identify a target.

In order for molecular interaction between the target and the probe to identify the target, the molecular interaction between the target and the probe must be sufficiently specific. For hybridization, the selectivity is a measure of the specificity of the molecular recognition event. "Selectivity" or "hybridization selectivity" is the ratio of the amount of hybridization (i.e., number of second nucleic acids hybridized) of fully complementary hybrids to partially complementary hybrids, based on the relative thermodynamic stability of the two complexes. For the purpose of this definition it is presumed that this ratio is reflected as an ensemble average of individual molecular binding events. Selectivity is typically expressed as the ratio of the amount of hybridization of fully complementary hybrids to hybrids having one base pair mismatches in sequence. Selectivity is a function of many variables, including, but not limited to,: temperature, ionic strength, pH, immobilization density, nucleic acid length, the chemical nature of the substrate surface and the presence of polyelectrolytes and/or other oligomers immobilized on the substrate or otherwise associated with the immobilised film.

For hybridization, the homology of the target and probe molecules influences whether hybridization occurs. Cross-hybridization can occur if the sequence identity between the target and the probe is greater than or equal to about 70% (Schena, M., "Microarray Analysis, (2003) John Wiley & Sons, New Jersey, p. 151).

In an embodiment, either the target or the probe is a nucleic acid. In an embodiment, both the target and the probe are a single stranded nucleic acid. In an embodiment, the probe is an oligonucleotide, a relatively short chain of single-stranded DNA or RNA. "Nucleic acid" includes DNA and RNA, whether single or double stranded. The term is also intended to include a strand that is a mixture of nucleic acids and nucleic acid analogs and/or nucleotide analogs, or that is made entirely of nucleic acid analogs and/or nucleotide analogs and that may be conjugated to a linker molecule.

"Nucleic acid analogue" refers to modified nucleic acids or species unrelated to nucleic acids that are capable of providing selective binding to nucleic acids or other nucleic acid analogues. As used herein, the term "nucleotide analogues" includes nucleic acids where the internucleotide phosphodiester bond of DNA or RNA is modified to enhance biostability of the oligomer and "tune" the selectivity/specificity for target molecules (Uhlmann, et al., (1990), Angew. Chem. Int. Ed. Eng., 90: 543; Goodchild, (1990), J. Bioconjugate Chem., I: 165; Englisch et al., (1991), Angew, Chem. Int. Ed. Eng., 30: 613). Such modifications may include and are not limited to phosphorothioates, phosphorodithioates, phosphotriesters, phosphoramidates or methylphosphonates. The 2'-O-methyl, allyl and 2'-deoxy-2'-fluoro RNA analogs, when incorporated into an oligomer show increased biostability and stabilization of the RNA/DNA duplex (Lesnik et al., (1993), Biochemistry, 32: 7832). As used herein, the term "nucleic acid analogues" also include alpha anomers ($\alpha$-DNA), L-DNA (mirror image DNA), 2'-5' linked RNA, branched DNA/RNA or chimeras of natural DNA or RNA and the above-modified nucleic acids. For the purposes of the present invention, any nucleic acid containing a "nucleotide analogue" shall be considered as a nucleic acid analogue. Backbone replaced nucleic acid analogues can also be adapted to for use as immobilized selective moieties of the present invention. For purposes of the present invention, the peptide nucleic acids (PNAs) (Nielsen et al., (1993), Anti-Cancer Drug Design, 8: 53; Engels et al., (1992), Angew, Chem. Int. Ed. Eng., 31: 1008) and carbamate-bridged morpholino-type oligonucleotide analogs (Burger, D. R., (1993), J. Clinical Immunoassay, 16: 224; Uhlmann, et al., (1993), Methods in Molecular Biology, 20,. "Protocols for Oligonucleotides and Analogs," ed. Sudhir Agarwal, Humana Press, NJ, U.S.A., pp. 335-389) are also embraced by the term "nucleic acid analogues". Both exhibit sequence-specific binding to DNA with the resulting duplexes being more thermally stable than the natural DNA/DNA duplex. Other backbone-replaced nucleic acids are well known to those skilled in the art and can also be used in the present invention (See e.g., Uhlmann et al., (1993), Methods in Molecular Biology, 20, "Protocols for Oligonucleotides and Analogs," ed. Sudhir Agrawal, Humana Press, NJ, U.S.A., pp. 335).

More generally, the probe and/or target can be an oligomer. "Oligomer" refers to a polymer that consists of two or more monomers that are not necessarily identical. Oligomers include, without limitation, nucleic acids (which include nucleic acid analogs as defined above), oligoelectrolytes, hydrocarbon based compounds, dendrimers, nucleic acid analogues, polypeptides, oligopeptides, polyethers, oligoethers any or all of which may be immobilized to a substrate. Oligomers can be immobilized to a substrate surface directly or via a linker molecule.

In an embodiment, the probe is DNA. The DNA may be genomic DNA or cloned DNA. The DNA may be complementary DNA (cDNA), in which case the target may be messenger RNA (mRNA). The DNA may also be an Expressed Sequence Tag (EST) or a Bacterial Artificial Chromosome (BAC). For use in hybridization microarrays, double-stranded probes are denatured prior to hybridization, effectively resulting in single-stranded probes.

DNA microarrays are known to the art and commercially available. The general structure of a DNA microarray is a well defined array of spots on an optically flat surface, each of which contains a layer of relatively short strands of DNA. As referred to herein, microarrays have a spot size less than about 1.0 mm. In most hybridization experiments, 15-25 nucleotide sequences are the minimum oligonucleotide probe length (Schena, M., "Microarray Analysis, (2003) John Wiley & Sons, New Jersey, p. 8). The substrate is generally flat glass primed with an organosilane that contains an aldehyde functional group. The aldehyde groups facilitate covalent bond formation to biomolecules with free primary amines via Schiff base interactions. After reaction the chip is cured to form a very stable array ready for hybridization.

Protein microarrays are also known to the art and some are commercially available. The general structure of protein microarrays can be similar to that of DNA microarrays, except that array spots can contain antibodies (in particular monoclonal antibodies), antigens, recombinant proteins, or peptides. For accurate measurement of binding events, surface-bound proteins must be correctly folded and fully functional (Constans, A., 2004, The Scientist, 18(15) 42). To reduce protein unfolding, the proteins can be protected by use of stabilizing buffers and/or relatively high protein concentrations (Schena, M., "Microarray Analysis, (2003) John Wiley & Sons, New Jersey, p. 154). To avoid the protein folding problem, the functional domains of interest can be arrayed rather than the whole protein, forming domain-based arrays (Constans, 2004, ibid).

In an embodiment, the target is genetic material from influenza A, B, or C. Influenza is an orthomyxovirus with three genera, types A, B, and C. The types are distinguished by the nucleoprotein antigenicity (Dimmock, N. J., Easton, A. J., Leppard, K. N. (2001) "Introduction to Modern Virology" $5^{th}$ edition, Blackwell Science Ltd., London). Influenza A and B each contain 8 segments of negative sense ssRNA. Type A viruses can also be divided into antigenic sub-types on the basis of two viral surface glycoproteins, hemagglutinin (HA) and neuraminidase (NA). There are currently 15 identified HA sub-types (designated H1 through H15) and 9 NA sub-types (N1 through N9) all of which can be found in wild aquatic birds (Lamb, R. A. & Krug, R. M., (1996) "Orthomyxoviridae: The Viruses and their Replication, in Fields Virology", B. N. Fields, D. M. Knipe, and P. M. Howley, Editors. Lippincott-Raven: Hagerstown). Of the 135 possible combinations of HA and NA, only four (H1N1, H1N2, H2N2, and H3N2) have widely circulated in the human population since the virus was first isolated in 1933. The two most common sub-types of influenza A currently circulating in the human population are H3N2 and H1N1. LI et al. describe a DNA microarray whose probes were multiple fragments of the hemagglutinin, neuraminidase, and matrix protein genes. (Li, J. et al., (2001), J. Clinical Microbio., 39(2), 696-704).

For probes bound to a substrate using aldehyde attachment chemistry, the substrate may be treated with an agent to reduce the remaining aldehydes prior to contacting the probe with the target. One suitable reducing agent is sodium borohydride $NaBH_4$. Such a treatment can decrease the amount of reaction between the monomer and the aldehyde coating on the glass, thus decreasing the amount of background signal during the detection step.

Prior to contacting the target with the probe, the target may be biotinylated to allow later attachment of at least one initiator via biotin-avidin interaction. In an embodiment, photobiotinylation reagents (Pierce, Quanta Biodesign) can be used to biotin-label the target. For example, a single-stranded target may be labeled with biotin in solution, allowed to hybridize with a single-stranded probe to form a target-probe complex, and post-hybridization exposed to UV to crosslink the biotinylated target to an aminosilated layer.

The target may also be biotinylated after formation of the target-probe complex. As an example, biotin may be attached to a target-probe complex post-hybridization via primer extension with biotin labeled deoxyribonucleotide triphosphates (dNTPs). In an embodiment, a Klenow fragment uses dsDNA as a primer for 5'→3' polymerase activity (Pastinen, T. et al, 2000, 10: 1031-1042; Erdogan, F. et al., 2001, 29(7), e36).

In an embodiment, the target may be contacted with the photoinitiator label prior to contacting the target with the probe, so long as use of a photoinitiator-labeled target does not substantially limit its participation in the desired molecular recognition event. In an embodiment, the invention provides a method for amplifying a molecular recognition interaction between a target and a probe comprising the steps of contacting a photoinitiator-labeled target with a probe under conditions effective to form a photoinitiator-labeled target-probe complex, removing target not complexed with the probe, contacting the photoinitiator-labeled target-probe complex with a polymer precursor, exposing the photoinitiator-labeled target-probe complex and the polymer precursor to light, thereby forming a polymer, and detecting the polymer formed, thereby detecting an amplified target-probe interaction.

The probe is contacted with a solution comprising the target under conditions effective to form a target-probe complex. The conditions effective to form a target-probe complex depend on the target and probe species. For ssDNA or RNA targets binding to ssDNA probes, suitable hybridization conditions have been described in the scientific literature. In an embodiment, it is sufficient to contact a solution comprising the target with the probe for about 2 hours at about 42° C. In an embodiment, this solution also comprises an agent, such as a crowding agent, to limit nonspecific interactions. With reference to nucleic acid interactions, a crowding agent is an agent that interrupts nonspecific adsorption between nucleic acids that are not complementary. Formamide is one such agent to limit nonspecific interactions (Stahl, D. A., and R. Amann. 1991. Development and application of nucleic acid probes, p. 205-248. In E. Stackebrandt and M. Goodfellow (ed.), Nucleic acid techniques in bacterial systematics. John Wiley & Sons Ltd., Chichester, United Kingdom). Nonspecific interactions can also be limited by applying a blocking agent to the microarray prior to contacting the target with the probe. Suitable blocking agents are known to the art and include, but are not limited to bovine serum albumin (BSA), nonfat milk, and sodium borohydride. Detergents such as sodium lauroyl sarcosine or sodium dodecyl sulfate can also be added to aldehyde surface hybridization reactions to reduce background (Schena, M., "Microarray Analysis, (2003) John Wiley & Sons, New Jersey, p. 117). The target solution may also be contacted with the probe at higher temperatures in order to limit nonspecific interactions.

After the target is contacted with the probe, targets which have not formed target-probe complexes are removed. The unbound targets can be removed through rinsing. Water or an aqueous solution may be used for rinsing away unbound targets.

In an embodiment, the substrate surface is treated to minimize nonspecific adsorption of the photoinitiator label. If the initiator is to be attached through biotin-avidin interaction, a blocking agent can be applied to the microarray to limit nonspecific interaction of avidin. Suitable blocking agents are known to the art and include, but are not limited to, bovine serum albumin (BSA), nonfat milk and sodium borohydride. PEG-based blocking agents which react with amine functionalities are also known to the art. The blocking agent may be applied to the substrate surface prior to contact of the photoinitiator label solution with the substrate, may be supplied in the photoinitiator label solution, or both. Denhardt's solution is a commercially available solution (Sigma-Aldrich) which contains BSA and can be included in the photoinitiator label solution. In an embodiment, the array is incubated with the blocking agent for approximately 20 minutes at about room temperature.

In an embodiment, the target-probe complex is contacted with a photoinitiator label under conditions effective to attach the photoinitiator label to the target probe complex. In an embodiment, the target-probe complex is contacted with the photoinitiator label by contacting the target-probe complex with a photoinitiator label solution comprising the photoinitiator label. In an embodiment, the solvent is aqueous and the photoinitiator label is water soluble. In an embodiment, the concentration of the photoinitiator label in the solution may be selected to limit nonspecific adsorption of the photoinitiator label to the surface of a substrate.

In an embodiment, the photoinitiator label comprises a biotin-binding protein such as avidin or streptavidin and at least one photoinitiator. In an embodiment, a plurality of photoinitiators is attached to the biotin binding protein to form a polymeric photoinitiator label. In another embodiment, a polymeric photoinitiator label is formed by attaching a plurality of photoinitiators and biotin binding protein to a polymer. In an embodiment, the photoinitiators and biotin binding protein are attached to the polymer backbone, for example by attachment to subunits in the backbone. The polymer to which the photoinitiators and biotin binding protein are attached may be chemically the same or different from the polymer formed during exposure of the polymer precursor solution to light. If the target has been biotin-labeled, interaction between the biotin-binding protein and the biotin can attach the photoinitiator label to the target, and thus to the target-probe complex. In another embodiment, both the target and the photoinitiator can be labeled with biotin and then multivalent properties of avidin (which can bind four biotins) can be used to bind together the target and the photoinitiator. Information on avidin-biotin interaction is provided in Wilcheck, M., (a) Bayer, E. A. Eds. (1990) "Avidin-biotin technology" *Methods in Enzymology* 184. In an embodiment, the biotin-labeled target-probe complex is contacted with a solution comprising the photoinitiator label for about 20 minutes at room temperature.

Figure 2:
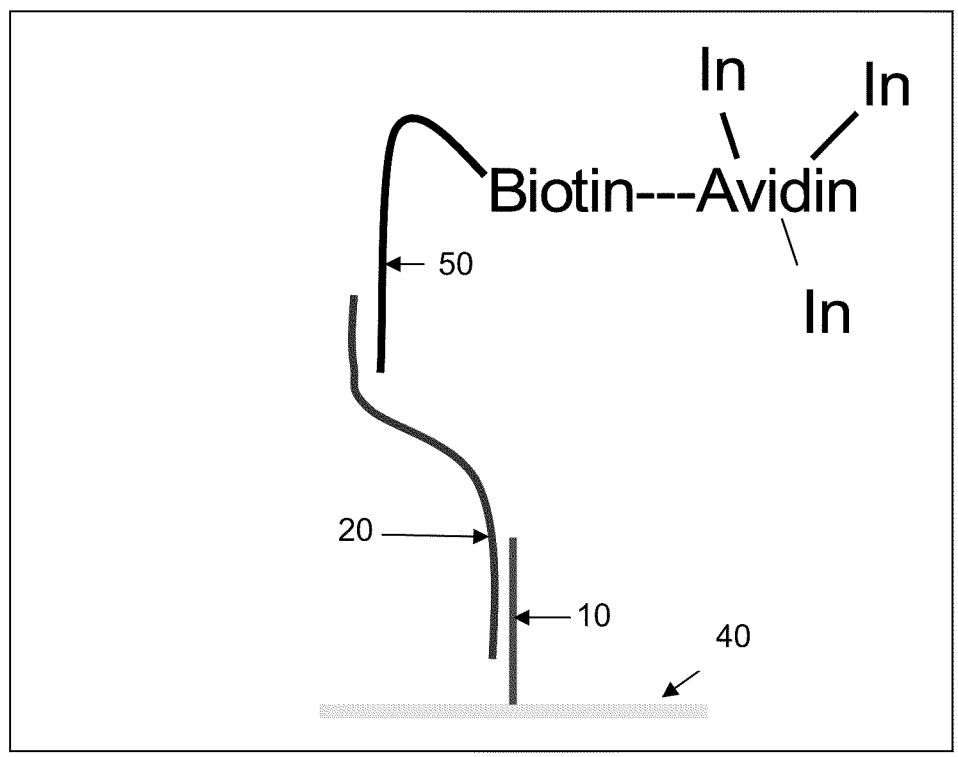
FIG. 2 illustrates an alternate two-step hybridization scheme for detection and amplification.

Another embodiment suitable for hybridization molecular recognition events is schematically illustrated in FIG. 2. In this embodiment, the photoinitiator label (50) comprises a single strand of DNA attached to at least one photoinitiator (In). The photoinitiator can be attached to the ssDNA through biotinylation of the DNA followed by interaction with avidin or streptavidin with at least one photoinitiator attached. In another embodiment, photoinitiators are coupled directly to the end of the oligonucleotide label sequences. Oligonucleotides with 5' amine modifications can be purchased and the reaction conditions in Scheme 2 (EDC coupling) used to form a peptide bond between this amine and the carboxylic acid group of the initiator. The product can be purified by HPLC. During the photopolymerization reaction, the target anchors the initiator, through the label sequence, to the microarray spot. If target viral RNA will not tolerate the presence of the fluorescent monomer and UV light, it is possible to connect the label sequence to the probe oligonucleotide via a treatment with ligase prior to exposure to the photopolymerization reaction conditions. Another method that avoids the use of an enzyme is to place pendant photocrosslinkable groups on the probe oligonucleotide and the label sequence. If, however, the polymerization reaction is fast when compared with the timescale of diffusion, these steps will not be necessary even if the target genetic material detaches from the capture strand.

A number of photoinitiators are known to the art. Photoinitiators that are useful in the invention include those that can be activated with light and initiate polymerization of the polymer precursor. In an embodiment, the photoinitiator is water soluble. Commercially available photoinitiators, for example Irgacure 2959 (Ciba), can be modified to improve their water solubility. In an embodiment, the photoinitiator is a radical photoinitiator. In another embodiment, the photoinitiator is a cationic photoinitiator. In another embodiment, the photoinitiator comprises a carboxylic acid functional group. The photoinitiator is selected to be compatible with the wavelengths of light supplied.

Photoinitiators include azobisisobutyronitrile, peroxides, phenones, ethers, quinones, acids, formates. Cationic initiators include aryldiazonium, diaryliodonium, and triarylsulfonium salts. In an embodiment, the photoinitiator is selected from the group consisting of Rose Bengal (Aldrich), Darocur or Irgacure 2959 (2-hydroxy-1-(4-(hydroxyethoxy)phenyl)-2-methyl-1-propanone, D2959, Ciba-Geigy), Irgacure 651 (2,2-dimethoxy-2-phenylacetophenone, 1651, DMPA, Ciba-Geigy), Irgacure 184 (1-hydroxycyclohexyl phenyl ketone, 1184, Ciba-Geigy), Irgacure 907 (2-methyl-1-(4-(methylthio)phenyl)-2-(4-morpholinyl)-1-propanone, 1907, Ciba-Geigy), Camphorquinone (CQ, Aldrich), isopropyl thioxanthone (quantacure ITX, Great Lakes Fine Chemicals LTD., Cheshire, England). CQ is typically used in conjunction with an amine such as ethyl 4-N,N-dimethylaminobenzoate (4EDMAB, Aldrich) or triethanolamine (TEA, Aldrich) to initiate polymerization.

A number of photoinitiators are known to the art which can be activated by visible light to produce free radicals. In an embodiment, the photoinitiator is part of a two-part photoinitiator system, comprising a photoinitiator and a co-initiator. In an embodiment, the photoinitiator interacts with the co-initiator to generate free-radicals upon exposure to a source of visible light. In an embodiment, the photoinitiator is a photoreducible dye. Suitable co-initiators for visible light photoinitiators are known to those skilled in the art. Use of visible light sources for photoinitiation has the attractive characteristic of requiring only a low power, inexpensive and mild excitation source. Further, use of visible light has the added advantage of eliminating unwanted bulk polymerization which can result from use of UV light. The use of visible light, rather than UV light, for photoinitiation can also expand the range of suitable monomer formulations. In an embodiment, the monomer formulation contains high concentrations of bi-functional monomers that form thick, highly crosslinked polymer that remains stable on the surface with rinsing. Formation of a surface-stable hydrogel facilitates characterization of the amplification process with film thickness and spectroscopic measurements. Finally, visible light can enable more efficient amplification due to its higher penetration capability in UV absorbent monomer formulations containing fluorescent monomers or on UV absorbent surfaces characteristic of glass biochips containing surface-bound biomolecules.

In an embodiment, the photoinitiator molecule is an eosin, a bromine derivative of fluorescein, or a derivative. In an embodiment, the photoinitiator molecule is 2',4',5',7'-tetrabromofluorescein or a derivative. In an embodiment, the photoinitiator molecule is Rose Bengal or a derivative. In different embodiments, the photoinitiator is activated by wavelengths of light between 400 and 700 nm, between 450 and 600 nm, between 400 and 500 nm, or between 500 and 600 nm. Suitable co-initiators for fluorescein derivatives include, but are not limited to, amines such as methyl diethanol amine and tetraethanol amine. In an embodiment where the photoinitiator label comprises eosin attached to streptavidin, the concentration of the photoinitiator label is 1 µg/mL or less.

Photoinitiator molecules can be attached to avidin or streptavidin by modification of avidin or streptavidin lysine residues. For photoinitiators having a carboxylic acid functional group, the carboxylic functional group of the photoinitiator can be coupled to the amine of the lysine residue in the presence of a coupling agent. The result is the formation of a peptide bond between the initiator and the protein. Suitable coupling agents are known to those skilled in the art and include, but are not limited to, EDC.

In another embodiment, a polymeric photoinitiator label is formed. Such a polymeric photoinitiator label can be formed from a polymer which can be coupled with both the photoinitiator and a molecular recognition group such as avidin or streptavidin. In an embodiment, the photoinitiator can be attached to the polymer by an ester linkage or by any other kind of linkage known to the art. In an embodiment, the avidin or streptavidin can be attached to the polymer by an amide linkage. In an embodiment, the polymer comprises carboxylic acid groups and amide groups. In an embodiment, the polymer comprises a poly(acrylic acid-co-acrylamide) backbone.

In an embodiment, a polymeric photoinitiator label can be formed from a polymer which comprises one part of a two-part photoinitiator system. The polymer is coupled to a molecular recognition group such as avidin or streptavidin. When the combination of the polymer and the second part of the initiator system is exposed to the appropriate wavelength of light, the initiator system is capable of capable of initiating polymerization of a polymer precursor. In an embodiment, one part of the two-part photoinitiator system is a tertiary amine which is part of the polymeric photoinitiator label. The other part of the photoinitiator system can be camphorquinone. (CQ) This two-part system can be activated by light of approximately 469 nm. The tertiary amine can be incorporated into the polymer label by co-polymerizing acrylic acid with a monomer comprising the tertiary amine and an acrylate group.

In an embodiment, the polymeric photoinitiator comprises sufficient photoinitiators so that it may be regarded as a macroinitiator (having many initiators present on a single molecule). The number of initiator groups per molecule or chain may vary from one chain to another. In an embodiment, the use of a macroinitiator can increase the average initiator concentration by a factor of between about 10 to about 100. In another embodiment, the average number of initiators per polymer chain is between about 100 and about 200. In another embodiment, the average number of initiators per polymer chain is between about 120 and about 160. The number of molecular recognition groups may also vary from chain to chain. In an embodiment, the average number of molecular recognition groups is between one and three. Without wishing to be bound by any particular belief, it is believed that the incorporation of too many initiator groups can lead to nonspecific interaction between the macroinitiator and the array. The molecular weight of the backbone polymer is selected to be large enough to allow attachment of the appropriate number of initiator and molecular recognition groups. For a poly(acrylic acid-co-acrylamide) backbone, the molecular weight of the backbone is preferably greater than about 50,000.

In an embodiment, the polymer backbone of the macroinitiator comprises sufficient hydrophilic monomeric units that the macroinitiator is water soluble. In an embodiment, the hydrophilic monomeric units are selected from the group consisting of ethylene glycol, acrylate, acrylate derivatives such as acrylamide and hydroxyethylacrylate, and vinyl monomers such as 1-vinyl-2-pyrolidinone. Without wishing to be bound by any particular belief, hydrophilic macroinitiator backbones are believed to limit nonspecific adsorption of the macroinitiator from aqueous solutions.

In another embodiment, the photoinitiator label comprises less than 10 photoinitiator groups. In an embodiment, the photoinitiator label includes from 2 to 9 initiator groups. In another embodiment, the photoinitiator label comprises from 2 to 3 initiator groups. In another embodiment, the average number of initiator groups is from 2 to 3. In an embodiment, the amount of polymer formed using such a photoinitiator label can be used as a quantitative measure of the number of molecular recognition events In an embodiment, the photoinitiator label is selected so that the polymer produced through photopolymerization is bound to the target with sufficient strength that is not easily removed with rinsing (if the target is bound to a surface, the polymer can in turn be bound to the surface). In an embodiment, the photoinitiator molecule is selected so that the polymer formed is attached to the target through termination between surface stabilized radicals from the photoinitiator and bulk radicals present on the polymer chains. For example, it has been suggested that eosin radicals are responsible for strong attachment of polyethylene glycol (PEG) diacrylate gels onto substrate surfaces (Kizilel, S.; Perez-Luna, V. H.; Teymuor F. *Macromolecular Theory and Simulations* 2006, 15, 686-700). In one embodiment, the photoinitiator molecule is fluorescein or a fluorescein derivative such as eosin.

After contact of the photoinitiator label with the target-probe complex, unattached photoinitiator is removed. In an embodiment, photoinitiator label not attached to the target-probe complex is sufficiently removed to reduce any signal resulting from non-specific adsorption to acceptable levels. The excess photoinitiator label may be removed by removal of the photoinitiator label solution. When the probe is attached to a solid substrate, the substrate may also be rinsed to remove the excess. Unattached photoinitiator may be removed by rinsing with water or an aqueous solution. The rinse may be a room temperature aqueous solution, such as a TNT solution (1M NaCl, 0.1M Tris, 0.1 wt % Tween 20). The rinse may also be at higher temperature, such through exposure to boiling water.

In an embodiment, the photoinitiator-labeled target-probe complex is contacted with a solution comprising a polymer precursor. As used herein a "polymer precursor" means a molecule or portion thereof which can be polymerized to form a polymer or copolymer. Polymer precursors include any substance that contains an unsaturated moiety or other functionality that can be used in chain polymerization, or other moiety that may be polymerized in other ways. Such precursors include monomers and oligomers. In an embodiment, the solution further comprises a solvent for the polymer precursor. In an embodiment, the solvent is aqueous.

The polymer precursor solution may also comprise other components, including molecules which serve to accelerate the polymerization reaction. In an embodiment, an amine co-initiator is present in a concentration from 22.5 mM to 2250 mM. In an embodiment, the amine co-initiator is methyl diethanol amine. In an embodiment, an accelerant is present in a concentration from greater than zero to 250 nM. In an embodiment, the accelerator is 1-vinyl-2-pyrolidinone. In an embodiment, the concentration of vinyl pyrrolidinone and MDEA are 30-40 mM and 200-250 mM, respectively. In an embodiment, the accelerator is 1-vinyl-2-pyrolidinone. In an embodiment, the initial composition of polymer precursor solution does not include photoinitiator.

In an embodiment, the concentration of the monomer components is selected to avoid excessive polymer film thickness, thereby facilitating quantitative determination of the number of molecular recognition events from the polymer film thickness. In an embodiment, the monomer solution is formulated to so that it does not unduly enhance propagation rates and or minimize termination rates, in contrast to formulations more suitable for encapsulation applications.

In an embodiment, the backbone of the monomer comprises sufficient hydrophilic monomeric units that the polymer precursor is water soluble. In an embodiment, the hydrophilic monomeric units are selected from the group consisting of ethylene glycol, acrylate, acrylate derivatives such as acrylamide and hydroxyethylacrylate, and vinyl monomers such as 1-vinyl-2-pyrolidinone. In different embodiments, the molecular weight of the polymer is between 200 and 5000 or between 300 and 1000.

In an embodiment, the polymer precursor solution comprises a difunctional polymer precursor. In one embodiment, the amount of difunctional polymer is less than 5 wt % of the total weight of the polymer precursors. In another embodiment the amount of difunctional polymer in the solution is from 5 up to 50 wt % (wt % as compared to the solution as a whole). In different embodiments, the amount of difunctional polymer precursor as compared to the total weight of polymer precursors in solution is at least 25 wt %, 50 wt %, 75 wt %, or 90% wt %. The inclusion of substantial amounts of difunctional monomer is believed to aid in the formation of greater amounts of polymer for a given polymerization time. For example, the presence of difunctional acrylate can yield pendant double bonds in propagating polymer chains that may crosslink with other propagating chains, thus suppressing chain termination rates and causing large amounts of high molecular weight polymer to be generated at the molecular recognition site.

In an embodiment, the solution comprises a difunctional polymer precursor with acrylate groups at each end. In an embodiment, the difunctional polymer precursor has a poly (ethylene glycol) (PEG) backbone and acrylate end groups. In an embodiment, the molecular weight of this difunctional PEG monomer is between 300 and 1000. In an embodiment, the weight percent of the difunctional PEG monomer in aqueous solution is from 5% to 50%.

In another embodiment, the solution comprises a mixture of a difunctional monomer with a vinyl group at each end and a monomer with a single vinyl group. In an embodiment, the polymer precursor solution comprises acrylamide and a bis-acrylamide crosslinker such as N,N-methylene-bis-acrylamide. As is known to the art, polymerization of these components forms polyacrylamide gel; the structure of the gel (average pore size) is dependent upon the total amount of acrylamide present and the relative amount of cross-linker. In an embodiment, the total amount of acrylamide and bisacrylamide is 40 wt % in aqueous solution and 5 mole % of the acrylamide is N,N-methylene-bis-acrylamide. These acrylamide solutions can be used produce thicker polymer coatings than some of the PEG solutions. This formulation is compatible with nitrocellulose-coated glass slides which are desirable for antibody array testing.

In an embodiment, the pH of the polymer precursor solution is greater than 7 and less than or equal to 9. In an embodiment, the pH of the polymer precursor solution is between 8 and 9. Since the pH of the solution can affect free radical formation, it is desirable to control the pH of the solution during the photopolymerization step.

In another embodiment, the polymer precursor is capable of forming a polymer gel. In an embodiment, the gel is covalently crosslinked and a cross-linking agent is added to the polymer precursor containing solution. In another embodiment, the gel is noncovalently crosslinked. In an embodiment, the polymer gel formed is not substantially fluorescent, magnetic, radioactive, or electrically conducting. Instead, detection can occur through absorption of a fluorescent, magnetic, radioactive, or electrically conducting solution by the gel. Detection can also occur through visual inspection of the quantity of gel formed is sufficiently large.

In an embodiment, the polymer gel is a hydrogel. The term "hydrogel" refers to a class of polymeric materials which are extensively swollen in an aqueous medium, but which do not dissolve in water. In general terms, hydrogels are prepared by polymerization of a hydrophilic monomer under conditions where the polymer becomes cross-linked in a three dimensional matrix sufficient to gel the solution. The hydrogel may be natural or synthetic. A wide variety of hydrogel-forming compositions are known to the art. In an embodiment, the monomer used to form the hydrogel is selected from the group consisting of acrylates, methacrylates, acrylamides, methacrylamides, cyclic lactams and monomers with ionic functionality. Monomers with ionic functionality include methacrylate, methacrylamide, and styrene based monomers with acidic or basic functionality. In an embodiment, the monomer used to form the hydrogel is an acrylate or methacrylate. In another embodiment, the hydrogel-forming monomer is selected from the group consisting of polysaccharides and proteins. Polysaccharides capable of forming hydrogels include alginate, chitin, chitosan, cellulose, oligopeptides, and hyalauric acids. Proteins capable of forming hydrogels include albumin and gelatin. Suitable acrylate mixtures for hydrogel formation include, but are not limited to, mixtures of hydroxyethyl acrylate (HEA) and elthylene glycol dimaethacylate (EGDMA). In an embodiment, the monomer is hydroxyl ethyl acrylate (HEA).

In different embodiments, the polymer precursor is a photopolymerizable monomer capable of forming a fluorescent polymer, a magnetic polymer, a radioactive polymer or an electrically conducting polymer. In an embodiment, the polymer precursor is water soluble. In an embodiment, the polymer precursor is a photopolymerizable fluorescent methacrylate monomer. When the polymer precursor is fluorescent, the fluorophore may absorb the light used in the photopolymerization process. To compensate, the exposure time of the polymer precursor to the light and/or the light intensity can be adjusted. In another embodiment, the polymer precursor need not be capable of forming a fluorescent, magnetic, radioactive or electrically conducting polymer if sufficient quantities of the polymer can be formed. In this embodiment, the polymer precursor can be any photopolymerizable polymer precursor or monomer. In an embodiment, the polymer precursor can be an acrylate or a mixture of acrylates. The polymer precursor can also comprise a chromophore. In an embodiment, the photoinitiator and chromophore preferentially absorb different wavelengths of light.

In another embodiment, the polymer precursor solution further comprises microparticles or nanoparticles that can be used to trigger a measurable response and these particles are incorporated into the polymer mass during polymerization. For example, the particles may be fluorescent, magnetic, radioactive, electrically conducting, or absorptive/colored. As used herein, nanoparticles have an average size greater than or equal to 1 nm and less than 1000 nm. As used herein microparticles have an average size greater than or equal to 1 micron to less than 1000 microns. In an embodiment, the particles are nanoparticles. In different embodiment, the average size of the nanoparticles is from 1 to 500 nm, from 5 to 200 nm, from 5 to 100 nm, from 10 to 50 nm, or from 20 to 40 nm.

In an embodiment, the particles are fluorescent particles. Fluorescent particles known to the art include fluorescently labeled microspheres and nanospheres. These particles include surface labeled spheres, spheres labeled throughout, and spheres possessing at least one internal fluorescent spherical zone (as described in U.S. Pat. No. 5,786,219 to Zhang et al.) Other fluorescent particles known to the art include quantum dots (QDots). These include naturally fluorescent cadmium selenium nanoparticles that have optical properties that are tunable with their size.

In an embodiment of the present invention, the fluorescent particles are microspheres or nanospheres having fluorescent dye substantially contained within the particle, rather than being present only on the surface of the particle. Such particles may also be referred to as having the dye encapsulated within the particles. Such particles are commercially available and are commonly termed microspheres (even for particle diameters less than one micrometer). Containment of the dye within the beads is believed to limit interaction of the dye with the other components of the polymer precursor solution, since physical contact of the dye with these components is limited. In an embodiment, the microspheres or nanospheres are polystyrene particles or beads. The surface of the microspheres or nanospheres may be modified in a variety of ways. Commercially available modifications include carboxylate-modified products, amine-modified products, sulfate and aldehyde-sulfate modified products. In an embodiment, nanospheres used in the present invention are carboxylate modified; the resulting microspheres has been stated to be highly charged and relatively hydrophilic (Molecular Probes Product Information, "Working with FluoSpheres® Fluorescent Microspheres, 1994).

In an embodiment, the polymerization product is a polymer gel and the particles are incorporated into the gel. In an embodiment, the network structure of the gel allows encapsulation of the particles without covalent attachment of the particles to the gel network. In another embodiment, the particles are covalently attached to the polymer formed.

Surface treatment of the particles may be used to obtain covalent attachment of the particles to the polymer formed. The appropriate form of surface treatment may vary with the type of particle and the type of polymer, but may include attachment of functional groups, monomers or polymers to the surface. In an embodiment, pendant acrylic monomers may be coupled to the surface of the particles. Acrylic monomers may be coupled to the particle surface by reaction of commercially available particles with acrylate molecules. Polymers may also be attached to the surface through polymerization from the surface.

In an embodiment, the dye contained within particles is selected for compatibility with the photopolymerization process. The absorption spectrum of the dye may overlap that of the initiator, so long as polymerization is not reduced to unacceptable levels. If the absorption spectra overlap, the intensity and/or exposure of the light may be adjusted accordingly to compensate.

In another embodiment, the dye contained within the particles is selected for compatibility with a particular detection device. For example, the dye may be selected so that it has an emission maximum suitable for a particular filter set.

In an embodiment, fluorescent particles suitable for use with fluorescein or fluorescein-derivative initiators can encapsulate dyes having excitation and emission maxima which fall within a relatively broad range of values. In an embodiment, the fluorescent particles can have an absorption/ excitation maximum which falls in the range from approximately 500 to approximately 670 nm and an emission maximum which falls in the range from approximately 510 to approximately 690 nm. Suitable fluorescent particles include, but are not limited to, Crimson (excitation/emission maxima of 625/645 nm), Nile Red (broad excitation/emission bandwidths of 535/575 nm), Yellow-Green (excitation/emission maxima 505/515 nm), and Dark Red (excitation/emission maxima of 660/680) FluoSpheres®, all available from Invitrogen.

In an embodiment, the amount of oxygen dissolved in the polymer precursor solution is minimized to minimize oxygen inhibition of the polymerization process. In an embodiment, the oxygen content of the solution is less than about $1 \times 10^{-5}$ moles/liter. The amount of oxygen dissolved in the solution may be minimized by control of the atmosphere under which polymerization takes place, reducing the oxygen content of the polymer precursor solution by flowing a gas through it and/or the addition of oxygen inhibition agents. The "purge" gas used to reduce the oxygen content of the polymer precursor solution may be flowed through the polymer precursor solution prior to contact of the precursor solution with the target probe complex, during contact of the precursor solution with the target probe complex, and/or during polymerization. In an embodiment, oxygen inhibition agents such as multifunctional thiol reagents are not used. In an embodiment, the oxygen content of the polymer precursor solution during polymerization can be minimized by performing the polymerization in an enclosure and introducing a gas which does not have a substantial oxygen content into the enclosure. In different embodiment, the oxygen content of the gas is less than about 10%, less than about 5% and less than about 1%. Suitable gases include, but are not limited to, commercial purity argon and nitrogen. The atmosphere in the enclosure may be obtained by simply filling the enclosure with the desired gas, or by flowing gas through the enclosure. The enclosure can also be evacuated and backfilled with gas. The oxygen content of the polymer precursor solution can also be reduced prior to polymerization by bubbling a suitable gas through the solution, or by any other method known in the art. Suitable gases include those which do not have a substantial oxygen content, such as argon and nitrogen. Oxygen and air are not suitable purge gases.

The solution may further comprise oxygen inhibition agents and/or cross-linking agents. In an embodiment, the oxygen inhibition agent is a multithiol (Bhanu, V. A. & Kishore, K. (1991) Role of Oxygen in Polymerization Reactions, *Chemical Reviews* 91: 99-117). The amount of oxygen inhibition agent should not be so much that polymerization occurs in the bulk of the solution rather than from the surface. However, oxygen inhibition agents which can act as chain transfer agents are not recommended for use with radical polymerization processes when it is desired to form sufficient quantities of the polymer for visual detection. A crosslinking agent can stabilize the polymer that is formed and improve the amplification factor (Hacioglu B., Berchtold K. A., Lovell L. G., Nie J., & Bowman C. N. (2002) Polymerization Kinetics of HEMA/DEGDMA: using Changes in initiation and Chain Transfer Rates to Explore the Effects of Chain-Length-Dependent Termination. *Biomaterials* 23:4057-4064). Finally, a small amount of inhibitor can be added to the formulation to limit background polymerization caused by impurities and trace radicals formed by absorption by molecules other than the initiator.

The photoinitiator-labeled target-probe complex and polymer precursor are exposed to light, thereby forming a polymer. Photopolymerization occurs when polymer precursor solutions are exposed to light of sufficient power and of a wavelength capable of initiating polymerization. The wavelengths and power of light useful to initiate polymerization depends on the initiator used. Light used in the invention includes any wavelength and power capable of initiating polymerization. Preferred wavelengths of light include ultraviolet or visible. In different embodiments, the light source primarily provides light having a wavelength between 200 and 400 nm, between 200 nm and 380 nm, or from 200 nm. In an embodiment, the light source primarily provides light having a wavelength between 400 and 700 nm. Any suitable source may be used, including laser sources. The source may be broadband or narrowband, or a combination. The light source may provide continuous or pulsed light during the process. Both the length of time the system is exposed to UV light and the intensity of the UV light can be varied to determine the ideal reaction conditions. For fluorescence detection, the exposure time and light intensity can be varied to obtain maximal fluorescence signal from spots on a microarray and minimal fluorescence signal from the background. In an embodiment, the intensity of UV radiation is selected so that an appropriate dose of UV radiation can be delivered in less than about one-half hour.

In an embodiment, after polymerization, unpolymerized polymer precursor is removed. The unpolymerized polymer precursor can be removed by rinsing, for example by rinsing with water or an aqueous solution. The unpolymerized polymer precursor need not be removed if formation of the polymer is to be detected by its refractive index or by other means that would not be interfered with by the presence of the unpolymerized polymer precursors.

If the hydrogel polymer is not substantially fluorescent, magnetic, radioactive, or electrically conducting, the hydrogel can be contacted with a detectable solution which is fluorescent, magnetic, radioactive, or electrically conducting so that the hydrogel absorbs a sufficient quantity of the detectable solution. After the detectable solution is absorbed into the hydrogel, the excess solution is removed before detection.

In an embodiment, the polymer formed is detected by fluorescence, magnetic, radioactive or electrical detection methods as are known to the art. If the probes are part of a DNA microarray, a commercially available microarray scanner and/or imager can be used to detect polymer formation. DNA microarray scanners and/or imagers are commercially available that can detect fluorescent or radioisotopic labels.

In another embodiment, sufficient quantities of the polymer are formed that polymerization can be detected by visual inspection. Polymerization which is detectable by visual inspection may also be detectable via image analysis of photographs or digital images of part or all of the array or substrate. Polymerization can be detected by visual inspection when there is sufficient contrast between the areas where polymer has formed and the unpolymerized monomer, the other areas of the array or the array substrate. In an embodiment, the areas where the polymer has formed appear to be a different color (or shade of gray) than the unpolymerized monomer, the other areas of the array or the array substrate. For example, after unpolymerized monomer is removed, the areas where polymer has formed may appear darker than the array substrate. In another embodiment, the areas where the polymer has formed can have a different transparency than the unpolymerized polymer precursor. For example, the unpolymerized polymer precursor may be clear and the polymer more opaque and whitish in color. The amount of polymer required for visual detection of polymer formation may depend upon the polymer. For acrylate mixtures such as mixtures of Hydroxyethyl Acrylate (HEA) and Ethylene Glycol Dimethacrylate (EGDMA), the thickness of the polymer formed can be greater than about 1 micron, or greater than about 5 microns. Determination of polymer formation may be made with either swollen or dried gels. For accurate polymer film thickness measurements, the gels are typically dried.

Analysis of polymer formation can allow identification of the target. Methods of design and analysis of DNA microarrays for identification of target molecules are known to the art (Vernet, G. (2002) "DNA-Chip Technology and Infectious Diseases" Virus Research 82:65-71). Similar methods, appropriately modified, can be applied to other types of microarrays and molecular recognition events.

The sensitivity of the detection methods of the invention can be measured in several ways. In an embodiment, a microarray dilution chip may be prepared having spots with differing amounts of a target or test species or molecule which is capable of binding with the photoinitiator label. In an embodiment, a test species is chosen which is expected to have similar binding/capture properties for the photoinitiator label. In different embodiments, the test species may be a biotinylated oligonucletide or double stranded DNA hybrid. The photoinitiator label is then attached to the target or test species. After photopolymerization, it may be observed which spots on the chip result in a detectable amount of polymer formation. When the surface concentration of the target or test species of a given spot is known, polymer formation at the spot indicates detection of at least that concentration level of the target or test species. When the size of the spot is known, the sensitivity can be determined in terms of the number of molecules required for detection. The sensitivity of the method determined by detection of a test species is expected to be related to the actual sensitivity of the method for detection of a target species, but may also be affected by factors such as labeling efficiency and hybridization efficiency. The assessed sensitivity of the method may depend on the sensitivity of method used to assess whether polymerization has occurred, with more sensitive polymerization assessment methods demonstrating greater sensitivity of the detection method. For example, when polymerization is assessed via optical observation the observed sensitivity may be lower then when polymerization is assessed via profilometry measurements. In an embodiment, the methods of the invention are capable of detecting a concentration of 0.4 attomoles ($4 \times 10^{-19}$ moles) when detection is assessed optically (by eye or with an optical microscope) and 0.1 attomoles when detection is assessed through profilometer measurements.

An amplification factor, which can be defined as the number of propagation reactions occurring per molecular recognition event, can be calculated from analysis of the thickness of the polymer films. The volume of the film may be divided by the density of the polymer to obtain the mass of polymer formed. Division by the molecular weight of the monomer/polymer precursor/repeat unit gives the number of monomers reacted into the polymer matrix. Dividing the number of monomers per micron squared by the number of molecular recognition events per micron squared gives the amplification factor. In an embodiment, the amplification factor of at least $10^6$ or $10^7$ is obtained for each molecular recognition event. If the amplification factor is determined across a given concentration range, the thickness of the film can be used as a measure of the number of molecular recognition events (in that concentration range).

In an embodiment, the number of molecular recognition events can be quantitatively determined by comparison of the observed film thickness (or other detectable characteristic) to a reference calibration curve of film thickness (or other detectable characteristic) versus target or test species concentration on a solid surface. The reference calibration curve or correlation is obtained for similar photopolymerization conditions (photoinitiator label, polymer precursor solution, light source, light intensity, and light exposure time). This calibration curve may be obtained by preparation of a dilution chip fabricated by spotting decreasing concentrations of the target or test molecules onto a substrate, then attaching photoinitiator labels to the target or test molecules and photopolymerizing a monomer solution from the surface bound initiators according to the detection methods of the invention. The concentrations of the target or test molecules can be determined for a similar dilution chip by attaching a fluorescent label to the molecules and then characterizing the surface with fluorescent detection methods.

The relationship between the detectable characteristic and the surface concentration may be useful over a limited range of target or test species surface concentrations. This useful range may also be referred to as the dynamic range. The lower end of the range may be limited by the detection level of the detectable characteristic. The upper end of the range may be limited by a "saturation" effect. For example, in some cases the thickness of the polymer film appears to increase much more slowly at higher surface concentrations. Measurements in the useful range may be obtained by repetition of the experiment with different experimental conditions. In another embodiment, the probe array may be provided with spots having different concentrations of the same probe molecule to increase the likelihood that at least one spot will have a surface concentration in the useful range.

In another embodiment, quantitative analysis of the target molecule concentration can be performed by changing the exposure time systematically across an array of sample spots. Comparison of the dose at which polymerization is observed with a calibration curve of dose versus concentration allows quantitative determination of the concentration. In another embodiment, the probe array may be provided with different concentrations of the same probe molecule and a single exposure time used for the array.

In different embodiments, the methods of the invention are capable of detecting as few as $10^3$ or $\sim 10^4$ labeled oligonucleotides using minimal instrumentation, such as an optical microscope or CCD camera. In other embodiments, the methods of the invention are capable of visual detection of concentrations as few as 100, 50, 25, 10, 5, 1, 0.5, 0.1 or 0.005 biomolecules/$\mu m^2$.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

All patents and publications mentioned in the specification are indicative of the levels of skill of those skilled in the art to which the invention pertains.

All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

Example 1

Synthesis of a Water Soluble Initiator

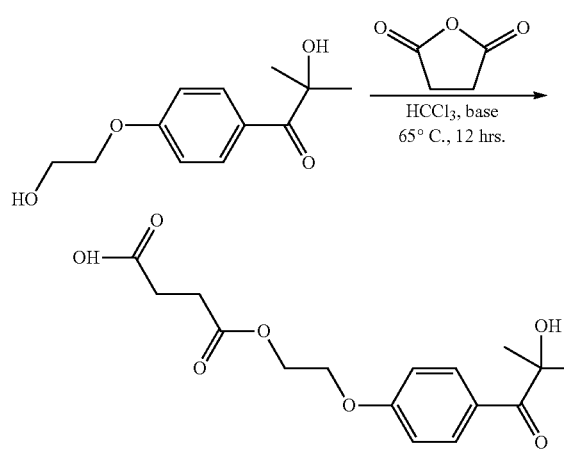

Scheme 1.

As shown in Scheme 1, synthesis of a water soluble photoinitiator (preferred for compatibility with a BioChip) was achieved by starting with commercially available Irgacure 2959 (left most structure, Ciba Specialty Chemicals) Irgacure 2959 was dissolved/suspended in chloroform along with succinic anhydride and a catalytic amount of 4-dimethylaminopyridine. The solution was refluxed, with stirring, for 12 hours at 65° C. In both chloroform and water, the product was soluble while the starting materials were sparingly soluble. The product structure was verified by NMR and shown to function as a photoinitiator by monitoring the double bond conversion of an acrylate monomer using time-resolved FTIR.

Example 2

Functionalization of Avidin with Photoinitiator

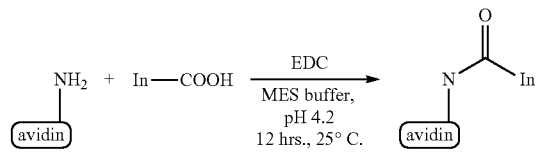

Scheme 2.

Avidin is often labeled with dye molecules by modification of its many lysine residues (for example, Pierce Biotechnology sells a kit for this purpose). These types of modifications do not disrupt avidin's ability to bind to biotin (Wilbur, D. S.; Hamlin, D. K.; Buhler, K. R.; Pathare, P. M.; Vessella, R. L.; Stayton, P. S.; To, R. (1998) "Streptavidin in antibody pretargeting. 2. Evaluation of methods for decreasing localization of streptavidin to kidney while retaining its tumor binding capacity" *Bioconjugate Chemistry* 9: 322-330). Here, as shown in Scheme 2, the lysine residues have been modified with a photoinitiator (rather than a dye) by coupling the carboxylic acid functional group of the photoinitiator to the amine of the lysine residue. The result is formation of a peptide bond between the initiator and the protein. Avidin and an excess of the initiator (the product in Scheme 1, represented by In in Scheme 2) were dissolved in an acid aqueous buffered solution in the presence of the water-soluble coupling agent 1-ethyl-3-(3-dimethylaminopropyl) carbodiimide (EDC) (Hermanson, G. T. (1996) *Bioconjugate Techniques* San Diego, Calif.: Academic Press. p. 435). The reaction proceeded at room temperature for 12 hours, and the product was collected by ultracentrifugation through a 3,000 MW cutoff filter. Biotin binding capabilities were verified using the HABA assay (Wilcheck, M., (b) Bayer, E. A. Eds. (1990) "Protein biotinylation" *Methods in Enzymology* 184: 138-160).

Example 3

Synthesis of a Polymer Labeled with Photoinitiator and Streptavidin

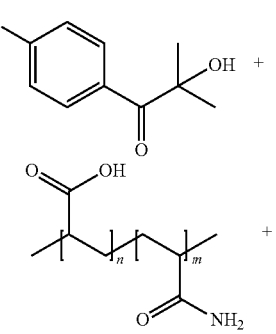

Scheme 3.

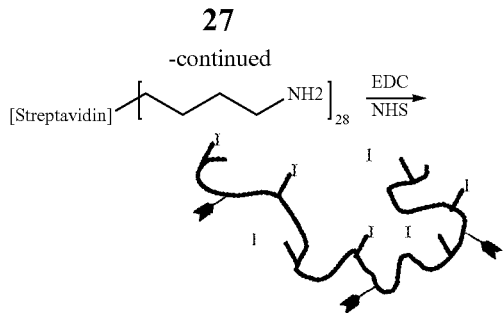

Scheme 3 illustrates the formation of a polymer labeled with Irgacure 2959 photoinitiator (denoted by I) and streptavidin (denoted by ⌇).

Macroinitiators were synthesized using poly(acrylic acid-co-acrylamide) (MW=200,000 g/mol), Irgacure 2959, and streptavidin as starting materials. The water-soluble coupling agent 1-ethyl-3-[3-dimethylaminopropyl]carbodiimide (EDC) and the intermediate-stabilizing molecule N-hydroxysuccinimide (NHS) were used to create amide linkages between some of the acrylic acid subunits and streptavidin and to create ester linkages between other acrylic acid subunits and the initiator Irgacure 2959 (I2959). Still other acrylic acid subunits were left unmodified to assure the water solubility of the resulting macroinitiator. Two types of reaction conditions were varied in order to change the number of initiators that coupled per chain. First, the stoichiometry of reactants was varied up to the limit of solubility of the initiator in the aqueous conjugation buffer. Second, the length of time allowed for the activation step (in which EDC and NHS react with the carboxylic acid subunits of poly(acrylic acid-co-acrylamide)) was varied. Table 1 summarizes results from three sets of reaction conditions.

TABLE 1

| | Stoichiometry | Activation time | Absorbance at 300 | Initiators per chain* |
|---|---|---|---|---|
| 1 | 685 μL of 1 mg/ml I2959<br>440 μL of 1 mg/ml EDC | 10 minutes | 0.8 | 140 |
| 2 | 260 μL of 1 mg/ml NHS<br>685 μL of 1 mg/ml I2959<br>440 μL of 1 mg/ml EDC | 15 minutes | 1.3 | 40 |
| 3** | 260 μL of 1 mg/ml NHS<br>68.5 μL of 1 mg/ml I2959<br>44 μL of 1 mg/ml EDC<br>26 μL of 1 mg/ml NHS | 15 minutes | 0.5 | 88 |

*Calculated using a standard curve of absorbance at 300 of the initiator as a function of initiator concentration.
**Reaction 3 was brought up to equal volume with Reactions 1 and 2 using the conjugation buffer.

After activation, the initiator and protein are added and the reaction takes place in the presence of EDC and N-hydroxysuccinimide (NHS) at room temperature for about two hours.

Example 4

Macroinitiator Synthesis

In the event that a label sequence containing a single initiator does not provide a high enough level of amplification with the short irradiation times necessary to minimize background fluorescence, macroinitiators, in which many initiators are present on a single molecule, can be used. Synthesis of a macroinitiator can be achieved through a living (or controlled) radical polymerization method prior to utilization on the microarrays (Kamigaito M., Ando T., & Sawamoto M. (2001) "Metal-Catalyzed Living Radical polymerization. *Chemical Reviews* 101: 3689-3746). Atom transfer radical polymerization (ATRP) schemes can be used to control the macroinitiator molecular weight, composition and architecture (block copolymers, branching, etc.) (Matyjaszewski, K. & Jianhui Xia, J. (2001) Atom Transfer Radical Polymerization *Chemical Reviews* 101: 2921-2990).

Scheme 4. Reaction for generation of macroinitiator.

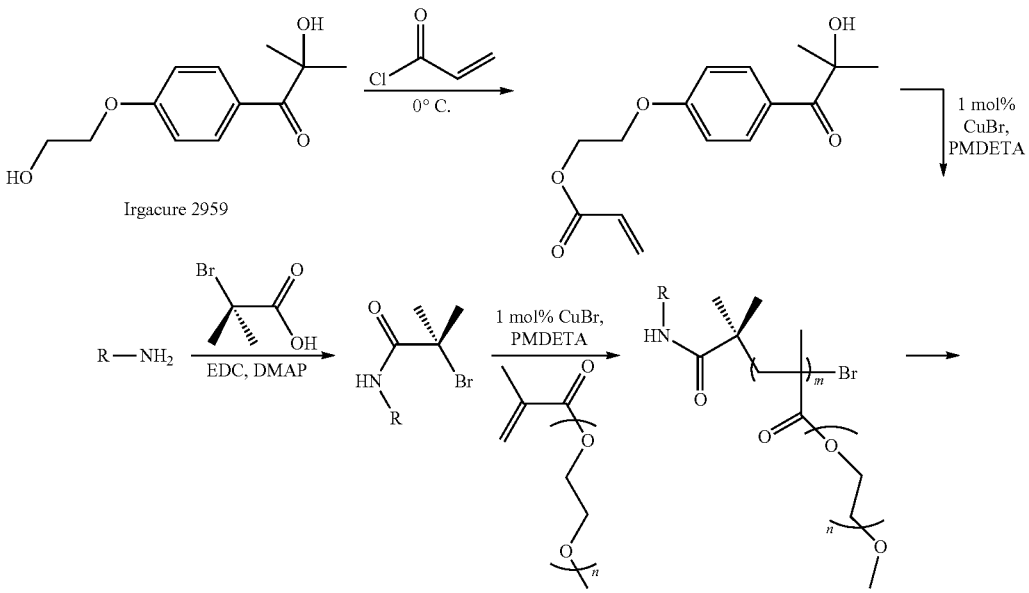

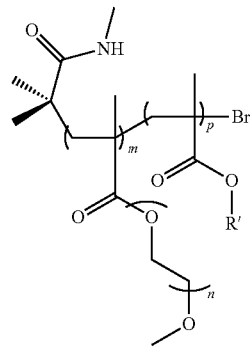

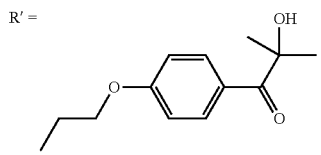

Macroinitiator synthesis can be performed, as presented in Scheme 4, by starting with an oligonucleotide terminated in an amine group. The amine terminus is functionalized with an ATRP initiator, which initiates polymerization of the desired compounds. As many as three different monomers (an initiator, a spacer, and a photosensitizer) may need to be copolymerized. If necessary to improve hybridization to the probe oligonucleotide, a spacer molecule (for example (poly ethylene glycol methacrylate)) is used between the initiating block of the macroinitiator and the oligonucleotide part of the label sequence. The spacer may also be used for controlling solubility of the macroinitiator (by changing the hydrophobicity/hydrophilicity) and the macroinitiator molecular weight. Photosensitizing components are incorporated into the macroinitiator in systems where minimization of the background polymerization is necessary.

Example 5
Synthesis and Photopolymerization of a Fluorescent Monomer

Scheme 5.

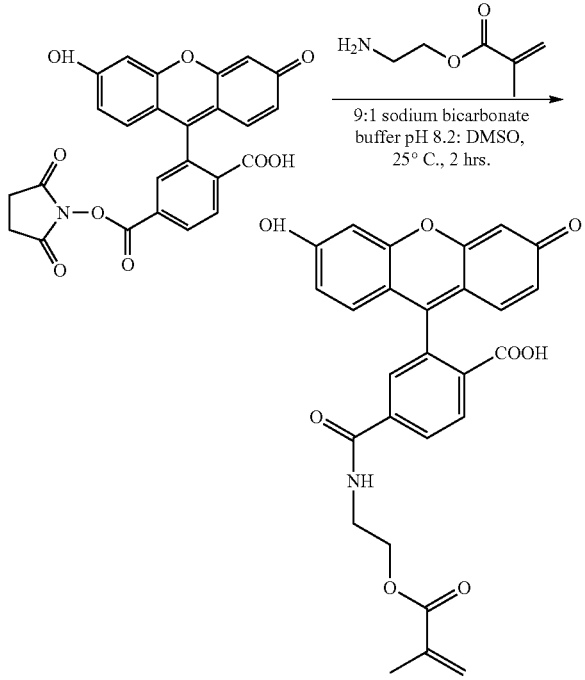

The N-hydroxy succinimide ester of fluorescein was purchased from Pierce Biotechnology (Rockford, Ill.) and 2 mg were dissolved in 100 µL of DMSO while 0.5 mg of 2-aminoethyl methacrylate was dissolved in 900 µL of sodium bicarbonate buffer, pH 8.2. The two solutions were combined and placed on a shaker for two hours. The solvent was lyophilized off. The structures of the fluorescent monomer and the polymer that results from irradiating the monomer with UV light were verified by NMR.

The monomer can be polymerized by irradiating with 365 nm ultraviolet light for one minute.

Example 6

Formation of a Hydrogel from a Polymer Labeled with Photoinitiator and Streptavidin and Detection of the Hydrogel Formed The polymer of Example 3 was reacted with a microarray having biotin covalently bound to the microarray substrate. A hydroxyl ethyl acrylate monomer solution was placed in contact with the array by pipetting the solution into a HybriWell (Grace Biolabs) which covers the array. Sixty µl of an aqueous solution was used which contained hydroxyl ethyl acrylate, initiator (product of Scheme 1 and Scheme 3), cross-linking agent (ethylene glycol dimethacrylate, 3% by volume), and oxygen inhibition agent (mercaptoethanol, $5 \times 10^{-4}$% by volume).

The monomer was then photopolymerized to form a hydrogel by irradiating the array with 365 nm light for about 1 minute.

After polymerization, the microarray was rinsed with water and then a solution containing Rhodamine B, concentration 100 nM, was pipetted between a glass coverslip and the microarray. The microarray was exposed to the fluorophore containing solution for about 30 minutes. The microarray was then rinsed with water to remove excess fluorophore.

Figure 3A:
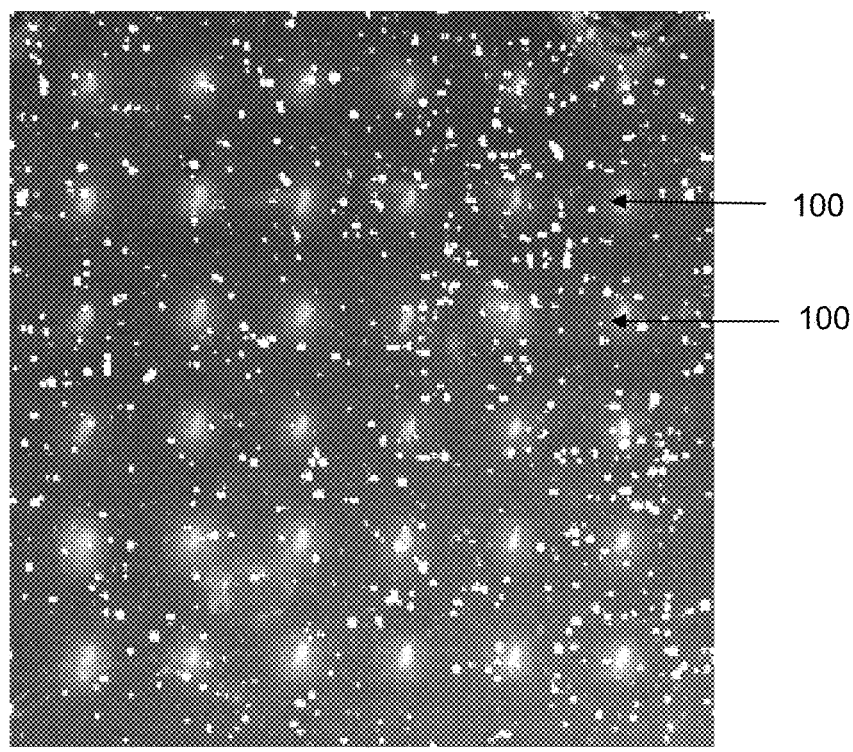
FIGS. 3A and 3B illustrate fluorescence detection of macroinitiators on a biotin array.
Figure 3B:
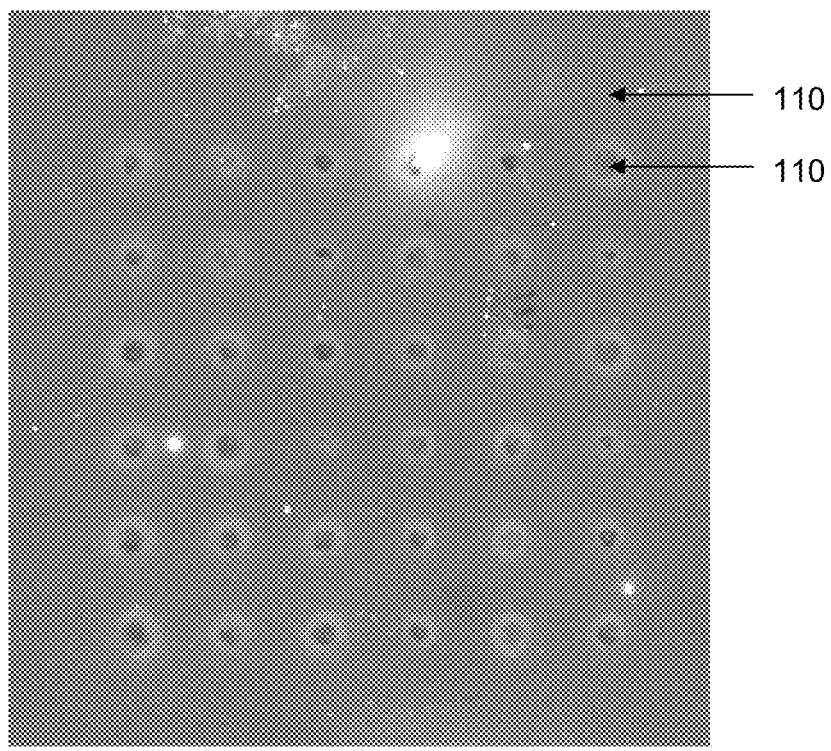

FIG. 3A is an image of the array after polymerization. The grid of reacted biotin spots (100) are bright and indicate areas of formation of hydrogel swollen with the fluorescent solution. The detector used was an Agilent Microarray Scanner (Fluorescence Ave: 2600, Std: 1200 Background: 1200Signal to Noise: 2.2). FIG. 3B shows negative controls spots (110) on the same array (Fluorescence Ave: 900, Std: 30, Background: 800, Signal to Noise: 1.1)

Example 7

On-Chip Hybridization, Amplification, and Detection on a Flu Chip

Figure 4:
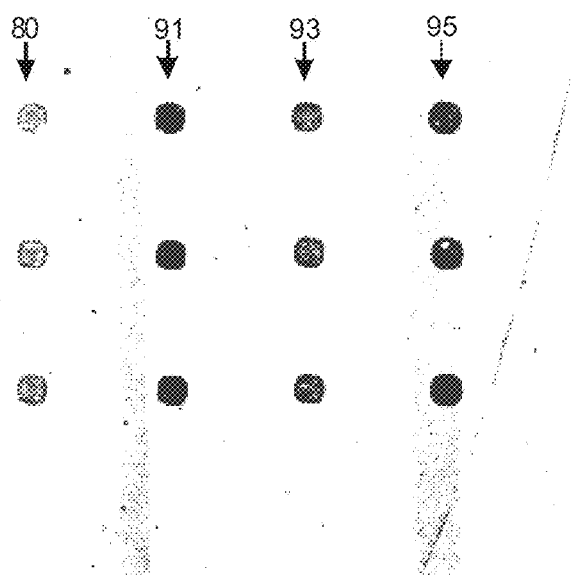
FIG. 4 illustrates an image of a FluChip developed using photopolymerization for signal enhancement.

On-chip signal amplification by photopolymerization was tested on a custom microarray designed to detect and subtype the influenza virus. As shown in FIG. 4, the chip had a column of positive control spots (80), spots to capture RNA of influenza C (91), spots to capture RNA of influenza B (93), and spots to capture RNA of influenza A (95). There were three spots in each column. The sequence that is complementary to the positive control spots (but not to the other nine spots on the array) was purchased from Qiagen (Valencia, Calif.) with a 5' biotin modification. Published protocols were used to hybridize a 1 µM solution of this oligonucleotide to the microarray. The hybridization procedure was as follows:

Pre-hybridization.
1. Boil $dH_2O$.
2. While $dH_2O$ is boiling, wash microarray in 0.1% sodium dodecyl sulfate (SDS) for 2-10 min on rocker. (0.5 ml 10% SDS in 50 ml total volume).
3. Transfer to 2× standard saline citrate (SSC) for 2 min. (5 ml 20× in 50 ml total volume).
4. Immerse slide in boiling/hot (>95° C.) water for 2-3 min.
5. Remove slide, blot on kimwipe.
6. Immerse slide in ice-cold ethanol bath for 2-5 min. Store EtOH at −20° C.
7. Remove slide, blot on kimwipe.
8. Centrifuge ethanol off of slide. (50 ml conical tube, 1000 rpm, 3 min).

Hybridization.
1. Pipette 10 µL of water or buffer into the humidification slots, place microarray in hybridization cassette.
2. Hybridization solution:
    10 µL 50 micromolar oligo soln (phosphate-buffered saline (PBS) or tris(hydroxymethyl) aminomethane (Tris))
    10 µL 10×SSC
    5 µL 1% Tween 20 (polyoxyethylene-20-sorbitan monolaurate, ICI) 5 µL 10
    mM $MgCl_2$
    20 µL $H_2O$
3. Pipette 7 µL of this solution between a coverslip covering the microarray and the slide.
4. Seal cassette, submerge in water bath (40-45° C.) for at least 1.5-2 hrs.

Washing.
1. Transfer microarray immediately into 1×SSC (2.5 ml 20× in 50 ml total)/0.1% SDS (0.5 ml 10% SDS in 50 ml total). 5 min.
2. Transfer microarray into 0.1×SSC (0.25 ml 20× in 50 ml)/0.1% SDS. 5 min.
3. Immerse briefly in 0.1×SSC to remove SDS.

Rinse with water, dry with $N_2$.

Following hybridization, 7 µL of a 1 mg/ml solution of BSA was pipetted between a glass coverslip and the microarray to block nonspecific binding. Following twenty minutes of incubation in a humid hybridization chamber, the array was rinsed with water. Subsequently, 7 µL of a 1 mg/ml initiator-functionalized avidin solution was pipetted between a glass coverslip and the microarray. After twenty minutes of incubation and brief rinsing with water, 7 µL of a saturated solution of the fluorescent monomer in water was pipetted between the glass coverslip and the microarray. The array was irradiated with 365 nm UV light for one minute, rinsed with water, and imaged using an Agilent (Wilmington, Del.) microarray scanner. The excitation wavelength ($\lambda_{ex}$=532 nm) and collection wavelength (centered at 575 nm) were not optimal for the fluorescein derivative (product in Scheme 3). FIG. 4 is the resulting image In FIG. 4, the lighter spots represent detected fluorescence. Though the background fluorescence remains relatively high despite the BSA treatment, the positive control spots (80) are definitely more fluorescent than the spots designed to capture the genetic material of influenza A, B and C (these spots effectively served as three different negative controls in this experiment). The faint gray vertical lines in FIG. 4 are a well understood artifact. Glass slides were placed between the microarray and the UV light source to block high frequency UV light that is harmful to the fluorophore. The vertical lines arise from the seam between two glass slides that were used as a filter in this manner.

Two other control experiments were performed. Without the BSA nonspecific binding blocking step, and all other steps held constant, the entire image yielded significant fluorescence, indicating nonspecific binding of the initiator. In addition, without the addition of avidin-functionalized initiator, when all other steps remained identical, none of the spots exhibited fluorescence yet the background was still high. These results suggest that the fluorescent spots in FIG. 4 do indeed result from an interaction between the monomer and the selectively bound initiator. These tests, taken together, indicate that photopolymerization is clearly a viable means to obtain selective signal amplification directly on a DNA microarray.

Without wishing to be bound by any specific theory, one possible cause of nonspecific binding is reaction of the fluorescent monomer with the aldehyde coating on the glass. To eliminate this source of nonspecific binding, alternative attachment chemistries are available, or the unreacted aldehydes outside of the oligonucleotide spots can be passivated or reduced. If macroinitiators containing larger numbers of initiators are used, the irradiation time can be reduced. To further reduce nonspecific binding, an inhibitor can be included. This technique will be effective if the number of initiation sites inside the hybridized spots (specific, due to the presence of many initiators) is much greater than the number of possible sites outside the spots (nonspecific, absorption and initiation occurring without initiator, and non-specific binding). False positives can be minimized by the use of macroinitiators, photosensitizers/inhibitors and optimal initiation time and light intensity, combined with judicious choice of probe and label sequence and steps to prevent nonspecific binding of the initiator to the array

Example 8

Quantification of Number of Fluors

The number of fluorescent molecules incorporated into the polymer and therefore bound to the microarray surface can be quantified. One test is to measure the shape and size of the resulting spot after polymerization is complete using either atomic force microscopy or profilometry. With this information and knowledge of the mass fraction of fluor within the mixture and the polymer density, it is possible to calculate relatively accurately the number of fluors within the polymer.

This approach minimizes error due to any fluorescence quenching within the polymer. Quenching is quantified and minimized by conducting a study of fluorescence intensity as a function of mass percent fluor in the polymer. Due to the amorphous nature of the polymer, quenching is not expected to be significant.

Example 9

Recognition Between Biotin Arrays and Polymers Functionalized with Streptavidin and Photoinitiator A biotin array was contacted with a macroinitiator solution comprising a poly (acrylic acid-co-acrylamide) polymer backbone (MW=200,000) functionalized with streptavidin and Irgacure 2959. The reaction conditions for forming the macroinitiator were as given in Table 1. The array was then washed to remove macroinitiator not attached to the biotin array. The photoinitiator-labeled array was then contacted with a monomer solution comprising Hydroxyethyl Acrylate (HEA) and Ethylene Glycol Dimethacrylate (EGDMA). The monomer solution had been previously purged with argon to reduce its oxygen content. The photoinitiator labeled array and monomer solution were then exposed to 5 mW/cm$^2$, 365 nm UV light for 20 minutes in an argon atmosphere. Unpolymerized monomer solution was then removed by washing. Details of biotin array preparation, monomer preparation, recognition and amplification procedures are given below.

Figure 5:
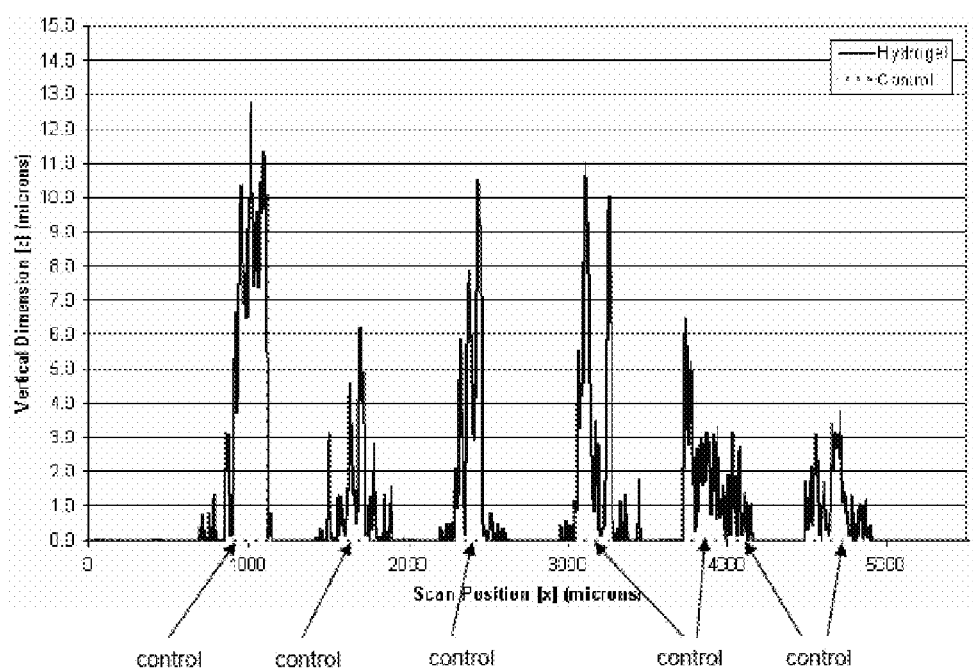
FIG. 5 shows a profilometry scan across a row of polymer spots that were grown from an array following recognition of biotin by a streptavidin macrophotoinitiator.

The product of reaction 1 (see Table 1) led to the formation of polymer spots that were up to 10 microns thick, as measured with a profilometer. FIG. 5 compares a profilometer trace across the hydrogel spots with a control profilometer trace. A digital image of the polymer spots shows that they are darker than the surrounding substrate. The product of reaction 2 led to polymerization everywhere (not just within the spots). The product of reaction 3 led to the formation of polymer spots that were up to 0.1 micron thick, as measured using a profilometer.

Biotin Array Preparation:
1. Vapor-deposit aminopropyltriethoxysilane onto a piranha cleaned silicon (or glass) substrate. Piranha cleaning involves placing substrates in 70% v/v sulfuric acid, 30% v/v 30% hydrogen peroxide at 90° C. for 1 hour. Vapor deposition includes placing substrates into a purged Teflon container along with an open vial containing the silane for two hours at 90° C.
2. Spot 1 mg/mL biotin-polyethylene glycol (PEG)-benzophenone in 1× PBS on an amine substrate. Set relative humidity in spotter to 75%. Allow substrates to dry in spotter for half hour after spotting is complete and then move to ambient conditions to dry for at least 2 hrs.
3. Covalent attachment of biotin to the surface: irradiate the substrate with UV light at 5 mW/cm2 using Black Ray lamp at 365 nm for 10 minutes.
4. Blocking of nonspecific binding: soak arrays in 1 mg/mL dry milk in water solution for two hours while slowly agitating with shaker.
5. Wash arrays ×3 in water for 5 minutes, then dry the slides using a stream of nitrogen.

Monomer Preparation:
1. Hydroxyethyl Acrylate (HEA) and Ethylene Glycol Dimethacrylate. (EGDMA) are deinhibited from MEHQ by three consecutive distillations.
2. Make 300 µL of 97 vol % HEA and 3 vol % EGDMA.
3. Purge monomer of dissolved oxygen by bubbling argon through the monomer for 10 minutes and then seal the container with Parafilm® when done.

Recognition:
1. Pipette a 20 µL of macrophotoinitiator solution (1.4 mg poly (acrylic acid-co-acrylamide backbone per ml in 0.1M 2-(N-morpholino) ethane sulfonic acid (MES) buffer, 0.5 M NaCl, pH 5) directly onto array and then drop a plastic coverslip onto drop, making sure drop spreads uniformly over coverslip area. Place slide in humid chamber for 20 minutes.
2. Wash slide ×3 in water for 5 minutes, do not dry slide with nitrogen.

Amplification:
1. Place silicone isolator around spots, making sure it adheres to the plate well. This will keep the monomer from spreading everywhere on the substrate.
2. Place plate in argon chamber and then pipette 300 µL of monomer inside the well formed by the isolator and the substrate.
3. Put glass top on chamber, turn argon on, let it purge for 5 minutes. After 5 minutes, tighten down the top on the chamber.
4. Irradiate the plate in the chamber for 20 minutes under 5 mW/cm$^2$, 365 nm UV light.
5. Remove plate from purge chamber and wash ×3 in water, dry with nitrogen. Look for polymer spots that have grown from the array.

Example 10

Polymerization of a Chromophore-Containing Monomer Using a Macroinitiator Incorporating Tertiary Amines A chromophore-containing monomer is polymerized using a photoinitiator which preferentially absorbs light at a different wavelength than the chromophore. A chromophore which preferentially absorbs UV light can be paired with a photoinitiator which preferentially absorbs visible light. Scheme 6 illustrates formation of an acrylate monomer incorporating the chromophore Cascade Blue Ethylene Diamine, which preferentially absorbs light at approximately 400 nm. Scheme 7 illustrates formation of a macroinitiator comprising a polymer incorporating multiple tertiary amines. The photoinitiator for the polymerization of the monomer comprising the tertiary amine and the acrylate group with acrylic acid is (for water solubility and to provide a functional group that streptavidin can be coupled to) Irgacure 184. 1-hydroxycyclohexyl phenyl ketone (Ciba-Geigy). The polymer chain is coupled to at least one molecular recognition group, shown as streptavidin in Scheme 7. As shown in Scheme 8, the tertiary amines of the macroinitiator and CQ form a two-part initiator system which most strongly absorbs light at 469 nm. The radical species shown in Scheme 8 propagates through the carbon-carbon double bonds of the chromogenic monomer that is the product of Scheme 6 to form a chromogenic monomer.

Scheme 6:
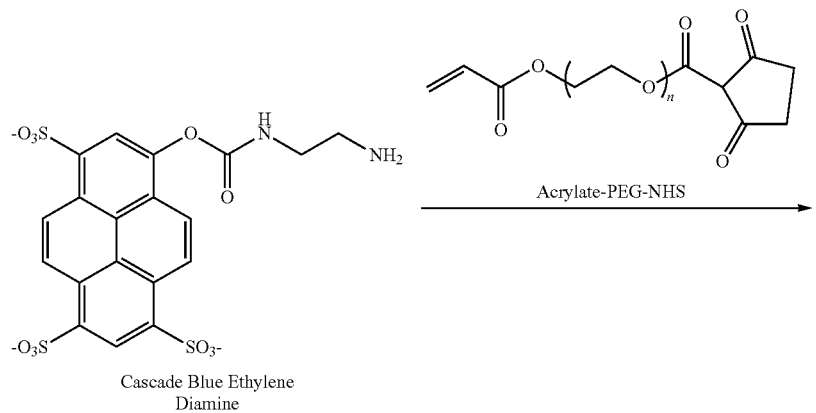
Cascade Blue Ethylene Diamine
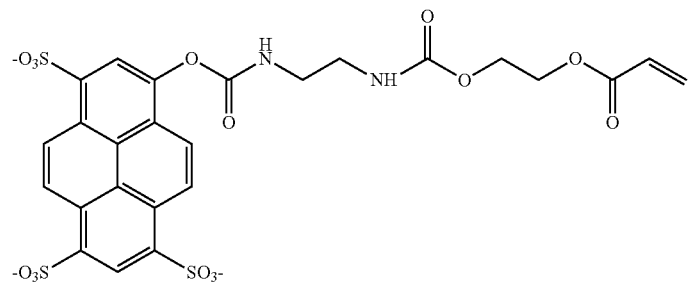
Scheme 7:
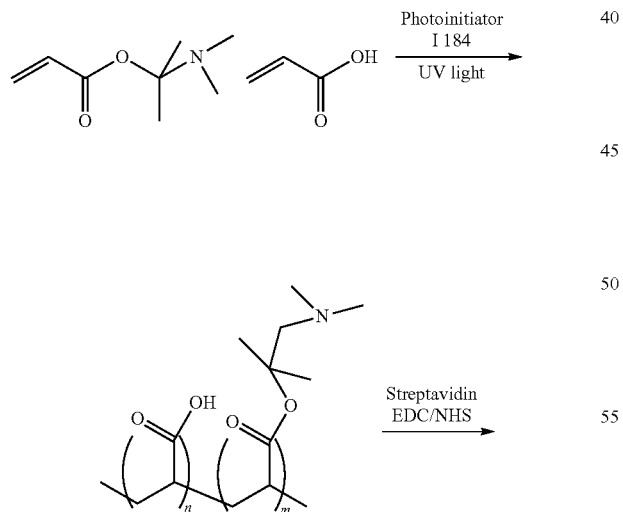
Scheme 8.
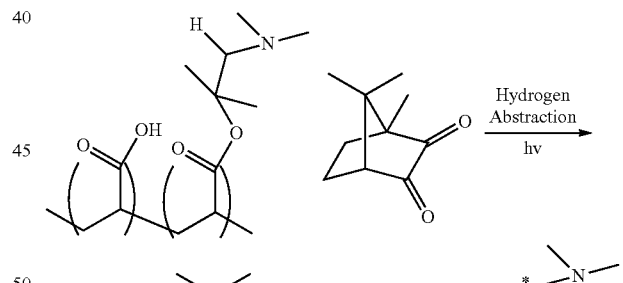
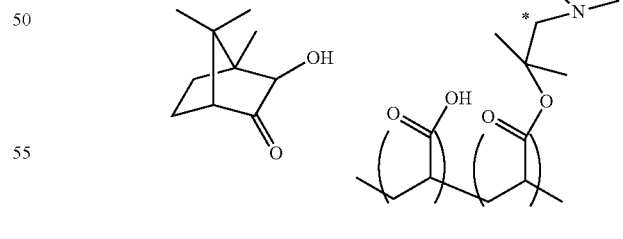
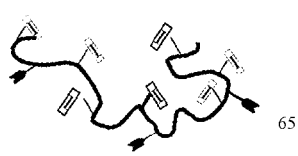
Example 11
Recognition Between Biotinylated Oligonucleotide Arrays and Polymers Functionalized with Neutravidin and Photoinitiator
Dual-functional macrophotoinitiators were synthesized by coupling water-soluble photoinitiators and Neutravidin to a fraction of the carboxylate residues of a high-molecular weight copolymer of acrylic acid and acrylamide (Scheme 9) using aqueous carbodiimide coupling chemistry (Staros, J.V., Wright, R. W., Swingle, D. M. Enhancement by N-Hydroxysulfosuccinimide of Water-Soluble Carbodiimide-Mediated Coupling Reactions. *Anal. Biochem.* 156, 220-222 (1986)). UV absorbance measurements showed that each macroinitiator contained an average of 140 initiators per chain, and HABA assays (Green, N. M. A spectrophotometric assay for avidin and biotin based on binding of dyes by avidin. *Biochem. J.* 94, 23c-24c (1965)) revealed 1-2 pendant Neutravidins per chain with retention of biotin-binding capability.

The ability of the macrophotoinitiator to recognize biotin-labeled oligonucleotides and to initiate polymerization of water-soluble monomers was tested on thin film biosensors (Jenison, R.; La, H.; Haeberli, A.; Ostroff, R.; Polisky, B. *Clinical Chemistry* 2001, 47, 1894-1900; Jenison, R., Yang, S., Haeberli, A., Polisky, B. Interference-based detection of nucleic acid targets on optically coated silicon. *Nature Biotechnol.* 19, 62-65 (2001); Zhong, X. et al., Single-nucleotide polymorphism genotyping on optical thin-film biosensor chips. *Proc. Natl. Acad. Sci. U.S.A.* 100, 11559-11564 (2003)). These surfaces, because of a specifically designed optical interference layer in the substrate, were ideally suited to testing and optimizing polymerization conditions since films as thin as 5 nm result in an easily observable color change of the surface from gold to blue (Jenison, R.; La, H.; Haeberli, A.; Ostroff, R.; Polisky, B. *Clinical Chemistry* 2001, 47, 1894-1900). Further, the color of the film is a direct measure of the thickness of the film, and hence, a quantitative measure of the amount of polymer that is formed.

A 2×2 oligonucleotide array was spotted on thin film biosensors. The spots in the first column contained biotinylated oligos (5 femtomoles in the upper spot, and 0.5 femtomoles in the lower spot), while the spots in the second column contain unlabeled oligos. Following a 10 minute dose of 5 mW/cm$^2$, 365 nm light, polymer grew only from the two spots containing biotinlyated oligonucleotides (5 fmoles and 0.5 fmoles) and did not grow from the two spots containing unlabeled oligonucleotides. The polymer spots rapidly exceeded 100 nm in thickness, below which the surfaces would yield quantitative information on the amount of polymer. Thus, the unique optical properties of the surfaces were not necessary for detecting a positive response as all polymer films beyond 100 nm appear white. The special optical properties of the surfaces were, however, useful for assessing the occurrence of bulk polymerization or nonspecific polymerization, as even small amounts of polymer would cause a color change on the surface. Color changes were not observed, indicating the lack of both false negatives and bulk polymerization. A negative control chip was subjected to identical conditions except for a lack of exposure to the macrophotoinitiator. No polymerization resulted (at or above the visible limit of 5 nm), ruling out concerns that a molecule other than the macroinitiator initiated polymerization.

Figure 6A:
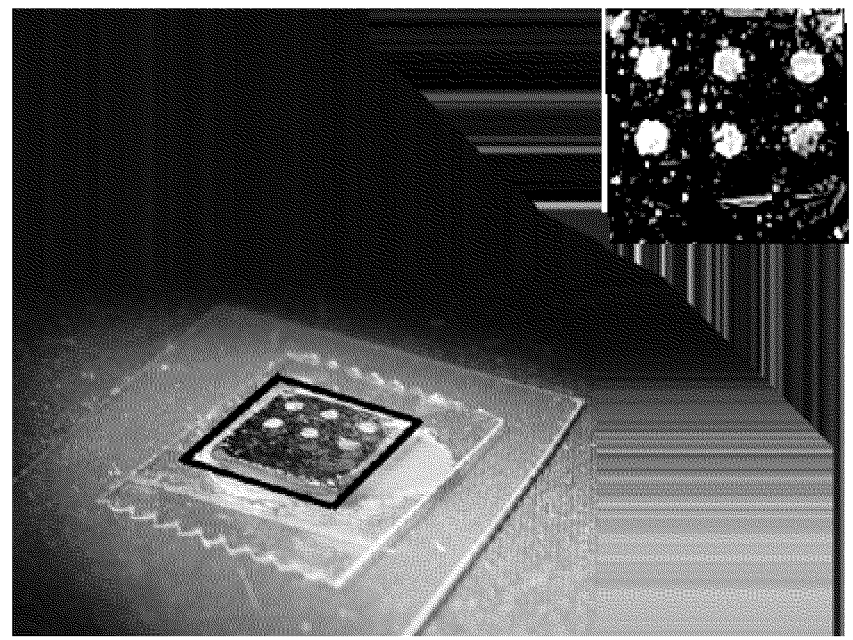
FIGS. 6a-6c illustrate polymerization results for a 3×3 array of biotinylated oligomers; each spot has a different oligomer concentration.
Figure 6B:
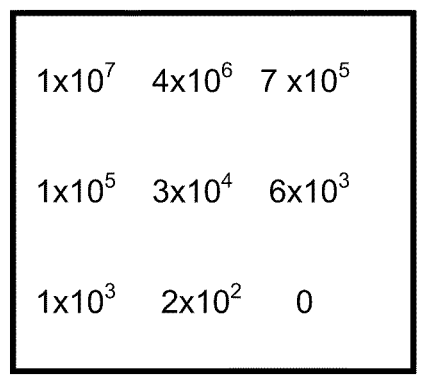
Figure 6C:
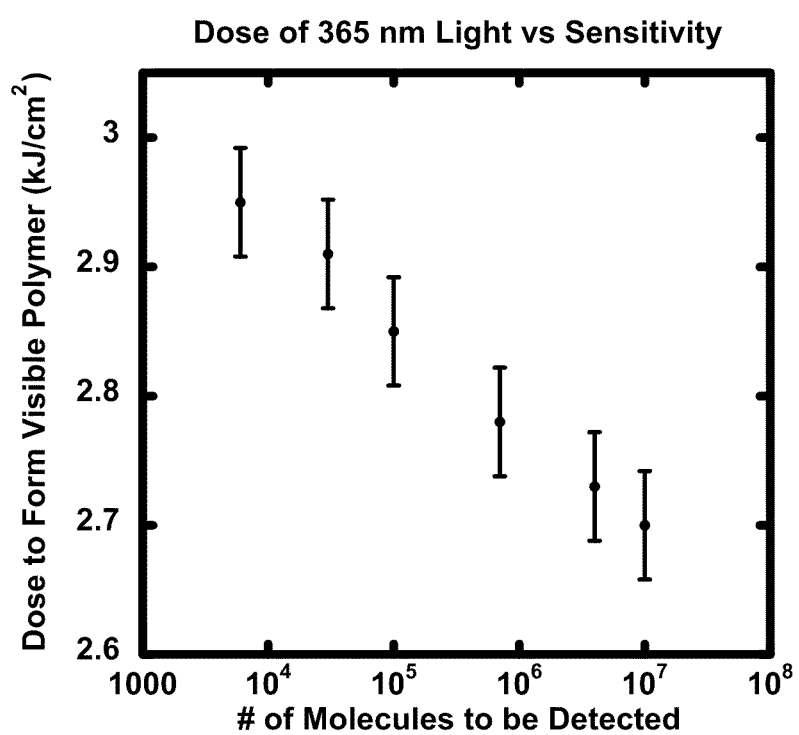

To determine a detection limit for surface-bound oligonucleotides, a dilution chip was prepared with spots containing from femtomoles to zeptomoles of biotinylated oligos. A negative control spot containing only unlabeled oligos was included on the chip. FIGS. 6a-6c show the results obtained using photopolymerization for signal amplification. As shown in FIG. 6a, polymer spots were visible over the first six spots in the array following a 10 minute incubation with avidin-functionalized macroinitiator and a 10 minute dose of 5 mW/cm$^2$, 365 nm light. Using enzymatic amplification (HRP/TMB-dextran), only the first two spots were visible. FIG. 6b shows the maximum number of biotinylated oligos present in each spot. The bottom right spot contained only unlabeled oligos and served as a negative control. FIG. 6c shows the minimum radiation dose that was delivered to each spot prior to observation of polymer formation, where the dose is a product of the light intensity and exposure time. The error bars reflect variations in the intensity output from the lamp as measured with a radiometer.

The most dilute spot that is detected through the formation of a visible amount of polymer contains on the order of 1000 biotinylated oligonucleotides, orders of magnitude fewer than the numbers that are detectable using enzymatic amplification methods. The picture shown in FIG. 6a is representative of twenty trials; no false positives or false negatives (above the limit of detection) occurred.

Further, with constant light intensity exposure, spots containing varying concentrations of the analyte do not appear simultaneously. Rather, as the surface-localized polymerization reactions progress, spots containing higher concentrations of biotinylated oligonucleotides become visible before spots with lower concentrations of biotinylated oligonucleotides become visible. FIG. 6c shows the dose of light that was necessary to see each spot. This response of lower concentrations polymerizing with larger irradiation doses was observed in a differentiable manner across more than three orders of magnitude in analyte concentration. This outcome provides a facile means for converting qualitative detection schemes into a technique that is readily able to quantify the amount of an analyte present at these levels. Simply by changing the exposure time systematically across an array of sample spots, for example by the movement of an opaque film across the surface, it is possible to quantify an analyte, even at these extremely low levels. Thus, a simple change in exposure time across an array can enable quantitative analysis of the target molecule concentration.

The macroscopic, visible response generated by this small number of possible recognition events is remarkable. Without wishing to be bound by any particular theory, we hypothesize that the large degree of polymerization is a result of high radical initiation rates occurring only at the desired surface while radicals that propagate into the bulk do not encounter radicals that lead to termination. The large degree of polymerization is believed to be further enhanced by the formation of a crosslinked, hydrogel polymer. Here, the monomer formulation was optimized to contain a crosslinking agent that hinders radical termination and facilitates the formation of extremely large amounts of polymer from each radical generated.

The relationship between the color of the spot and the thickness of the thin film within the spot has been reported previously; white spots correspond to film thicknesses of at least 100 nm (Jenison, Nature Biotech 2001). Using this thickness as a lower limit for the thicknesses of the polymer spots in FIG. 6a, combined with knowledge of the number of possible binding events and the density of the polymer, we calculate a minimum amplification factor of $10^{11}$ monomers polymerized per binding event in the most dilute spot in FIG. 6a. The density of biotinylated biomolecules in the last visible spot is ~0.005 per $\mu m^2$; this density is below the limit of detection of even the newest high-end fluorescence scanners, instruments that cost tens of thousands of dollars.

False positives are a substantial concern with any signal amplification approach to detection. Though we did not encounter problems with false positives in this study, the result shown in FIG. 6c provides evidence that should false positives arise with more complex samples or recognition pairs that have less specificity than avidin and biotin, it would be possible to shift the threshold of the positive response to exclude nonspecific interactions by selecting an appropriate dose of light. Specificity of detection reagents is a limitation in many diagnostic assays, including ELISAs. Usually, it is not the enzymatic amplification step that limits sensitivity in these assays, but rather, the antibody specificity. In this study, we compared the "top" enzymatic amplification step employed in many ELISA sandwich assays with polymerization-based amplification. This comparison, in which polymerization provided an improvement in sensitivity by orders of magnitude. The exciting and rapidly progressing discoveries directed toward improving the specificity of detection reagents (Jayasena, S. D. Aptamers: an emerging class of molecules that rival antibodies in diagnostics. Clin. Chem. 45, 1628-1650 (1999); Binz, H. K, Amstutz, P., Pluckthun, A. Engineering novel binding proteins from nonimmunoglobulin domains. Nature Biotechnol. 23, 1257-1268 (2005); Brandt, O., Hoheisel, J. D. Peptide nucleic acids on microarray and other biosensors. Trends in Biotechnology 22, 617-622 (2004); Liu, H., et al. A four-base paired genetic helix with expanded size. Science 302, 868-871 (2003); Boder, E. T., Midelfort, K. S., Wittrup, K. D. Directed evolution of antibody fragments with monovalent femtomolar antigen binding affinity. Proc. Natl. Acad. Sci. 97, 10701-10705 (2000)) promise to make our findings more broadly applicable in the coming years.

Macrophotoinitiator Synthesis and Characterization

Initiators and proteins were linked to the —COOH groups of a high molecular weight copolymer of acrylic acid and acrylamide through ester linkages (initiators) and amide linkages (proteins). Though the acrylamide subunits were not involved in the conjugation reaction, their presence was important in the surface bound detection results shown in FIGS. 6a-6c (macroinitiators made with an acrylic acid starting material in the place of poly(acrylic acid-co-acrylamide) do not function similarly). The ratio of acrylic acid to acrylamide can be approximately 1:4 (n:m) Scheme 9 illustrates the synthesis.

A 1 mg/ml solution of N-hydroxy succinimide (NHS) (Aldrich) in 0.1M MES (2-Morpholinoethanesulfonic acid) 0.5 M NaCl buffer, pH 6 and a 1 mg/ml solution of the commercial initiator Irgacure 2959 (Ciba) in distilled water were prepared and placed on a vortexer for 10 minutes until fully dissolved. 0.8 mg of poly (acrylic acid co-acrylamide) (200,000 MW, Aldrich) and 1 mg of the coupling agent 1-Ethyl-3-(3-dimethylaminopropyl)-carbodiimide (EDC) (Aldrich) were weighed out during this time. 260 µL of the NHS solution was pipetted into the tube containing 0.8 mg of poly (acrylic acid co-acrylamide). 1 ml of MES buffer was quickly added to the tube containing 1 mg EDC, and 440 µL of this solution was quickly added to the tube containing NHS and poly (acrylic acid co-acrylamide). This solution was placed on a shaker on a low setting for 15 minutes to allow time for activation of the carboxylic acids of poly (acrylic acid co-acrylamide) by EDC and NHS. 685 µL of the initiator solution and 50 µL of a 10 mg/ml Neutravidin solution (Pierce, Neutravidin is a deglycosylated form of avidin) were added to the activated poly (acrylic acid co-acrylamide) solution, and the reaction was allowed to proceed on a shaker on a low setting for one hour and forty-five minutes. At this time, the high molecular weight product was separated from unreacted smaller molecules using a 100,000 molecular weight cutoff filter (Millipore) and a centrifuge. The spin rates and times recommended by Millipore were used. Purified products were brought up to 500 µL total volume with MES buffer, and UV spectra were collected. A calibration curve of initiator absorbance as a function of concentration was made and used to determine the average number of initiator substituents per macrophotoinitiator. HABA assays were performed as described in Green et al. (Green, N. M. A spectrophotometric assay for avidin and biotin based on binding of dyes by avidin. Biochem. J. 94, 23c-24c (1965).) to determine the average number of Neutravidin substituents per macrophotoinitiator, and to verify retention of biotin binding capability. In our hands, this reaction was very sensitive to any deviation from the above procedures. The non-standard stoichiometry of reactants described above was reached empirically. Initial stoichiometry was 1× poly (acrylic acid co-acrylamide): 1000× photoinitiator: 1000× EDC: 1000× NHS: 1× Neutravidin; however, using this stoichiometry the resulting product was a crosslinked hydrogel that was not useful. NMR was also used to verify the product of the above reaction. Note regarding macroinitiator design: Commercial photoinitiators are commonly used as ~1% by weight additives in bulk polymerizations, a concentration many orders of magnitude higher than could be expected in this new application, particularly near the desired detection limit. Their UV extinction coefficients are sufficiently low that one-initiator-per-binding-event molecules were unlikely to result in large degrees of polymerization. In addition, the polymerization rate is proportional to the square root of the initiator concentration. As a result of these two considerations, we opted to synthesize macromolecules that contained a high ratio of photoinitiator substituents to recognition substituents.

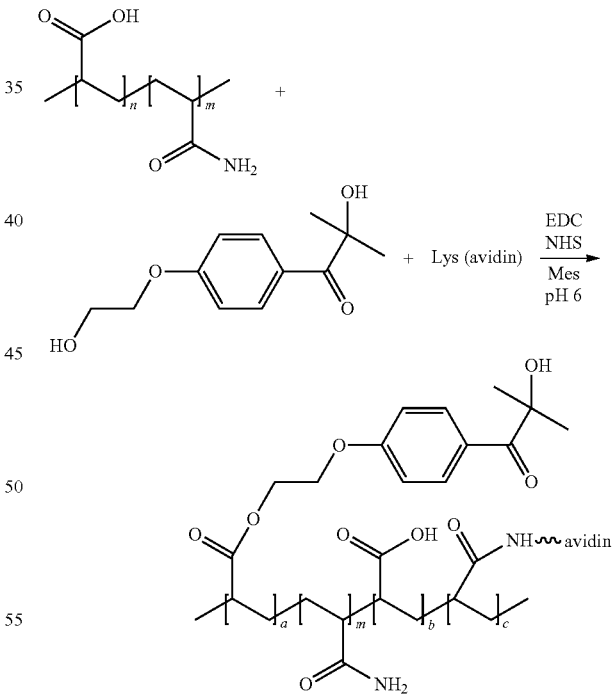

Scheme 9

A standard curve of initiator absorbance as a function of concentration was prepared. The solvent was MES buffer at pH 6 (0.1M MES, 0.5 M NaCl). Absorbance measurements of purified macroinitiator solutions (100 µg/ml in MES buffer) were made, and the standard curve was used to determine the concentration of the initiator in the unknown product solution. The measured absorbance value was 0.7 for 0.5 ml of 100 µg/ml of the macroinitiator.

HABA assays (Green et al.) were used to determine the average number of Neutravidin substituents and verify retention of biotin-binding capability. HABA forms a complex with avidin that absorbs at 500 nm. Biotin displaces HABA due to the stronger affinity of the biotin-avidin interaction and as a result the absorbance at 500 nm decreases. The amount of biotin that had to be added to a solution of the purified macroinitiator (in MES buffer at pH 6) in order to make the shoulder in the absorbance spectrum disappear allowed calculation of the amount of avidin that was covalently attached to the macroinitiator.

1H NMR spectra were collected using samples comprised of 20 mg of the macroinitiator dissolved in 0.7 ml of deuterium oxide. The water peak was pre-saturated for collection of the spectra. NMR analysis requires a larger scale synthesis (60-fold compared with the description in the Methods section), and a methanol precipitation step was more practical in this case than purification with molecular weight cutoff (MWCO) filters. MWCO filters performed well for solutions of this product with concentrations of 1 mg/ml or less, but they did not provide good separation with higher product concentrations.

Arrays.

Optical thin film biosensor (Inverness Medical-Biostar) surfaces were prepared and oligonucleotides were covalently coupled to the surfaces through hydrazone linkages according to previously published procedures (. Zhong, X. et al., Single-nucleotide polymorphism genotyping on optical thin-film biosensor chips. *Proc. Natl. Acad. Sci. U.S.A.* 100, 11559-11564 (2003).). In this reference, wafers were spin-coated with a layer of T structure aminoalkylpolydimethylsiloxane (TSPS) and poly (Phe-Lys) was passively adsorbed to the TSPS layer to facilitate covalent attachment of biomolecules.

To make the dilution chip shown in FIG. 6a, spotting solutions were delivered to the surface in 60 nL droplets using a robotic microarrayer (custom instrument, Biodot); the resulting spots measured approximately 600 μm in diameter. Biotinylated oligos were diluted into spotting solutions containing unlabeled oligos so that the total oligo concentration remained constant across the array.

Enzymatic Amplification.

Detection of biotinylated oligos using enzymatic methods was accomplished by incubating thin film biosensors with 50 μl of a 1 mg/ml solution of anti-biotin-HRP conjugate (Jackson ImmunoResearch Laboratories) in a buffer comprised of 5×SSC, 0.1% SDS, and 0.5% BlockAid™ (Invitrogen-Molecular Probes) for 10 minutes. Following thorough rinsing with 0.1×SSC buffer, thin film biosensors were incubated with 60 μl of a TMB/dextran solution (BioFX Laboratories) for 15 minutes. After rinsing with distilled water, thin film biosensors were visually inspected for a color change from gold to blue (Jenison, R., Yang, S., Haeberli, A., Polisky, B. Interference-based detection of nucleic acid targets on optically coated silicon. *Nature Biotechnol.* 19, 62-65 (2001).

Polymerization-Based Amplification.

Detection of biotinylated oligos using photopolymerization was accomplished by incubating thin film biosensors with 50 μl of a 1.6 mg/ml solution of a macrophotoinitiator in a buffer comprised of 5×SSC, 0.1% SDS, and 0.5% BlockAid™ (Invitrogen-Molecular Probes) for 10 minutes. No steps were taken to protect the macroinitiator from ambient light; it is stable under ambient light conditions. Immediately following rinsing with 0.1×SSC buffer, while the surfaces were still wet, 50 μl of an argon-purged monomer solution (97% by weight hydroxyethyl acrylate and 3% by weight ethyleneglycol dimethacrylate crosslinker, each triply distilled to remove inhibitors) was pipetted over the entire array. Polymerization from spots containing biotin and bound macrophotoinitiator was accomplished using a 10 minute dose of 5 mW/cm$^2$ UV light centered around 365 nm from a Blak-Ray B Series-100A lamp. The percent of the crosslinker in the monomer formulation and the dose of radiation were optimized by systematic variation of each. Polymerized arrays were photographed with a digital camera without any rinsing or other post-polymerization treatment. The resulting hydrogel was susceptible to damage from rinsing to remove unreacted monomer Further details are given in Sikes, H. S.; Hansen, R. R.; Johnson, L. M.; Jension, R.; Birks, J. W.; Rowlen, K. L.; Bowman, C. N. *Nature Materials* 2007, 7, 52-56, hereby incorporated by reference.

Example 12

Recognition Between Biotinylated Oligonucleotide Arrays and Streptavidin Functionalized with Photoinitiator A rapid (20 minute), non-enzymatic method of signal amplification utilizing surface-initiated photopolymerization is presented in glass microarray format. Visible light photoinitiators covalently coupled to streptavidin were used to bind biotin labeled capture sequences. Amplification was achieved through subsequent contact with monomer solution and the appropriate light exposure to generate 20 to 240 nm thick hydrogel layers exclusively from spots containing the biotin labeled DNA. An amplification factor of $10^6$-$10^7$ was observed as well as a detectable response generated from as low as ~$10^4$ labeled oligonucleotides using minimal instrumentation, such as an optical microscope or CCD camera. This corresponds to a visual limit of about 10 biomolecules/μm$^2$.

Polymerization-based amplification methods were extended to visual detection of biotin-labeled DNA functionalized on glass microarray surfaces with the use of photoreducible dyes which initiate upon visible light exposure. We chose Eosin Isothiocyanate (EITC) as our photoinitiator due to its favorable absorption characteristics and demonstrate its ability to transduce biomolecular recognition into a macroscopically observable response in a highly sensitive manner. A tertiary amine coinitiator is added to bulk monomer to generate free radicals for polymerization of a polyethylene glycol diacrylate (PEGDA) monomer solution. Similar systems have previously been reported for surface initiated polymerization from silica nanoparticles (Satoh, M.; Shirai, K.; Saitoh, H.; Yamauchi, T.; Tsubokawa, N. *Journal of Polymer Science:Part A: Polymer Chemistry* 2005, 43, 600-606), from aminosilinated glass surfaces for photopatterning applications (Kizilel, S.; Perez-Luna, V. H.; Teymour, F. *Langmuir* 2004, 20, 8652-8658; Kizilel, S.; Sawardecker, E.; Teymour F.; Perez-Luna, V. H. *Biomaterials* 2006, 27, 1209-1215; Kizilel, S.; Perez-Luna, V. H.; Teymuor F. *Macromolecular Theory and Simulations* 2006, 15, 686-700), and in cell encapsulation studies (Cruise, G. M.; Hegre, O. D.; Scharp, D. S.; Hubbell, J. A. *Biotechnology and Bioengineering* 1998, 57, 655-665). Demonstration of DNA detection from polymerization-based signal amplification on general microarray surfaces enables use as a detection method in applications commonly found in microarray technology, such as single nucleotide polymorphism screening (Urakawa, H.; Noble, P. A.; El Fantroussi, S.; Kelly, J. J.; Stahl D. A. *Applied and Environmental Microbiology* 2002, 68, 235-244; Peterson, A. W.; Wolf, L. K.; Georgiadis, R. M. *Journal of the American Chemical Society* 2002, 124, 14601-14607). and should be

*directly applicable to implementation on commercially available microarray platforms (Hardiman, G. Pharmacogenomics 2004, 5, 487-502).*

Microarray Fabrication.

Commercially available amino or aldehyde functionalized glass substrates were purchased from CEL associates and all slides were stored in vacuum at room temperature. The surface was spotted through pin deposition using a solid pin to deposit ~570 μm diameter spots and a quill pin for ~100 μm diameter spots at 75% humidity. An oligonucleotide sequence (5' amino—CATCACACAACATCACACAACAT-CACGTATATAAAACGGAACGTCGAAGG-3' TEG biotin) (Operon) was spotted at an overall concentration of 20 μM on aldehyde substrates in the spotting buffer (3×SSC, 0.05% SDS) using a VersArray ChipWriter Pro system made by Bio-Rad Laboratories. The identical, unlabeled capture sequence was spotted on the surface at a concentration of 4 μM, which has been shown to be optimal for hybridizations. These slides were left in humidity for 24 hours. Aminosilane slides were spotted with 4 μM concentrations of 5' biotin, 5' Cy3, or unlabeled versions of this same sequence with varied concentrations of labeled sequences present for fabrication of dilution chips. These were left in humidity for 30 minutes, then dried in an oven at 80° C. for 2 hours and finally crosslinked to the surface using a 254 nm light. All spotted slides were stored at −18° C. until use.

Photoinitiator Synthesis.

The visible light photoinitiator Eosin-5-Isothiocyanate (Invitrogen) was functionalized directly onto external lysine residues of streptavidin through formation of a thiourea bond (Hermanson, G. T. Bioconjugate Techniques; Academic Press: San Diego, 1996) according to the reaction shown in scheme 10:

Streptavidin was dissolved in carbonate buffer (0.10 M NaCO₃, pH 9) at a concentration of 10 mg/mL. A 10 mg/mL solution of EITC in DMSO was prepared and immediately added to streptavidin at a volumetric ratio of 1:10. The solution was reacted for 8 hours at 4° C., then diluted to a streptavidin concentration of 1 mg/mL in 1× PBS and purified using gel filtration. The product was characterized with conventional UV-Vis spectroscopy, and the characteristic peak from EITC at 525 nm was compared to the characteristic protein peak at 280 nm according to equation 3:

$$n_{EITC}/n_{SA} = \frac{\text{Abs}_{EITC,525}/\varepsilon_{EITC,525}}{(\text{Abs}_{SA,280} - \text{Abs}_{EITC,280})/\varepsilon_{SA,280}} \qquad (3)$$

Measuring 0.2 mg/mL solution of the product diluted in 1× PBS buffer, an average photoinitiator to protein ratio of 2.3 was observed. The product was stored at 4° C. and protected from light exposure until further use.

Microarray Functionalization of Photoinitiator Product.

Spotted slides were blocked with 2 weight percent dry milk in ddH₂0 for 2 hours to prevent nonspecific adsorption of the photoinitiator product to the surface. Slides were then rinsed with water and contacted with 200 μL at 1 μg/mL of visible photoinitiator product in 1× PBS and 5× Denharts solution for 30 minutes. Slides functionalized with streptavidin-EITC were either placed in boiling water for two minutes or washed in TNT solution (1M NaCl, 0.1M Tris, 0.1 wt % Tween 20) to remove nonspecific protein adsorbed on the surface. Slides were rinsed in ddH₂0 and allowed to dry.

Surface-Initiated Photopolymerization.

MEHQ inhibitor was removed from poly (ethylene glycol) diacrylate (PEGDA) ($M_n$~575 Da) with the use of a dehibit

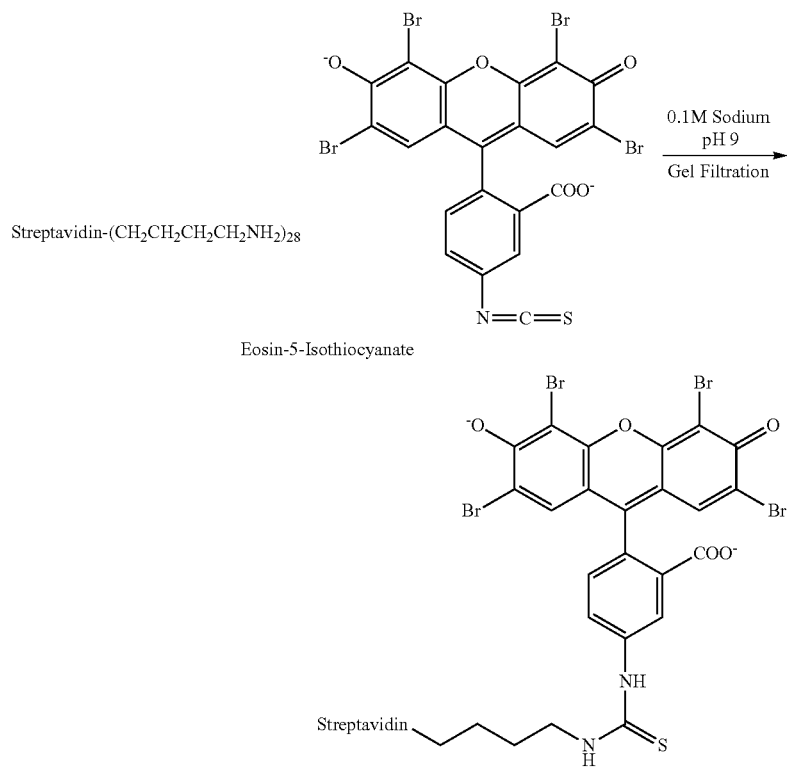

column (Sigma). Methyl diethanol amine (MDEA) and 1-vinyl-2-pyrolidinone were used as received. The reactive monomer solution consisted of 25 wt % PEG(575)DA, 225 mM MDEA, 37 mM 1-vinyl-pyrolidinone in a ddH$_2$O solvent. The pH was about 9. 300 μL of one of the monomer solutions was purged with argon, then contacted with the surface using a Whatman Chip Clip. Slides were placed in an argon chamber that was continuously purged for 5 minutes prior to radiation. A 400-500 nm Novacure collimated light source was used to radiate the streptavidin-EITC functionalized slides at 8 mW/cm$^2$ for 20 minutes. The samples were gently rinsed with ddH$_2$O to remove unreacted monomer and then dried with argon.

Post-Polymerization Surface Characterization of Microarray Surface.

A surface profilometer (Dektak 6M) was used to obtain height profiles of the films that were visible on the array after drying the chips such that the hydrogels was completely dehydrated. Stylus force was set at a minimum (1 mg) to minimize mechanical deformation of the hydrogel layers from the 12.5 μm diamond stylus tip. An infrared microscope was used to obtain IR spectra of surface bound moieties. An Agilent Technologies DNA Microarray Scanner was calibrated at specific settings (100% PMT Gain) with a Cy3 calibration chip obtained from Full Moon Biosystems and used for fluorescent imaging.

Fluorescent Imaging of Photoinitiators on Surface.

As an initial characterization of the amplification processes, aldehyde functionalized microarray surfaces were spotted with rows of 5' amino, 3' biotin functionalized capture sequences and rows of 5' amine capture sequences without the biotin label. Upon incubation of 1 μg/mL concentrations of Streptavidin-EITC, photoinitator molecules should be localized to the labeled capture sequences with the strong affinity of biotin-streptavidin complex ($K_d$=10$^{-15}$). Eosin, a weak fluorophore with a fluorescence quantum yield of 0.19 (Weber, G.; Teale, F. W. J.; *Transactions of the Faraday Society* 1957, 646-655), has a strong absorbance at 532 nm, an excitation source used by most conventional microarray scanners. Thus, fluorescent scanning was used to quantify the number of biotin-streptavidin binding events on the surface as well as background from non-specific protein interactions. A fluorescent image of a microarray containing 3' biotin labeled capture sequences and unlabeled capture sequences after streptavidin-EITC incubation but prior to amplification shows that the average fluorescent signal of positive spots containing streptavidin-EITC molecules is 26,000 while unlabeled sequences show low fluorescent counts of 400 and average background of 350 fluorescent counts, close to machine noise (325). Fluorescent intensities show uniform signal both within individual spots (Standard Deviation = 3260) and between duplicate spots (Standard Deviation=3060).

Upon quantification of the fluorescent intensity at the positive spots minus background absorbance, there are 480+/− 60 eosin fluorophores per μm$^2$. Because the number of fluorescent eosin molecules per streptavidin protein was determined as 2.3, there is an average of 200 biotin—streptavidin binding events per μm$^2$ at positive sites on the biochip. The variance in signal intensity of <15% relative standard deviation both in average fluorescent counts between positive spots and between counts within individual spots, giving evidence of relatively monodisperse allocation of photoinitators on the surface. This monodispersity is achieved primarily from use of optimized spotting buffer during the printing process and contacting the streptavidin-EITC solution on the surface without the use of a coverslip. Because of the monodispersity attained here, a uniform number of radicals is eventually generated across the positive spots during the surface initiated photopolymerization process to aid in generating polymer films of uniform thickness.

Surface Initiated Photopolymerization with Visible Light.

Upon functionalization of streptavidin-EITC, rapid amplification was performed by contact with monomer and light exposure to generate propagating radicals for amplification at the solid-liquid interface. Using a 25 wt % solution of PEG (575)DA monomer with a 225 mM MDEA coinitiator and 37 mM 1-vinyl-2-pyrollidone accelerator in an aqueous solvent has been shown to form stable, micron thick hydrogels on EITC functionalized aminosilinated glass surfaces (Kizilel, S.; Perez-Luna, V. H.; Teymour, F. *Langmuir* 2004, 20, 8652-8658). The presence of difunctional acrylate yields pendant double bonds in propagating polymer chains that may crosslink with other propagating chains, thus suppressing chain termination rates and causing large amounts of high molecular weight polymer to be generated at positive sites.

Attachment of the PEG hydrogel to the surface is achieved through termination reactions between surface stabilized eosin radicals and bulk radicals present on PEGDA chains (Kizilel, S.; Perez-Luna, V. H.; Teymour, F. *Langmuir* 2004, 20, 8652-8658). In this application, strong attachment of the polymerized hydrogel layer to the surface was critical to avoid delamination from swelling during washing to remove unreacted monomer. After amplification using visible light (400-500 nm, 8 mW/cm$^2$, 20 minutes) and subsequent washing, highly visible, surface stabilized hydrogel films have been observed exclusively over biotinylated sites. The stabilization to the surface is achieved here through the high affinity streptavidin-EITC binding to covalently bound biotin. To verify that the macroscopic response observed was due to surface initiated photopolymerization of the hydrogel precursor solution at biorecognition sites, the visible polymer spots on the microarray surface were characterized through FTIR analysis. Film deposition of sub micron-scale thicknesses yields an IR spectra characteristic of the polymeric moiety stabilized to the glass surface above a wavenumber of 2000 cm$^{-1}$. An optical microscope image of spots on the array shows surface initiated polymerization of a PEG hydrogel networks exclusively at biorecognition sites. The microscope image shows the consistent formation of well-defined polymer spots only where 3' biotin labeled capture sequences were present. Non-specific polymerization from the background or from unlabeled capture sequences is not observed. IR spectra generated from positive spots on the chip and at regions outside the spots also gives evidence of the surface initiated polymerization of a PEG hydrogel networks exclusively at biorecognition sites. Upon the formation of a polymer layer over biotinylated oligonucleotide spots, infrared peaks characteristic of hydroxy groups (broad peak from 3200 to 3550 cm$^{-1}$) and alkyl groups (peak at 2900 cm$^{-1}$) present in PEG hydrogel become clearly visible. In areas on the chip outside the visible spots, no peaks are detectable.

To verify that these films were indeed polymerized only due to biotin/photoinitator binding, monomer contact, and light, several negative controls were performed on glass surfaces. No polymerization was observed without incubation of the initiator or without light exposure, consistent with what was previously observed on Biostar chips (Sikes, H. S.; Hansen, R. R.; Johnson, L. M.; Jension, R.; Birks, J. W.; Rowlen, K. L.; Bowman, C. N. *Nature Materials* 2007, doi: 10.1038/nmat2042).

Film Thickness Measurement and Amplification Factor Determination.

To characterize the polymer films further on the biochip surface, film thicknesses were measured through the use of profilometry. Such an analysis will allow for investigation of the uniformity of the polymer film thickness both between positive spots and within each spot, as well as an estimation of the number of monomers polymerized at each positive location. With the quantification of both the number of binding events of streptavidin-EITC on the surface and the film thickness of the resulting polymer films, an amplification factor, defined as the average number of propagation reactions occurring per biorecognition event, is readily estimated. FIGS. 7a and 7b show profilometry scan across spots containing 3'biotin labeled capture sequences (A) and unlabeled capture sequences (B). Both rows contained capture sequences at a surface density of $10^2$ capture sequences/$\mu m^2$. Average film thickness generated from the 3'biotin labeled capture sequence was 140 nm, with a standard deviation of 20 nm between spots and a similar standard deviation of 20 nm between film thickness measurements within a single spot. Nonspecific amplification has been eliminated in the amplification system both in the background and from unlabeled DNA. No signal was detectable above profilometer error (10 nm) from spots containing the unlabeled capture sequences on the same biochip. FIG. 7a shows a representative profilometry scan across a section of the biochip surface containing positive spots signaling the presence of 3' biotinylated capture sequences. Apparent in FIG. 7a are well-defined step functions generated from the polymer films, in 570 $\mu m$ spots ranging from 110 nm to 160 nm in thickness. No significant change of spot diameter from the polymerization was incurred, as determined from comparison of spot diameters from the fluorescent image before amplification with the profilometry measurement after amplification. The uniformity measured in each peak was due to monodispersity of photoinitiator allocation observed from the fluorescence measurements. However, the 14% relative standard deviation between peaks measured in FIG. 7a may be due to the small variation in photoinitiator surface density, small variations in light intensity across the surface, impurities in the monomer solution, damage to the polymer film during washing, or from the highly amplified nature of free radical polymerizations.

Despite the noted variation in film thickness, the well-defined peak heights measured in FIG. 7a still allow for an estimation of the number of monomers polymerized in each spot. Film thicknesses averaging 0.14 $\mu m$ thick in a 570 $\mu m$ diameter spot give a hydrogel volume of $3.67\times10^4$ $\mu m^3$. Taking the density of poly(ethylene glycol) (1.2 g/cm$^3$) and the average molecular weight of each repeat unit (575 g/mol), $4.61\times10^{13}$ monomers were polymerized per spot ($2\times10^8$ monomers/$\mu m^2$). As determined through fluorescence, streptavidin-EITC binds 200 biotins/$\mu m^2$. Dividing the number of monomers per $\mu m^2$ by the number of biorecognition events per $\mu m^2$ gives a $1\times10^6$ amplification observed on this surface. This amplification factor is comparable to 40 cycles of PCR amplification (Parsons, G. *J. Clin. Immunoassay* 1988, 11, 152-158).

Dilution Chips for Sensitivity Analysis.

To investigate sensitivity of the visible light amplification system, a biochip containing a large variation of labeled target oligo surface densities was developed on aminosilated glass surfaces. Aminosiliated surfaces were chosen in fabrication of dilution chips as opposed to aldehyde modified glass because a larger range of oligonucleotide surface densities were obtainable on aminosilated surfaces. On these dilution chips, the surface concentration of labeled oligo decreased with each row of spots. To achieve this dilution, a constant overall spotting concentration of oligonucleotide at 4 $\mu M$ was desired with the amount of labeled oligo decreasing from 4 $\mu M$ to 1.25 nM. Using Cy3 as the label at these spotting concentrations followed by fluorescent scanning with a 532 nm excitation source, surface densities were determined to range from $10^4$ markers/$\mu m^2$ to <5 markers/$\mu m^2$. The most dilute rows of labeled oligonucleotide were assumed to be 5 markers/$\mu m^2$, the quantifiable detection limit on the scanner. In actuality, the surface density is lower. The final row represents unlabeled oligonucleotide only, as the oligo on the surface shows a small amount of background fluorescence making these spots visible under a scanner. Using a quill pin for spotting, spots are consistently 100 $\mu m$ in diameter, thus the equivalent number of capture oligos in a spot on the surface ranges between 0.2 femtomoles to ~60 zeptomoles in the most dilute spots.

In fabrication of the biotin dilution chips, the end label was switched from Cy3 to biotin, and assumed that nearly identical surface densities would be obtained with the respective spotting concentrations. Because covalent attachment of photoinitiator to the surface has been shown to be required for stable hydrogel layers to remain on the surface during swelling. (Kizilel, S.; Perez-Luna, V. H.; Teymour, F. *Langmuir* 2004, 20, 8652-8658; Revzin, A.; Russel, R. J.; Yadavalli, V. K.; Koh, W. G.; Deister, C.; Hile, D. D.; Mellott, M. B.; Pishko, M. V. *Langmuir* 2001, 17, 5440-5447) 254 nm light exposure was used to form covalent attachment of biotinylated oligonucleotide to the aminosilane layer using a 254 nm light source at an exposure which was known to crosslink the oligo to the surface. A fluorescent image of the dilution chip upon incubation of the streptavidin-EITC visible light initiator at 1 $\mu g/mL$ was obtained. A fluorescent signal gradient is observed, giving evidence of allocation of decreasing amounts of photoinitiator at oligo spots corresponding with decreasing label density. Incubation at 1 $\mu g/mL$ of streptavidin-EITC was considered sufficient for amplification, incubating with higher concentrations may lead to non-specific adsorption of initiator to the surface, either limiting the sensitivity of the amplification or giving the potential to amplify background as well the positive spots. A fluorescent signal that is significantly different than the negative column (unlabeled oligo) can be seen down to the $12^{th}$ column, corresponding to ~0.1 attomoles of surface bound biotinylated oligo. The last three columns containing biotinylated oligonucleotide, as well as the final negative column all show a similarly small fluorescence level due to non-specific protein-oligonucleotide electrostatic interaction, thus non-specific protein adsorption has been minimized but not completely eliminated in this system.

Detection Limit Determination Using Polymerization Based Amplification.

The same hydrogel precursor solution as previously described was applied to the microarray dilution chips with a 400-500 nm, 8 mW/cm$^2$ light exposure. Light intensity and exposure time for use on the dilution chip were chosen from FTIR bulk polymerization studies that showed complete double bond conversion of this hydrogel solution as observed at 6120 cm$^{-1}$ with streptavidin-EITC concentrations ranging from $10^{-5}$ M to as low as $10^{-6}$ M. These concentrations represent the local concentrations of EITC at different rows of positive spots on the dilution chips, given the photoinitiator surface density as determined through fluorescence and assuming a 10 nm film over each spot. After 20 minutes from the beginning of the polymerization, final conversion was reached with a $10^{-6}$ M solution of streptavidin-EITC, representing spots on the dilution chip with the smallest amounts of initiators present. Thus, with this exposure it can be assumed that the final conversion would be achieved when initiating polymerization from all rows at the surface of our biochip.

After polymerization on the dilution chips and washing, spots became consistently visible under an optical microscope or CCD camera to as low as ~0.4 attomole levels of biontylated oligo (10 labeled oligos per μm²), a macroscopically observable response generated from biotin labeled oligonucleotides at surface densities approaching the quantifiable detection limits of most microarray scanners.

observed from fluorescence intensities that reveal the same amounts of initiator allocation prior to amplification on all spots containing less then 0.1 attomoles. Currently, the non-specific interaction is the limiting factor in regards to the sensitivity of the system.

We have demonstrated a method of amplifying a biorecognition event on glass microarray surfaces at high sensitivity through functionalizing surface bound oligonucleotides with photoinitiators, followed by contact of monomer solution and appropriate visible light exposure. The hydrogels formed at

TABLE 2

| Row | 1 | 2 | 3 | 4 | 5 | 6 | 7 | 8 | 9 | 10 | 11* | 12 | 13 | 14 | 15 | 16 |
|---|---|---|---|---|---|---|---|---|---|---|---|---|---|---|---|---|
| Moles of 5'Biotin-DNA ($10^{-18}$) | 237 | 234 | 222 | 207 | 184 | 121 | 109 | 59 | 1.4 | 0.68 | 0.30 | 0.17 | 0.08 | 0.08 | 0.08 | 0.00 |
| +/- Error | 10 | 7 | 5 | 10 | 10 | 7 | 4 | 4 | 0.04 | 0.03 | 0.02 | 0.00 | 0.00 | 0.00 | 0.00 | 0.00 |
| Film Thickness (μm) | 0.20 | 0.13 | 0.20 | 0.20 | 0.24 | 0.20 | 0.22 | 0.24 | 0.11 | 0.06 | 0.08 | 0.08 | 0.01 | 0.02 | 0.02 | 0.02 |
| +/- Error | 0.09 | 0.05 | 0.07 | 0.08 | 0.11 | 0.08 | 0.08 | 0.08 | 0.06 | 0.03 | 0.04 | 0.05 | 0.01 | 0.01 | 0.02 | 0.01 |

*Visual Detection Limit

This detection limit was repeatable using different batches of streptavidin-EITC, monomer, and dilution chips. Average film thicknesses generated from each row on dilution chips are presented in Table 2. Table 2 is a summary of film thicknesses generated from specific quantities of biotinylated oligonucleotide sequences on each of 16 rows on dilution chips using photopolymerization based amplification.

Figure 8A:
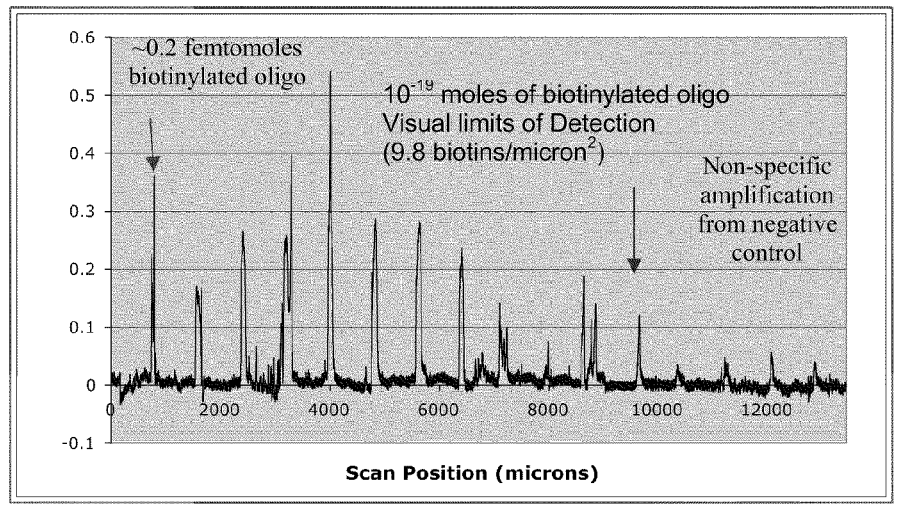
FIGS. 8a and 8b show film thicknesses obtained for rows containing different amounts of biotinylated DNA on a dilution chip using a visible light initiation system.
Figure 8B:
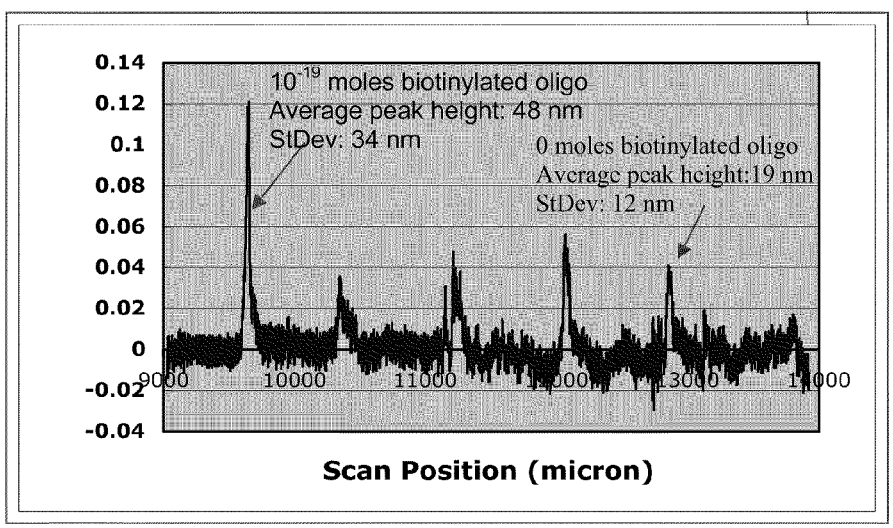

Data was averaged from different batches of reagents and materials that were fabricated several months apart. FIGS. 8a and 8b show film thicknesses obtained for rows containing different amounts of biotinylated DNA on the dilution chip using the visible light initiation system (representative profilometry scan down the rows of the dilution chip). For higher numbers of biotinylated oligonucleotide (~0.2 femtomoles to ~60 attomoles), film thicknesses averaging from 0.2 to 0.3 microns have been observed (FIG. 8a). At lower concentrations of biotinylated DNA, film thicknesses became less then 0.1 microns thick but still remained consistently visible under an optical microscope or a CCD camera down to the 11$^{th}$ row, generated from ~0.4 attomoles of biotinylated oligo (A), below which no other spots were visible. Using profilometry as a means of detection, a statistical difference of film thickness from the negative control has been detected down to the 12$^{th}$ row, containing ~0.1 attomoles (FIG. 8b).

As is shown in FIGS. 8A and 8B a saturation region appears to be present in regards to responses generated from 0.2 femtomoles to 60 attomoles. Peaks generated from 1 to ~0.1 attomoles are consistently less thick and less visible. With profilometry, a peak generated from each of the sixteen rows on the dilution chip is detectable, including that from the negative row containing unlabeled oligonucleotide. Because of the electrostatic interaction between streptavidin-EITC and oligonucleotide that was observed from fluorescence scanning, these peaks may be due to amplification from the non-specific allocation of initiator onto oligonucleotide spots. From FIGS. 8a and b, a statistical difference in film thickness from the negative control corresponding to a 99% confidence level can be shown from as low as 0.1 attomoles (the 12$^{th}$ row). At these lower levels, the estimated amplification factor increases to $10^7$. Peaks from samples below 0.1 attomoles show no significant difference in film thickness from the negative control; this corresponds to what was biorecognition sites polymerized to sub-micron level thicknesses in a matter of minutes, were well-defined with uniform thicknesses, and showed stable attachment to the glass surfaces upon washing to remove unreacted monomer. Minimal background or non-specific amplification was observed on the surfaces. While this amplification system was demonstrated for the detection of biotin-avidin binding, such a system can be readily extended to the detection of complementary nucleic acid hybridization through the use of chemical or enzymatic labeling approaches (Zhong X.; Reynolds, R.; Kidd, J. R.; Jenison, R.; Marlar, R. A.; Ward, D. C. *Proc. Natl. Acad. Sci.* 2003, 100, 11559-11564). For example, polymerase enzymes may be used for labeling 3' ends of hybrid DNA on a microarray surface with labeled dNTPs in a primer extension reaction (Pastinen, T.; Raitio, M.; Lindroos, K.; Tainola, P.; Peltonen, L.; Syvanen A. G. *Genome Research* 2000, 10, 1031-1042; Hultin, E.; Kaller, M.; Ahmadian, A.; Lundeberg, J. *Nucleic Acids Research* 2005, 33, e48). Using biotinylated dNTPs in such a reaction would then render this surface the same as the model surfaces studied in this example. Polymerization-based amplification of complementary DNA hybridization (1 μM target hybridization of K-Ras biomarker) has been demonstrated using this approach.

The generation of macroscopically observable hydrogel spots due to the presence of as low as sub-attomole amounts of labeled genetic material on microarray substrates should allow for at least a sensitive, positive/negative determination to be made without the use of detection equipment. With the rapid, inexpensive, and robust characteristics of this amplification method, photopolymerization for detection of molecular recognition holds considerable potential, as amplification of at least $10^6$-$10^7$ will help facilitate use of molecular diagnostic applications in clinical settings.

Further details are given by Ryan R. Hansen, Hadley D. Sikes, and Christopher N. Bowman, Biomacromolecules, 2008, 9(1) pp 355-362; which is hereby incorporated by reference.

Example 13

Quantification of Oligonucleotide Surface Concentrations and Incorporation of Fluorescent Nanoparticles into Polymer Films Quantitative characteristics of a visible light polymerization-based amplification system were investigated for use in biodetection assays requiring sensitive, sequence-specific detection of polynucleotides. The approach taken involves fabricating biochip surfaces with oligonucleotide spots containing controlled concentrations of immobilized, biotinylated DNA targets capable of capturing proportional amounts of streptavidin-initiator, followed by contact with a monomer solution and a discrete light exposure. Determination of the amounts of amplification generated at each target concentration is evaluated with film thickness measurements, allowing for calibration of film thickness with DNA concentration. While amplification is evaluated in a solid-state biosensor format, the results should also be significant when considering implementation of this amplification system to solution-based assays as well.

To implement inexpensive detection instrumentation for quantification, it is desirable that PEG films with quantitative thicknesses generated from polymerization-based amplification be correlated with a measurable signal consistent with inexpensive methods of detection. Direct film thickness measurements at the nanometer level may be infeasible in clinical settings due to the expense of the necessary instrumentation (profilometry, ellipsometry, atomic force microscopy). Developing this amplification system towards generating an amplified fluorescent signal that corresponds with film thickness is particularly desirable. This is due to the wide range of instrumentation typically available for characterizing biomolecule interactions using fluorescent measurements. For microarrays, such instrumentation ranges from laser based microarray scanners using photomultiplier tube (PMT) detectors (detection limit <0.05 fluors/$\mu m^2$, $10^6$ dynamic range), costing hundreds of thousands of dollars to fluorescent readers employing inexpensive excitation sources (such as a 10 mW, 532 or 635 nm laser pointers) and CMOS detectors with associated equipment cost less than $1000 and with minimal power requirements (detection limit ~5000 Cy3 fluors/$\mu m^2$). With these considerations in mind, an initial demonstration of using polymerization-based amplification to achieve an amplified, quantitative fluorescent signal is demonstrated herein.

One approach to coupling fluorescent signal with polymer growth is to include the fluorescent moiety in the monomer formulation such that it is copolymerized or encapsulated into the crosslinked polymer network. With the commercial availability of several types of acrylated-fluorophores, copolymerization of molecules such as fluorescien-o-acrylate into PEG-based polymer films on a solid substrate has been demonstrated as a method of coupling a fluorescent response to hydrogel formation (Kizilel, S.; Sawardecker, E.; Teymour F.; Perez-Luna, V. H. Biomaterials, 2006, 27, 1209-1215). In application to photopolymerization-based amplification, several limitations to such approaches are inherent, namely non-specific initiation of bulk monomer due to photoreduction reactions occurring between a photoexcited fluorophores and amine coinitiators; secondly, decreased initiation rates from the surface-bound eosin initiators due to light attenuation to the surface caused by the absorbing fluorophore; and finally, saturation of fluorescent signal after amplification due to quenching of fluorescent molecules at higher concentrations.

An alternative to fluorescent acrylates are commercially available, 20 nm diameter polystyrene microspheres that encapsulate ~$10^2$ hydrophobic fluorophores per particle (Invitrogen). These fluorescent particles mitigate many of the above limitations largely due to the fact that they eliminate fluorophore contact with their surrounding environment and remain strongly fluorescent.

Dilution chip development. Oligonucleotide arrays were characterized by spotting decreasing concentrations of 5' Cy3 functionalized 50 base oligonucleotides (Operon) on aminosilated glass (CEL Associates) using a 375 $\mu$m diameter stealth solid pin (Arraylt) and quantifying the surface concentrations through fluorescence scanning (Hansen, R. R.; Sikes, H. D.; Bowman, C. N. Biomacromolecules, 2008, 9, 355-362). The dilution array contained decreasing amounts of 3' biotinylated oligonucleotide diluted in a solution of unlabeled oligonucleotide capture probes such that the overall concentration of oligonucleotide remains constant at 4 $\mu$M. Dilution chips were fabricated to capture a three order of magnitude range of surface densities with an even distribution of intermediate surface densities to allow for a comprehensive evaluation of film thicknesses generated from polymerization based amplification. The specific concentrations used were: 4 $\mu$M, 3 $\mu$M, 2 $\mu$M, 1 $\mu$M, 530 nM, 270 nM, 130 NM, 78 nM, 53 nM, 40 nM, 30 nM, 20 nM, 10 nM, 5 nM, 2.5 nM, 0 nM.

In actual fabrication, 5' biotin triethylene glycol was replaced as the label. Slides were dried at 85° C. for 1 hour and then exposed to 254 nm light to couple capture sequences onto the amine attachment layer. Slides were then washed with water to remove buffer salts and stored at −20° C. until further use.

Functionalization and characterization of streptavidin—eosin isothiocyanate. Streptavidin-eosin isothiocyanate (SA-EITC) was synthesized, purified, and characterized according to previously published protocol (Hansen et al., 2008). Dilution chips were functionalized with SA-EITC by applying a mixture of unlabeled streptavidin (Pierce) and SA-EITC at 1 $\mu$g/mL for concentration for 30 minutes followed by washing with TNT solution (1M NaCl, 0.1M Tris, 0.1 wt % Tween 20) and then drying with $N_2$. Preamplified, SA-EITC functionalized dilution chips were characterized using an Agilent Microarray scanner (green channel, 100% PMT) calibrated using a Cy3/Cy5 calibration chip (Full Moon Biosystems). Denharts solution was used as a blocking agent.

Monitoring of Bulk Polymerization Kinetics.

The initiating capability of SA-EITC in various monomer formulations was verified by monitoring bulk polymerization through the use of Fourier transform infrared (FTIR) spectroscopy. The double bond conversion at 6120 to 6210 $cm^{-1}$ was monitored using monomer formulations (25 wt % PEGDA, $M_n$=575 Da, 225 mM methyl diethanol amine coinitiator, 37 mM 1-vinyl-2-pyrolldinone, in $H_2O$, pH 9) containing 50 ng/mL SA-EITC initiator (1 $\mu$M eosin concentration) and specified concentrations of Nile Red FluoSpheres (Invitrogen) in a sample with a 2 mm pathlength.

Polymerization based amplification. Monomer solution (25 wt % PEGDA, $M_n$=575 Da, 225 mM methyl diethanol amine coinitiator, 37 mM 1-vinyl-2-pyrolldinone, in $H_2O$, pH 9) was purged with argon and then 500 $\mu$L was contacted with the dilution chip surface using a Whatman Chip Clip. Collimated, 495-650 nm polychromatic light was used from an Acticure light source at an intensity of 10 mW/$cm^2$ to initiate polymerization. This was achieved with the use of an in-house 350-650 nm internal interference filter and a 495 nm longpass filter (Edmond Optics) applied to the end of a collimating lens attached to the end of a light guide. Argon was purged from the atmosphere for 5 minutes followed by exposure of light for the desired time period. After amplification, unreacted monomer was removed from the surface by removing the dilution chip out of the chip clip and then gently washing the surface with water.

Polystyerene microspheres encapsulating fluorescent molecules were included in monomer solution for subsequent encapsulation into the hydrogel matrix during polymerization. 0.02 µm diameter, carboxy-modified Nile Red FluoSpheres (Invitrogen) were obtained at a stock concentration of $4.5 \times 10^{15}$ microspheres/mL containing 0.1% sodium azide preservative. The azide preservative was removed with the use of 100,000 Da dialysis columns (Spectra-Por), according to the manufacturer's protocol. The purified FluoSpheres were stored at 4° C. until further use. A 1:50 or 1:10 dilution of the stock solution was made into the established monomer solution. Light intensity was increased accordingly to account for light attenuation occurring from the FluoSpheres over the 1 mm thick monomer layer. The amplification then followed the protocol previously detailed.

Post-Amplification Characterization of Dilution Chips.

Film thicknesses were measured with a Dektak 6M profilometer using a 12.5 µm diamond stylus tip at a minimal stylus force of 1 mg to minimize polymer damage from contact with the pin. Brightfield and fluorescent pictures of amplified dilution chips were obtained through the use of a Leica stereomicroscope calibrated with a Cy3/Cy5 calibration chip (Full Moon Biosystems). Nile Red fluosphere-functionalized polymer films on the surface were further quantified with the use of an Agilent Technologies Microarray scanner (Green channel, PMT 1%) Because of the well-controlled photoinitiator to streptavidin ratio (3:1) achieved in the streptavidin—eosin isothiocyanate (SA-EITC) synthesis (Hansen et al, 2008), the visible light amplification system was chosen as the system to use for quantifiable detection. Arrayed dilution chips containing decreasing surface concentrations of 3' biotin labeled oligos were used to determine the amount of amplification achieved as a function of target oligo surface concentration, determined either through direct measurement of film thickness or through measuring an amplified fluorescent signal. This approach of directly printing the biotinylated target onto the surface serves as a model system (Wilcheck, M.; Bayer, E. A.; Livnah, O. *Immun. Letters*, 2006, 103, 27-32) to evaluate the characteristics of polymerization-based amplification. Such a system is meant to represent a biochip after complementary duplex formation and labeling that may be done either on chip (Pastinen, T. et al. *Gen. Res.*, 2000, 10, 1031-1042; Hultin, E., Kaller, M.; Ahmadian, A.; Lundeberg, J. *Nucleic Acids Res.*, 2005, 33, e48; Erdogan, F. et al. *Nucleic Acids Res.*, 2001, 29, e36) or in solution (Do. J. H.; Choi, D. K. *Eng. Lif Sci.* 2007, 7, 26-34). Thus, the surface density of the biotin label should be directly related to the target concentration, dependent on the hybridization efficiency between a target and its surface-bound complementary capture probe (typically, $K_{hyb} = 10^9$ $M^{-1}$) (Michel, W.; Mai, T.; Naiser, T.; Ott, A. *Biophysical Journal*, 2007, 92, 999-1004), and the labeling efficiency.

Dynamic Amplification and Tunable Sensitivity.

Upon functionalization of a dilution chip with SA-EITC, dilution chips are imaged with a fluorescent scanner to verify the allocation of initiators on the surface at densities proportional to the specific biotin label densities at each site. Long exposure times of low intensity light were used to completely react monomer even from the spots containing the lowest initiator concentrations. At long exposure times, long-wave visible light is desired to minimize or eliminate any nonspecific amplification that is characteristically observed from light sources with emissions in the UV region. Thus, polymerizations using polychromatic green light from a mercury arc lamp at intensities of 10 mW/cm² were performed. The low intensity light allows for slower degradation of initiator into reactive free radicals at the surface, which is desired to achieve decreased termination rates. By examining several longer exposure times in the amplification, times greater than 30 minutes were determined to be required for obtaining maximum sensitivity.

Figure 9:
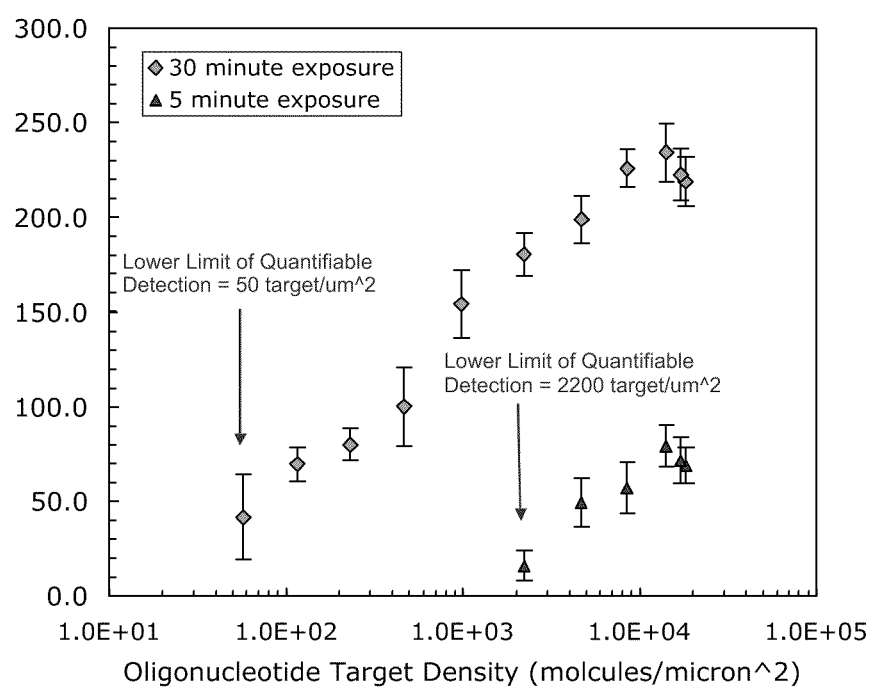
FIG. 9 shows polymer film thickness as a function of oligonucleotide target density for two different light exposure times.

Upon amplification of this system at 30 minutes, polymer films generated from as low as 10 biotin markers/µm² become visually observable under an optical microscope or to the unaided eye. Analysis of film thicknesses at each site showed that a corresponding dynamic profile was achievable from the range of 50 to 4800 biotin markers/µm². This was followed by a saturated region from 6,000 to 15,000 biotin markers/µm² with film thicknesses all in the 230 +/− 20 nm region, independent of marker density, as shown in FIG. 9. The dynamic region of amplification, approaching two orders of magnitude, fits a logarithmic correlation within error, typically less than or equal to 20%. Further demonstrated in FIG. 9 is a tradeoff between assay time and sensitivity for this system. Exposing at times allowing for incomplete conversion of monomer into polymer has the capability to shift the sensitivity of the system, as 5 minutes of exposure shifts sensitivity back to 2,000 biotin markers/µm². Such tunability allows the user capability to implement optimal assay conditions depending on the required sensitivity of the application.

The increase in film thicknesses observed with higher biotin target concentrations is directly due to the corresponding increase of photoinitiator surface concentrations on binding with SA-EITC. With higher photoinitiator concentrations on the surface, an increased number of propagating radical chains are generated during the polymerization process. Such free radicals are capable of diffusing from the surface and through the forming polymer film thereby increasing the conversion of monomer into surface-bound polymer and ultimately increasing film thicknesses. This trend is consistent with both modeling and experimental findings of similar systems in the literature (Kizilel, S.; Perez-Luna, V. H.; Teymour, F. *Macromol. Theroy Simul.* 2006, 15, 686-700). After the polymerization reaches high conversions, radical diffusivity throughout the hydrogel membrane decreases and eventually limits the extent of the polymerization, causing saturation in film thicknesses observed at spots containing higher concentrations of targets. A secondary explanation of saturation may be due to higher termination rates associated with the higher initiator concentrations, which generate higher concentrations of reactive radicals, allowing for increased termination by combination.

The dynamic dependence of film thicknesses with photoinitiator surface concentrations allows for an additional method of controlling the sensitivity of this assay and also enables the ability to tune dynamic amplification to concentration regions of interest. By varying the binding parameters on the surface, allocation of different amounts of photoinitiator to sites containing a constant amount of target is achievable. This potentially allows the user the ability to detect and quantify biotinylated DNA concentrations that may be either undetectable with less efficient binding or in a saturated region with more efficient binding.

Figure 10A:
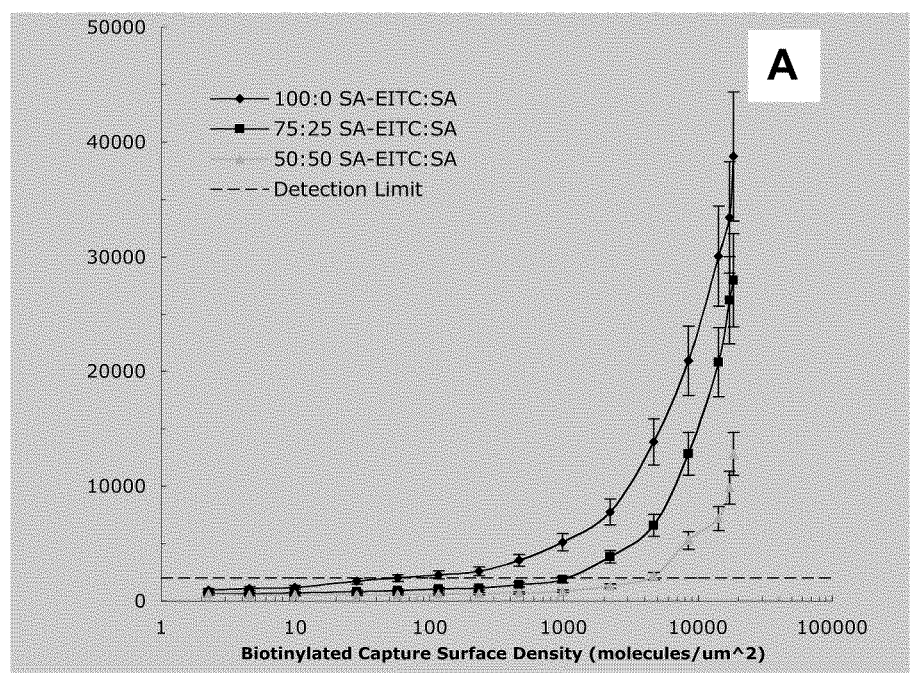
FIG. 10a shows fluorescent intensity versus biotinylated capture surface density (molecules/$\mu m^2$) for various photoinitiator labeling solution concentrations.
Figure 10B:
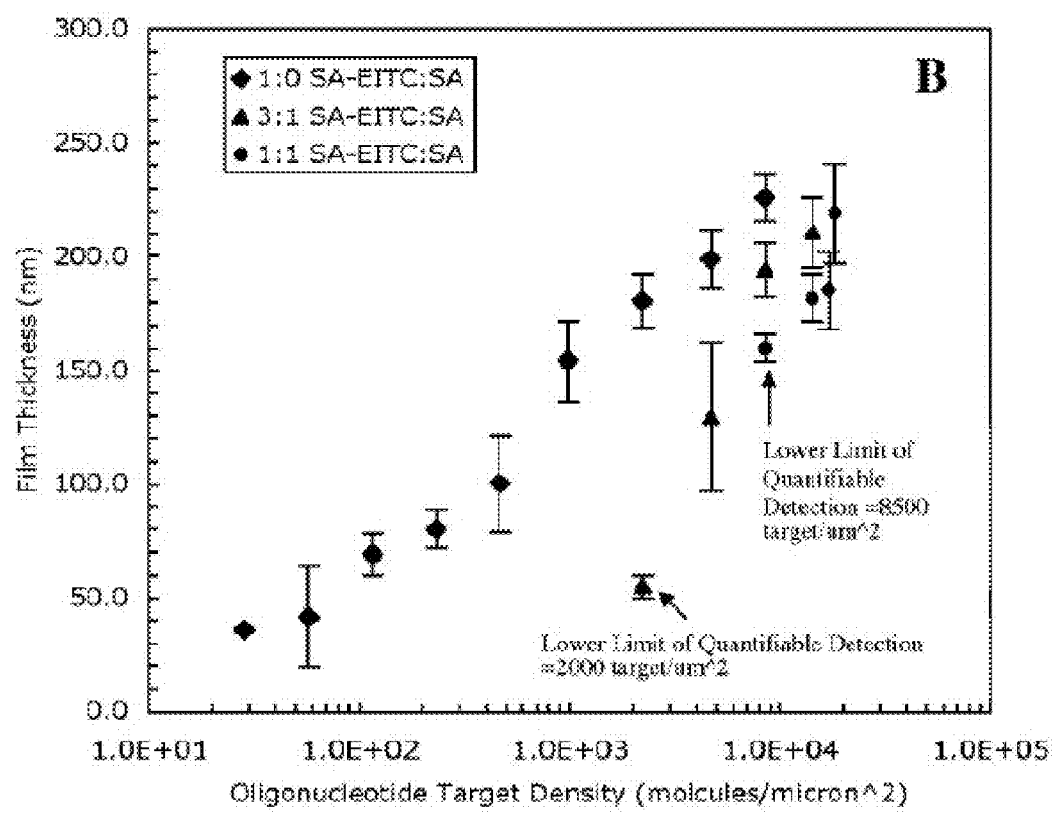
FIG. 10b shows polymer film thickness versus oligonucleotide target density (molecules/$\mu m^2$) for various photoinitiator labeling solution concentrations.

A simple demonstration of this technique can be accomplished through the use of a competitive binding technique involving incubating dilution chips with solutions containing various ratios of unmodified streptavidin (SA) with SA-EITC. Due to the binding of unmodified SA to biotinylated DNA, the concentration of biotinylated DNA available for binding with SA-EITC decreases with higher SA to SA-EITC ratios. Because eosin is a weak fluorophore, a decrease in fluorescent intensities at identical biotin concentrations can be observed on dilution chips functionalized with higher SA:SA-EITC ratios. This signals decreased photoinitiator concentrations at the same biotin concentrations, as shown in FIG. 10A. When incubating with higher SA:SA-EITC ratios, the fluorescent signal required for detection (~2000) is achieved at spots containing higher biotin surface densities. Also, higher end spots with photoinitiator concentrations corresponding to saturation from amplification with out the addition of SA are shifted to quantifiable concentrations at higher SA:SA-EITC ratios. The result of this is a shift in detection limits towards less sensitive detection, but also a shift in the concentration regions of dynamic amplification as shown in FIG. 10B.

In the case of detecting nucleic acid hybridization with polymerization-based amplification, an alternative and perhaps more feasible approach involves varying capture sequence densities. Capture sequence density has been shown both experimentally and through modeling considerations to be a crucial parameter for achieving optimal signal from hybridization (Halperin, A.; Buhot, A.; Zhulina, E. B. *Biophysical Journal*, 2004, 86, 718-730; Pererson, A. W.; Heaton, R. J.; and Georgiadis, R. M. *Nucleic Acids Res.*, 2001, 29, 5163-5168). In effort to shift a saturated response generated from complementary target-capture hybridization to a quantifiable response, sites with less then optimal capture probe densities could be printed. Such sites would then render lower photoinitiator concentrations than optimal sites at the same target concentrations, potentially shifting a saturated response to a quantifiable response. With the high throughput capability of DNA chips, several sites of identical complementary capture sequences could be printed at optimal conditions and successively less than optimal conditions within a single array, allowing for a quantifiable response to be achieved over many orders of magnitude. The capability of quantification at higher ends of the dilution chip extends the total dynamic region observed from polymerization-based amplification to 50 to 18,000 biotins/$\mu m^2$, well over two orders of magnitude. Assuming hybridization constants typical of complementary duplex formation on microarray surfaces ($K_{hyb}=10^9$ $M^{-1}$) (Michel, W.; Mai, T.; Naiser, T.; Ott, A. *Biophysical Journal*, 2007, 92, 999-1004) and that each target sequence can be labeled with a single biotin marker, the regions of quantification amplification correspond to analyte concentrations in the nM to μM range.

Figure 11:
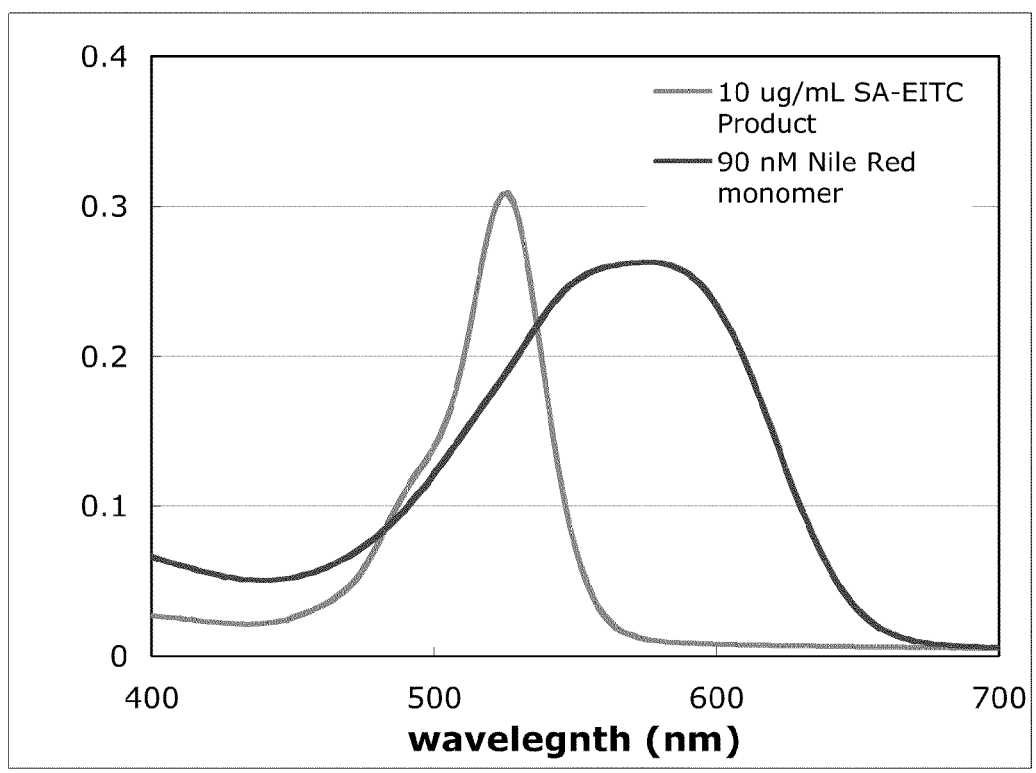
FIG. 11 compares the measured absorbance from a solution containing the streptavidin functionalized initiator (SA-EITC) and from fluorophores contained in the polystyrene nanospheres in monomer solution.
Figure 12:
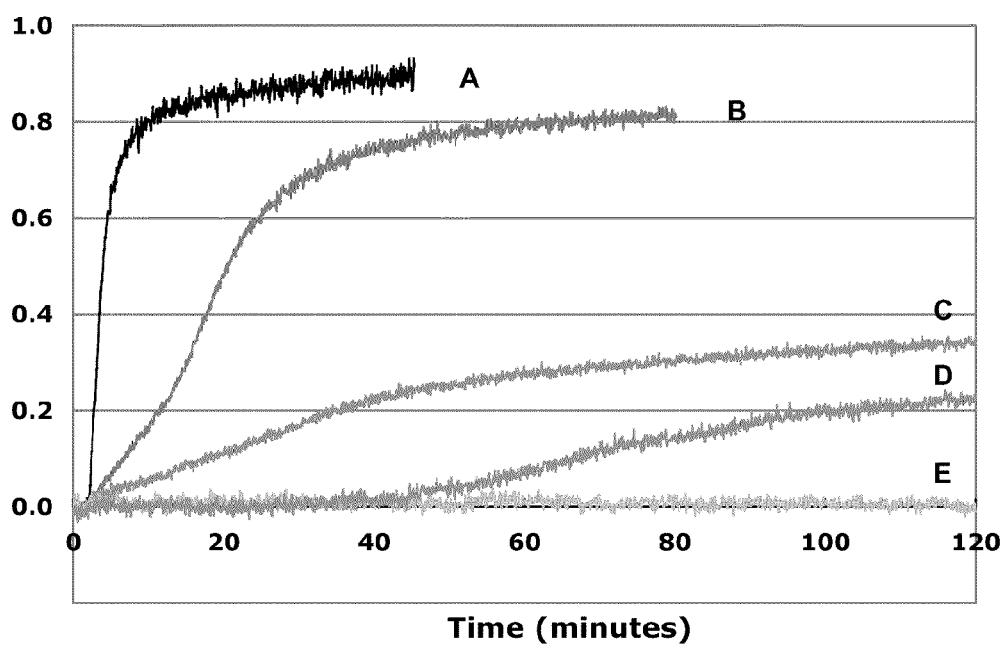
FIG. 12 shows a FTIR conversion plot of hydrogel precursor (25 wt % PEGDA, 225 mM MDEA, 37.5 mM 1-vinyl-2-pyrrolidinone, pH 9.0) at different concentrations of fluorescent nanoparticles and photoinitiator using a 495-650 nm light source at 10 mW/cm$^2$ A) 2 µM eosin (85 µg/mL SA-EITC), 0 nM fluorescent nanoparticles B) 2 µM eosin, 90 nM fluorescent nanoparticles C) 2 µM eosin, 480 nM fluorescent nanoparticles D) 0 µM SA-EITC, 480 nM fluorescent nanoparticles E) 0 µM SA-EITC, 0 nM fluorescent nanoparticles.

Coupling fluorescent signal with polymer growth. To achieve fluorescent signal gains using polymerization-based amplification, 20 nm diameter Nile Red (532/575) FluoSpheres ($8_{532}=2.3\times10^6$ $cm^{-1}$ $M^{-1}$) were added to monomer solution at various dilutions. FIG. 11 shows the absorbance spectra of the monomer solution containing 90 nM fluorescent nanoparticles compared to that of a 10 μg/mL solution of SA-EITC. There is a considerable overlap in absorbance between the monomer solution and the initiator at wavelengths in the 500-650 nm region used to initiate the polymerization reaction, thus adsorption of light from fluorescent monomer effectively decreases initiation rates from SA-EITC at constant light intensity. This effect is observed when monitoring bulk polymerization kinetics under initiation conditions similar to those used during on-chip amplification. The monomer conversion with time is shown in FIG. 12 using 2 μM of SA-EITC, a concentration representing the local concentrations of SA-EITC typically obtained over positive spots on the dilution chips containing dilute amounts of biotin. Both the polymerization kinetics and the final conversion of monomer to polymer decrease due to the addition of nanoparticles. The decrease in final conversion suggests that nanoparticles are capable of terminating propagating free radicals during the polymerization process.

An important observation from FIG. 12 is that without the addition of SA-EITC to monomer, polymerization is only observed at long exposure times (greater than 40 minutes, as shown in FIG. 12D). Photoinitiation due to photoexcited fluorescent nanoparticles at nanomolar concentrations is thus considerably less efficient than initiation from SA-EITC. This exposure window where polymerization occurs exclusively from SA-EITC allows for specificity in the amplification. At lower exposure times, only surface-initiated polymerization will occur on biochips due to the presence of SA-EITC from biotin-avidin binding, while unwanted, non-specific initiation from the fluorescent nanospheres with bulk monomer does not occur until much longer exposures. Thus, the fluorescent monomer system is amenable to on-chip signal amplification to obtain amplified fluorescent signals.

Figure 13A:
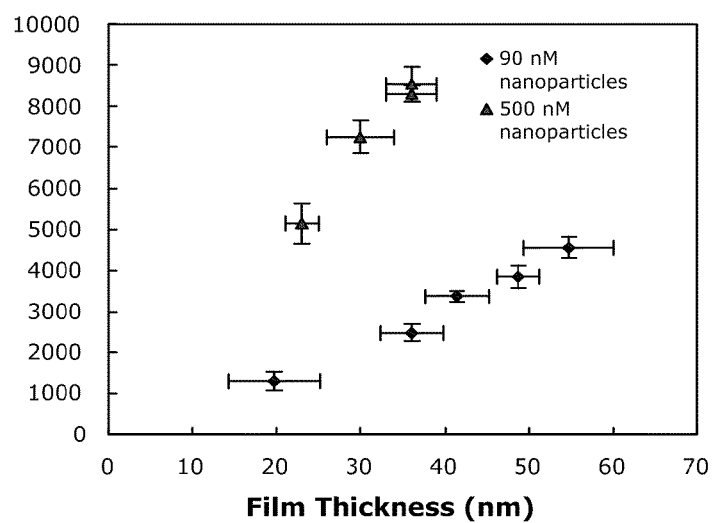
FIG. 13a shows polymer film thicknesses versus fluorescent signal generated from encapsulated fluorescent nanospheres after inclusion in monomer at 90 or 500 nM concentrations.
Figure 13B:
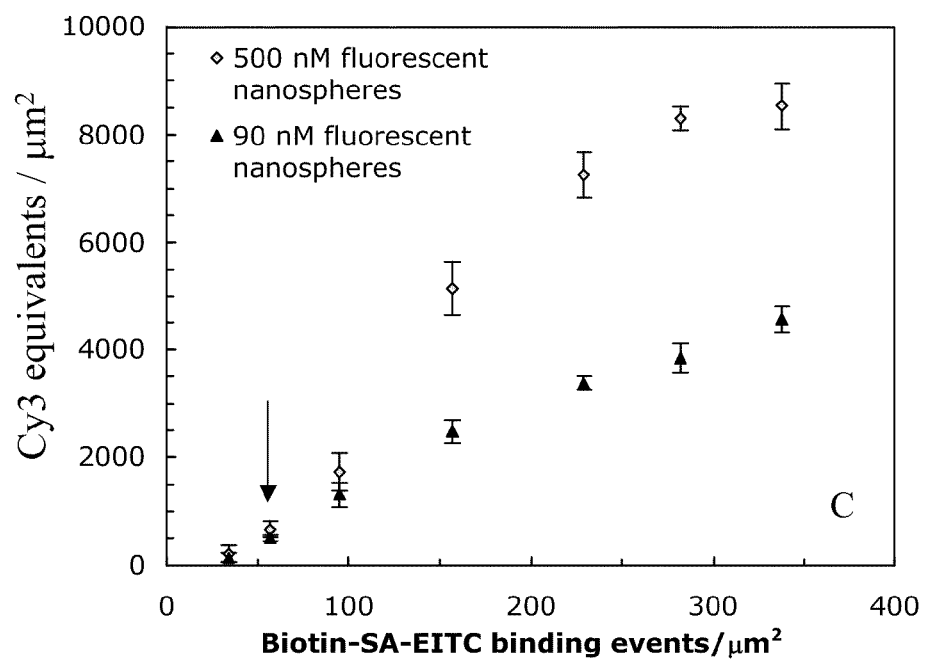
FIG. 13b shows measured fluorophore density verses biotin-SA-EITC binding events after polymerization-based amplification.

Finally, amplification using monomer solutions containing nanomolar concentrations of Nile-Red FluoSpheres from SA-ETC functionalized dilution chips were performed. At 20 nm diameter, the nanospheres become encapsulated into the PEGDA hydrogel matrix and are not released during washing steps, despite lacking covalent attachment into the gel network. Stereomicroscope images of dilution chips showed that before amplification, SA-EITC functionalized spots do not produce a significantly detectable signal. After amplification the last six columns (printed in triplicate) corresponding to higher end biotin concentrations show an amplified, quantifiable signal. FIG. 13a details the increase in fluorescent signal from the amplification. The number of encapsulated nanospheres and the corresponding fluorescent intensity increase monotonically with film thickness after amplification on dilution chips (nanospheres at 90 and 500 nM concentrations). FIG. 13b shows measured fluorophore density verses biotin-SA-EITC binding events after polymerization-based amplification. A large gradient in fluorescent signal ranging from 50 to 8000 Cy3 fluors/$\mu^2$ is achieved that corresponds to the number of biotin-avidin binding events generating the signal. The overall gains in fluorescent signal here range from $10^1$-$10^2$. Because the number of SA-EITC binding events that occur over a given oligonucleotide concentration can be manipulated depending on binding conditions, as previously demonstrated, the amplification is reported in terms of binding events/$\mu m^2$ as opposed to DNA markers/$\mu m^2$. This results in variation of amplified fluorescent signal corresponding linearly to the number of biotin-SA-EITC binding events occurring on the surface over an order of magnitude.

Moreover, the gain in fluorescent signal achieved through the amplification allows for characterization of the biotinylated DNA concentrations using less sophisticated instrumentation. Prior to amplification, SA-EITC functionalized dilution chips were only detectable using a microarray scanner employing a PMT detector with low detection limits measured at ~0.28 Cy3 fluors/$\mu m^2$. After the amplification, the dilution chip was characterized using a stereomicroscope containing a fluorescent CCD camera, a considerably less sophisticated, less expensive instrument with much higher detection limits measured at ~570 Cy3 fluors/$\mu m^2$. Currently, the addition of the nanospheres appears to decrease the polymer film thicknesses and thus the sensitivity of the amplification as opposed to amplification without their inclusion, consistent with the decrease in final conversion of bulk polymerizations with higher amounts of nanoparticles noted from FIG. 12.

SEQUENCE LISTING

<160> NUMBER OF SEQ ID NOS: 1

<210> SEQ ID NO 1
<211> LENGTH: 50
<212> TYPE: DNA
<213> ORGANISM: Artificial Sequence
<220> FEATURE:
<223> OTHER INFORMATION: Synthetic construct: oligonucleotide modified
      at the 3' end with TEG biotin and at the 5' end with an amino
      group.

<400> SEQUENCE: 1
catcacacaa catcacacaa catcacgtat ataaaacgga acgtcgaagg           50

We claim:

1. A method for amplifying a molecular recognition interaction between a target and a probe comprising the steps of:
   a) contacting the target with the probe under conditions effective to form a target-probe complex;
   b) removing target not complexed with the probe;
   c) contacting the target-probe complex with a photoinitiator label under conditions effective to attach the photoinitiator label to the target-probe complex wherein the photoinitiator label comprises a photoreducible dye photoinitiator;
   d) prior to step e), removing photoinitiator label not attached to the target-probe complex;
   e) contacting the photoinitiator-labeled target-probe complex with a polymer precursor solution comprising a polymer precursor, an amine co-initiator, and a plurality of detectable nanoparticles having a size from 5 to 100 nm and encapsulating a fluorescent dye, the detectable nanoparticles not being surface-treated by coupling to the polymer precursor;
   f) exposing the photoinitiator-labeled target-probe complex and the polymer precursor solution to visible light, thereby forming a polymer gel incorporating detectable nanoparticles; and
   g) detecting the formation of the polymer gel incorporating detectable nanoparticles, thereby detecting an amplified target-probe interaction
   wherein the oxygen content of the polymer precursor solution is limited by contacting the polymer precursor solution with a purge gas prior to step e), during step e), during step f), or combinations thereof and the polymer gel has a network structure, the network structure encapsulating the detectable nanoparticles.

2. The method of claim 1, wherein the target-probe complex comprises one of biotin or a biotin-binding protein, the photoinitiator label comprises the other of biotin or a biotin-binding protein, and the photoinitiator label is attached to the target-probe complex by interaction between the biotin and the biotin-binding protein.

3. The method of claim 2, wherein the photoinitiator label comprises a plurality of photoinitiators attached to a biotin-binding protein.

4. The method of claim 3, wherein the average number of photoinitiators attached to the biotin-binding protein is from 2 to 3.

5. The method of claim 1, wherein the photoinitiator is fluorescein, eosin isothiocyanate, eosin Y or Rose Bengal.

6. The method of claim 1 wherein the polymer gel is detected by detecting fluorescence from the detectable nanoparticles.

7. The method of claim 1 wherein the photoinitiator is fluorescein, eosin, eosin isothiocyanate, eosin Y or Rose Bengal and the detectable nanoparticles have an absorption maximum in the range 500 to 670 nm and an emission maximum in the range 510 to 690 nm.

8. The method of claim 1 wherein the detectable nanoparticles are polystyrene nanoparticles or surface-modified polystyrene nanoparticles.

9. The method of claim 1, wherein the target comprises single-stranded DNA (ssDNA) or RNA and the probe comprises ssDNA having a sequence complementary to at least a portion of the sequence of the target.

10. The method of claim 1, wherein the target comprises one of an antibody or antigen and the probe comprises the other of an antibody or antigen.

11. The method of claim 1, wherein the target comprises a first protein, the probe comprises a second protein, and the first and second protein are capable of molecular recognition.

12. The method of claim 1 wherein the polymer precursor solution comprises acrylamide and a bis-acrylamide crosslinker.

13. The method of claim 1 wherein the polymer precursor solution includes a difunctional polymer precursor having a poly(ethylene glycol) backbone and acrylate end groups.

14. A method for identifying a target comprising the steps of
   a) providing a probe array comprising a plurality of different probes, wherein the probes are attached to a solid substrate at known locations;
   b) contacting the target with the probe array under conditions effective to form a target-probe complex;
   c) removing target not complexed with the probe;
   d) contacting the target-probe complex with a photoinitiator label under conditions effective to attach the photoinitiator label to the target-probe complex, the photoinitiator label comprising a photoreducible dye photoinitiator;
   e) prior to step f) removing photoinitiator label not attached to the target-probe complex;
   f) contacting the photoinitiator-labeled target-probe complex with a polymer precursor solution comprising a polymer precursor an amine co-initiator, and a plurality of detectable nanoparticles having a size from 5 to 100 nm and encapsulating a fluorescent dye, the detectable nanoparticles not being surface-treated by coupling to the polymer precursor;

g) exposing the photoinitiator-labeled target-probe complex and the polymer precursor solution to visible light, thereby forming a polymer gel incorporating detectable nanoparticles; and h) detecting the formation of the polymer gel incorporating detectable nanoparticles, wherein the oxygen content of the polymer precursor solution during step f) is limited by contacting the polymer precursor solution with a purge gas prior to step f), during step f), during step g), or combinations thereof and the polymer gel has a network structure, the network structure encapsulating the detectable nanoparticles and the location of the polymer gel incorporating detectable nanoparticles indicates the probe which forms a target-probe complex with the target, thereby identifying the target.

15. The method of claim 14, wherein the target-probe complex comprises one of biotin or a biotin-binding protein, the photoinitiator label comprises the other of biotin or a biotin-binding protein, and the photoinitiator label is attached to the target-probe complex by interaction between the biotin and the biotin-binding protein.

16. The method of claim 15, wherein the photoinitiator label comprises a plurality of photoinitiators attached to a biotin-binding protein.

17. The method of claim 16, wherein the average number of photoinitiators attached to the biotin-binding protein is from 2 to 3.

18. The method of claim 14, wherein the photoinitiator is fluorescein, eosin, eosin isothiocyanate, eosin Y or Rose Bengal.

19. The method of claim 14, wherein the polymer gel is detected through detecting fluorescence of the detectable nanoparticles.

20. The method of claim 14 wherein the photoinitiator is fluorescein, eosin, eosin isothiocyanate, eosin Y or Rose Bengal and the detectable nanoparticles have an absorption maximum in the range 500 to 670 nm and an emission maximum in the range 510 to 690 nm.

21. The method of claim 14 wherein the detectable nanoparticles are polystyrene nanoparticles or surface-modified polystyrene nanoparticles.

22. The method of claim 14 wherein the target comprises single-stranded DNA (ssDNA) or RNA and the probe comprises ssDNA having a sequence complementary to at least a portion of the sequence of the target.

23. The method of claim 14 wherein the target comprises one of an antibody or antigen and the probe comprises the other of an antibody or antigen.

24. The method of claim 14, wherein the target comprises a first protein, the probe comprises a second protein, and the first and second proteins are capable of molecular recognition.

25. The method of claim 14 wherein the polymer precursor solution comprises acrylamide and a bis-acrylamide crosslinker.

26. The method of claim 14 wherein the polymer precursor solution includes a difunctional polymer precursor having a poly(ethylene glycol) backbone and acrylate end groups.

27. The method of claim 1 wherein the polymer gel has a network structure, the network structure encapsulating the detectable nanoparticles without covalent attachment of the detectable nanoparticles to the network structure.

28. The method of claim 1 wherein the nanoparticles have a size from 10 to 50 nm.

29. The method of claim 14 wherein the polymer gel has a network structure, the network structure encapsulating the detectable nanoparticles without covalent attachment of the detectable nanoparticles to the network structure.

30. The method of claim 14 wherein the nanoparticles have a size from 10 to 50 nm.

31. The method of claim 1 wherein the detectable nanoparticles are surface-treated by carboxylate modification.

32. The method of claim 1 wherein the detectable nanoparticles are surface-treated by amine modification.

33. The method of claim 14 wherein the detectable nanoparticles are surface-treated by carboxylate modification.

34. The method of claim 14 wherein the detectable nanoparticles are surface-treated by amine modification.

* * * * *